United States Patent
Bacus et al.

(10) Patent No.: US 7,149,332 B2
(45) Date of Patent: *Dec. 12, 2006

(54) METHOD AND APPARATUS FOR INTERNET, INTRANET, AND LOCAL VIEWING OF VIRTUAL MICROSCOPE SLIDES

(75) Inventors: James W. Bacus, Oakbrook, IL (US); James V. Bacus, Downers Grove, IL (US)

(73) Assignee: Bacus Laboratories, Inc., Lombard, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/752,072

(22) Filed: Jan. 5, 2004

(65) Prior Publication Data

US 2004/0141637 A1    Jul. 22, 2004

Related U.S. Application Data

(63) Continuation of application No. 10/017,673, filed on Dec. 14, 2001, now Pat. No. 6,674,881, which is a continuation of application No. 09/592,561, filed on Jun. 12, 2000, now Pat. No. 6,396,941, which is a continuation-in-part of application No. 09/032,514, filed on Feb. 27, 1998, now Pat. No. 6,272,235, which is a continuation-in-part of application No. 08/805,856, filed on Mar. 3, 1997, now Pat. No. 6,101,265, which is a continuation-in-part of application No. 08/701,974, filed on Aug. 23, 1996, now Pat. No. 6,031,930.

(60) Provisional application No. 60/177,550, filed on Jan. 21, 2000.

(51) Int. Cl.
   *G06K 9/00*    (2006.01)

(52) U.S. Cl. ............. 382/128; 382/129; 382/133; 382/134; 348/79; 348/80; 348/211.3; 359/363; 359/368; 359/369; 359/381; 345/744; 600/168; 709/203; 709/219; 725/82

(58) Field of Classification Search ........... 382/128, 382/129, 133, 134; 348/79, 80, 211.3; 359/363, 359/368, 369, 381; 345/744; 600/168; 709/203, 709/219; 725/82
See application file for complete search history.

(56) References Cited

U.S. PATENT DOCUMENTS 3,999,047 A    12/1976    Green (Continued)

FOREIGN PATENT DOCUMENTS

EP    0 209 422    1/1987

(Continued)

OTHER PUBLICATIONS

Szeliski R: "*Image Mosaicing for Tele-Reality Applications*" Proceedings of the IEEE Workshop on Applications of Computer Vision, XX, XX, May 1, 1994, pp. 44-53, XP 002048809.

(Continued)

*Primary Examiner*—Andrew W. Johns
*Assistant Examiner*—Patrick L. Edwards
(74) *Attorney, Agent, or Firm*—Fitch, Even, Tabin & Flannery

(57) ABSTRACT

A method of and apparatus for viewing microscopic images include transmitting tiled microscopic images from a server to a client. The client assembles the tiled images into a seamless virtual slide or specimen image and provides tools for manipulating image magnification and viewpoint. The method and apparatus also provides a virtual multi-headed microscope function which allows scattered viewers to simultaneously view and interact with a coherent magnified microscopic image.

33 Claims, 37 Drawing Sheets

U.S. PATENT DOCUMENTS

| | | |
|---|---|---|
| 4,150,360 A | 4/1979 | Kopp et al. |
| 4,175,860 A | 11/1979 | Bacus |
| 4,199,748 A | 4/1980 | Bacus |
| 4,213,036 A | 7/1980 | Kopp et al. |
| 4,523,278 A | 6/1985 | Reinhardt et al. |
| 4,673,988 A | 6/1987 | Jansson et al. |
| 4,742,558 A | 5/1988 | Ishibashi et al. |
| 4,887,892 A | 12/1989 | Bacus |
| 4,965,725 A | 10/1990 | Rutenberg |
| 5,068,906 A | 11/1991 | Kosaka |
| 5,072,382 A | 12/1991 | Kamentsky |
| 5,073,857 A | 12/1991 | Peters et al. |
| 5,099,521 A | 3/1992 | Kosaka |
| 5,107,422 A | 4/1992 | Kamentsky et al. |
| 5,123,056 A | 6/1992 | Wilson |
| 5,163,095 A | 11/1992 | Kosaka |
| 5,216,500 A | 6/1993 | Krummey et al. |
| 5,216,596 A | 6/1993 | Weinstein |
| 5,218,645 A | 6/1993 | Bacus |
| 5,252,487 A | 10/1993 | Bacus et al. |
| 5,257,182 A | 10/1993 | Luck et al. |
| 5,260,871 A | 11/1993 | Goldberg |
| 5,268,966 A | 12/1993 | Kasdan |
| 5,287,272 A | 2/1994 | Rutenberg et al. |
| 5,297,034 A * | 3/1994 | Weinstein ............ 382/128 |
| 5,313,532 A | 5/1994 | Harvey et al. |
| 5,333,207 A | 7/1994 | Rutenberg |
| 5,473,706 A | 12/1995 | Bacus et al. |
| 5,499,097 A | 3/1996 | Ortyn et al. |
| 5,505,946 A | 4/1996 | Kennedy et al. |
| 5,544,650 A | 8/1996 | Boon et al. |
| 5,625,765 A | 4/1997 | Ellenby et al. |
| 5,687,251 A | 11/1997 | Erler et al. |
| 5,784,162 A | 7/1998 | Cabib et al. |
| 5,793,969 A * | 8/1998 | Kamentsky et al. ........ 709/213 |
| 5,796,861 A | 8/1998 | Vogt et al. |
| 5,836,877 A | 11/1998 | Zavislan |
| 5,838,837 A | 11/1998 | Hirosawa et al. |
| 6,148,096 A * | 11/2000 | Pressman et al. ........... 382/133 |
| 6,535,626 B1 * | 3/2003 | Pressman et al. ........... 382/133 |
| 6,684,092 B1 * | 1/2004 | Zavislan .................... 600/407 |

FOREIGN PATENT DOCUMENTS

| | | |
|---|---|---|
| EP | 0 246 010 A | 11/1987 |
| JP | 05-313071 | 11/1993 |
| JP | 06-118307 | 4/1994 |
| JP | 07-015721 | 1/2005 |

OTHER PUBLICATIONS

Krishnan A et al.: "*Panoramic Image Acquisition*" Proceedings 1996 IEEE Computer Society Conference on Computer Vision and Pattern Recognition (CAT No. 96CB35909), Proceedings of IEEE Conference on Computer Vision and Pattern Recognition, San Francisco, CA, USA Jun. 18-20, 1996.

Szeliski et al.; "*Direct Methods for Visual Scene Reconstruction*" Digital Equipment Corporation Cambridge Research Lab, pp. 26-33, Jun. 24, 1995.

Dani et al.: "*Automated Assembling of Images: Image Montage Preparation*" Department of Electrical Engineering, Indian Institute of Technology, pp. 431-445, Oct. 24, 1993.

Charles W. Boone and Gary J. Kelloff, "*Biomarkers of Premalignant Breast Disease and Their Use as Surrogate Endpoints in Clinical Trials of Chemopreventive Agents*" *The Breast Journal* vol. 1, No. 4, pp. 228-235 (1995), 8 pages.

Norman J. Pressman, "*Markovian Analysis of Cervical Cell Images*" *The Journal of Histochemistry and Cytochemistry* vol. 24, No. 1, pp. 138-144 (1976), 7 pages.

"*The CAS 200™ Multiscan™ Automated Pathology Workstation*" by James V. Bacus, Compendium on the Computerized Cytology and Histology Laboratory, Tutorials of Cytology © 1994.

Henderson, E. "*Image Acquisition of Microscopic Slides*," Spie vol. 2173: pp 21-27.

Silage, D et al., "*Digital Image Tiles: A Method for the Processing of Large Sections*" Journal of Microscopy, vol. 138, Pt 2, May 1985, pp. 221-227.

\* cited by examiner

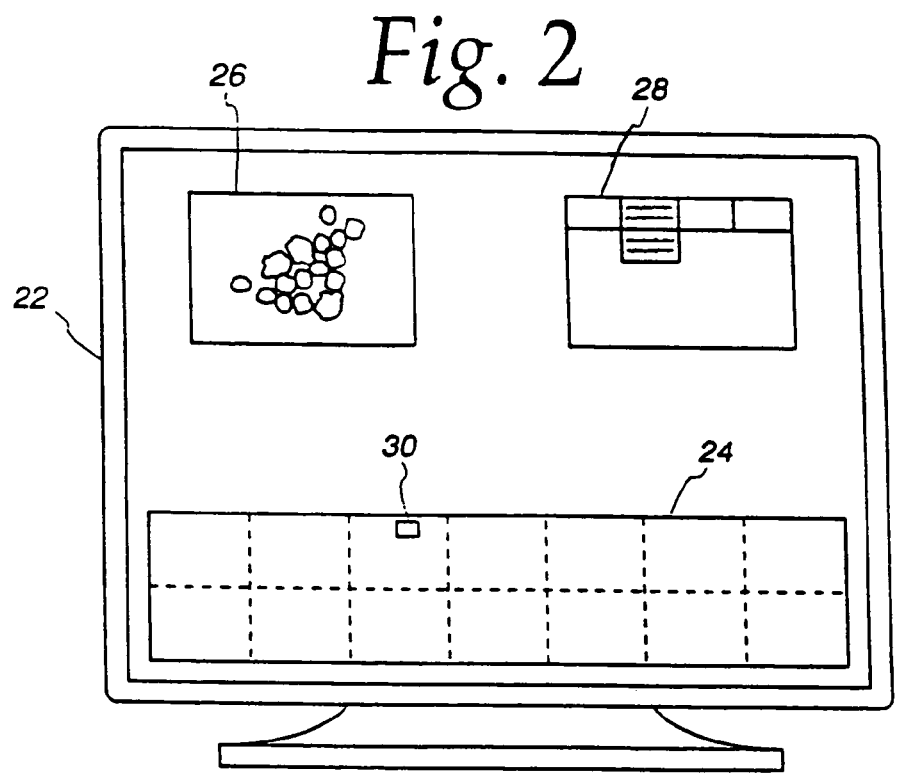
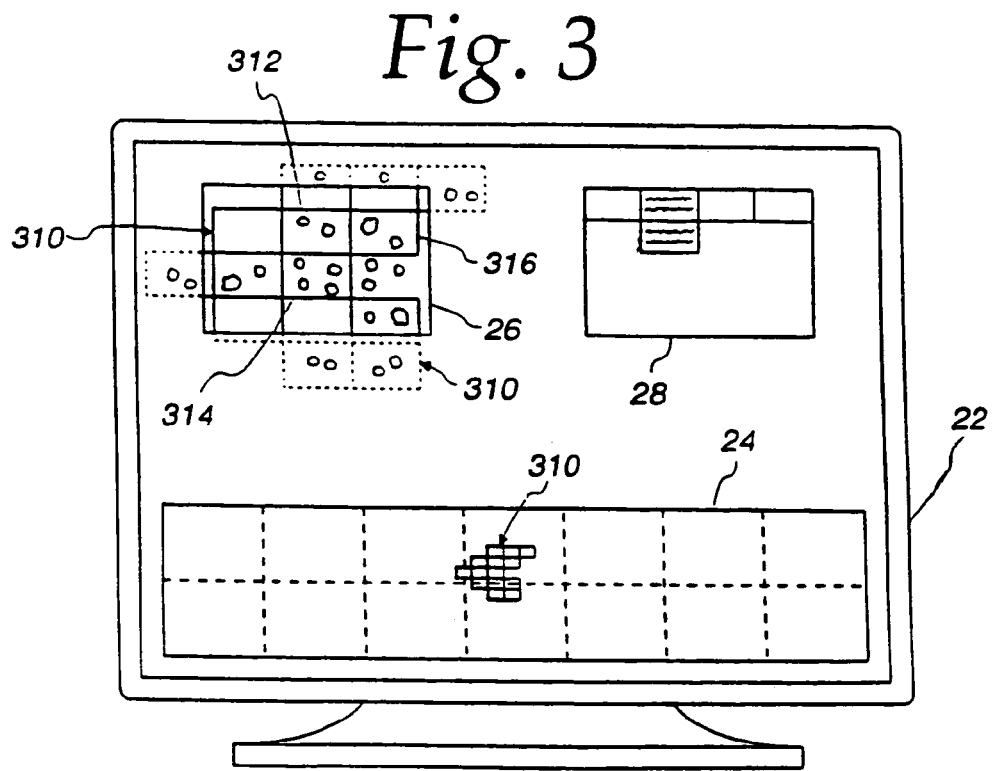

FIG. 7A

| | | | |
|---|---|---|---|
| ☐ FINAL SCAN.INI | ☐ DA29.BMP | ☐ DA55.BMP | ☐ SS18.BMP |
| ☐ SLIDE SCAN.INI | ☐ DA3.BMP | ☐ DA56.BMP | ☐ SS19.BMP |
| ☐ DA0.BMP | ☐ DA30.BMP | ☐ DA57.BMP | ☐ SS2.BMP |
| ☐ DA1.BMP | ☐ DA31.BMP | ☐ DA58.BMP | ☐ SS20.BMP |
| ☐ DA10.BMP | ☐ DA32.BMP | ☐ DA59.BMP | ☐ SS21.BMP |
| ☐ DA100.BMP | ☐ DA33.BMP | ☐ DA6.BMP | ☐ SS22.BMP |
| ☐ DA101.BMP | ☐ DA34.BMP | ☐ DA60.BMP | ☐ SS23.BMP |
| ☐ DA102.BMP | ☐ DA35.BMP | ☐ DA61.BMP | ☐ SS24.BMP |
| ☐ DA103.BMP | ☐ DA36.BMP | ☐ DA62.BMP | ☐ SS25.BMP |
| ☐ DA104.BMP | ☐ DA37.BMP | ☐ DA63.BMP | ☐ SS26.BMP |
| ☐ DA11.BMP | ☐ DA38.BMP | ☐ DA64.BMP | ☐ SS27.BMP |
| ☐ DA12.BMP | ☐ DA39.BMP | ☐ DA65.BMP | ☐ SS28.BMP |
| ☐ DA13.BMP | ☐ DA4.BMP | ☐ DA66.BMP | ☐ SS29.BMP |
| ☐ DA14.BMP | ☐ DA40.BMP | ☐ DA67.BMP | ☐ SS3.BMP |
| ☐ DA15.BMP | ☐ DA41.BMP | ☐ DA68.BMP | ☐ SS30.BMP |
| ☐ DA16.BMP | ☐ DA42.BMP | ☐ DA69.BMP | ☐ SS31.BMP |
| ☐ DA17.BMP | ☐ DA43.BMP | ☐ DA7.BMP | ☐ SS32.BMP |
| ☐ DA18.BMP | ☐ DA44.BMP | ☐ DA70.BMP | ☐ SS33.BMP |
| ☐ DA19.BMP | ☐ DA45.BMP | ☐ DA71.BMP | ☐ SS34.BMP |
| ☐ DA2.BMP | ☐ DA46.BMP | ☐ DA72.BMP | ☐ SS35.BMP |
| ☐ DA20.BMP | ☐ DA47.BMP | ☐ DA73.BMP | ☐ SS36.BMP |
| ☐ DA21.BMP | ☐ DA48.BMP | ☐ DA74.BMP | ☐ SS37.BMP |
| ☐ DA22.BMP | ☐ DA49.BMP | ☐ DA75.BMP | ☐ SS4.BMP |
| ☐ DA23.BMP | ☐ DA5.BMP | ☐ DA76.BMP | ☐ SS5.BMP |
| ☐ DA24.BMP | ☐ DA50.BMP | ☐ DA77.BMP | ☐ SS6.BMP |
| ☐ DA25.BMP | ☐ DA51.BMP | ☐ DA78.BMP | ☐ SS7.BMP |
| ☐ DA26.BMP | ☐ DA52.BMP | ☐ DA79.BMP | ☐ SS8.BMP |
| ☐ DA27.BMP | ☐ DA53.BMP | ☐ DA8.BMP | ☐ SS9.BMP |
| ☐ DA28.BMP | ☐ DA54.BMP | ☐ DA80.BMP | ☐ MDA027.TRA |
| | | ☐ DA81.BMP | |
| | | ☐ DA82.BMP | |
| | | ☐ DA83.BMP | |
| | | ☐ DA84.BMP | |
| | | ☐ DA85.BMP | |
| | | ☐ DA86.BMP | |
| | | ☐ DA87.BMP | |
| | | ☐ DA88.BMP | |
| | | ☐ DA89.BMP | |
| | | ☐ DA9.BMP | |
| | | ☐ DA90.BMP | |
| | | ☐ DA91.BMP | |
| | | ☐ DA92.BMP | |
| | | ☐ DA93.BMP | |
| | | ☐ DA94.BMP | |
| | | ☐ DA95.BMP | |
| | | ☐ DA96.BMP | |
| | | ☐ DA97.BMP | |
| | | ☐ DA98.BMP | |
| | | ☐ DA99.BMP | |
| | | ☐ SS1.BMP | |
| | | ☐ SS10.BMP | |
| | | ☐ SS11.BMP | |
| | | ☐ SS12.BMP | |
| | | ☐ SS13.BMP | |
| | | ☐ SS14.BMP | |
| | | ☐ SS15.BMP | |
| | | ☐ SS16.BMP | |
| | | ☐ SS17.BMP | |

FIG. 7B

☐ BBFINALSCAN.CLASS
☐ BBMESSAGEBOX.CLASS
☐ BBWEBSLIDE.CLASS

FIG. 8

| | | | |
|---|---|---|---|
| ☐ WEBSLIDE | ☐ DA29.BMP | ☐ DA55.BMP | ☐ DA81.BMP | ☐ SS18.BMP
| ☐ INDEX.HTML | ☐ DA3.BMP | ☐ DA56.BMP | ☐ DA82.BMP | ☐ SS19.BMP
| ☐ DA0.BMP | ☐ DA30.BMP | ☐ DA57.BMP | ☐ DA83.BMP | ☐ SS2.BMP
| ☐ DA1.BMP | ☐ DA31.BMP | ☐ DA58.BMP | ☐ DA84.BMP | ☐ SS20.BMP
| ☐ DA10.BMP | ☐ DA32.BMP | ☐ DA59.BMP | ☐ DA85.BMP | ☐ SS21.BMP
| ☐ DA100.BMP | ☐ DA33.BMP | ☐ DA6.BMP | ☐ DA86.BMP | ☐ SS22.BMP
| ☐ DA101.BMP | ☐ DA34.BMP | ☐ DA60.BMP | ☐ DA87.BMP | ☐ SS23.BMP
| ☐ DA102.BMP | ☐ DA35.BMP | ☐ DA61.BMP | ☐ DA88.BMP | ☐ SS24.BMP
| ☐ DA103.BMP | ☐ DA36.BMP | ☐ DA62.BMP | ☐ DA89.BMP | ☐ SS25.BMP
| ☐ DA104.BMP | ☐ DA37.BMP | ☐ DA63.BMP | ☐ DA9.BMP | ☐ SS26.BMP
| ☐ DA11.BMP | ☐ DA38.BMP | ☐ DA64.BMP | ☐ DA90.BMP | ☐ SS27.BMP
| ☐ DA12.BMP | ☐ DA39.BMP | ☐ DA65.BMP | ☐ DA91.BMP | ☐ SS28.BMP
| ☐ DA13.BMP | ☐ DA4.BMP | ☐ DA66.BMP | ☐ DA92.BMP | ☐ SS29.BMP
| ☐ DA14.BMP | ☐ DA40.BMP | ☐ DA67.BMP | ☐ DA93.BMP | ☐ SS3.BMP
| ☐ DA15.BMP | ☐ DA41.BMP | ☐ DA68.BMP | ☐ DA94.BMP | ☐ SS30.BMP
| ☐ DA16.BMP | ☐ DA42.BMP | ☐ DA69.BMP | ☐ DA95.BMP | ☐ SS31.BMP
| ☐ DA17.BMP | ☐ DA43.BMP | ☐ DA7.BMP | ☐ DA96.BMP | ☐ SS32.BMP
| ☐ DA18.BMP | ☐ DA44.BMP | ☐ DA70.BMP | ☐ DA97.BMP | ☐ SS33.BMP
| ☐ DA19.BMP | ☐ DA45.BMP | ☐ DA71.BMP | ☐ DA98.BMP | ☐ SS34.BMP
| ☐ DA2.BMP | ☐ DA46.BMP | ☐ DA72.BMP | ☐ DA99.BMP | ☐ SS35.BMP
| ☐ DA20.BMP | ☐ DA47.BMP | ☐ DA73.BMP | ☐ SS1.BMP | ☐ SS36.BMP
| ☐ DA21.BMP | ☐ DA48.BMP | ☐ DA74.BMP | ☐ SS10.BMP | ☐ SS37.BMP
| ☐ DA22.BMP | ☐ DA49.BMP | ☐ DA75.BMP | ☐ SS11.BMP | ☐ SS4.BMP
| ☐ DA23.BMP | ☐ DA5.BMP | ☐ DA76.BMP | ☐ SS12.BMP | ☐ SS5.BMP
| ☐ DA24.BMP | ☐ DA50.BMP | ☐ DA77.BMP | ☐ SS13.BMP | ☐ SS6.BMP
| ☐ DA25.BMP | ☐ DA51.BMP | ☐ DA78.BMP | ☐ SS14.BMP | ☐ SS7.BMP
| ☐ DA26.BMP | ☐ DA52.BMP | ☐ DA79.BMP | ☐ SS15.BMP | ☐ SS8.BMP
| ☐ DA27.BMP | ☐ DA53.BMP | ☐ DA8.BMP | ☐ SS16.BMP | ☐ SS9.BMP
| ☐ DA28.BMP | ☐ DA54.BMP | ☐ DA80.BMP | ☐ SS17.BMP | |

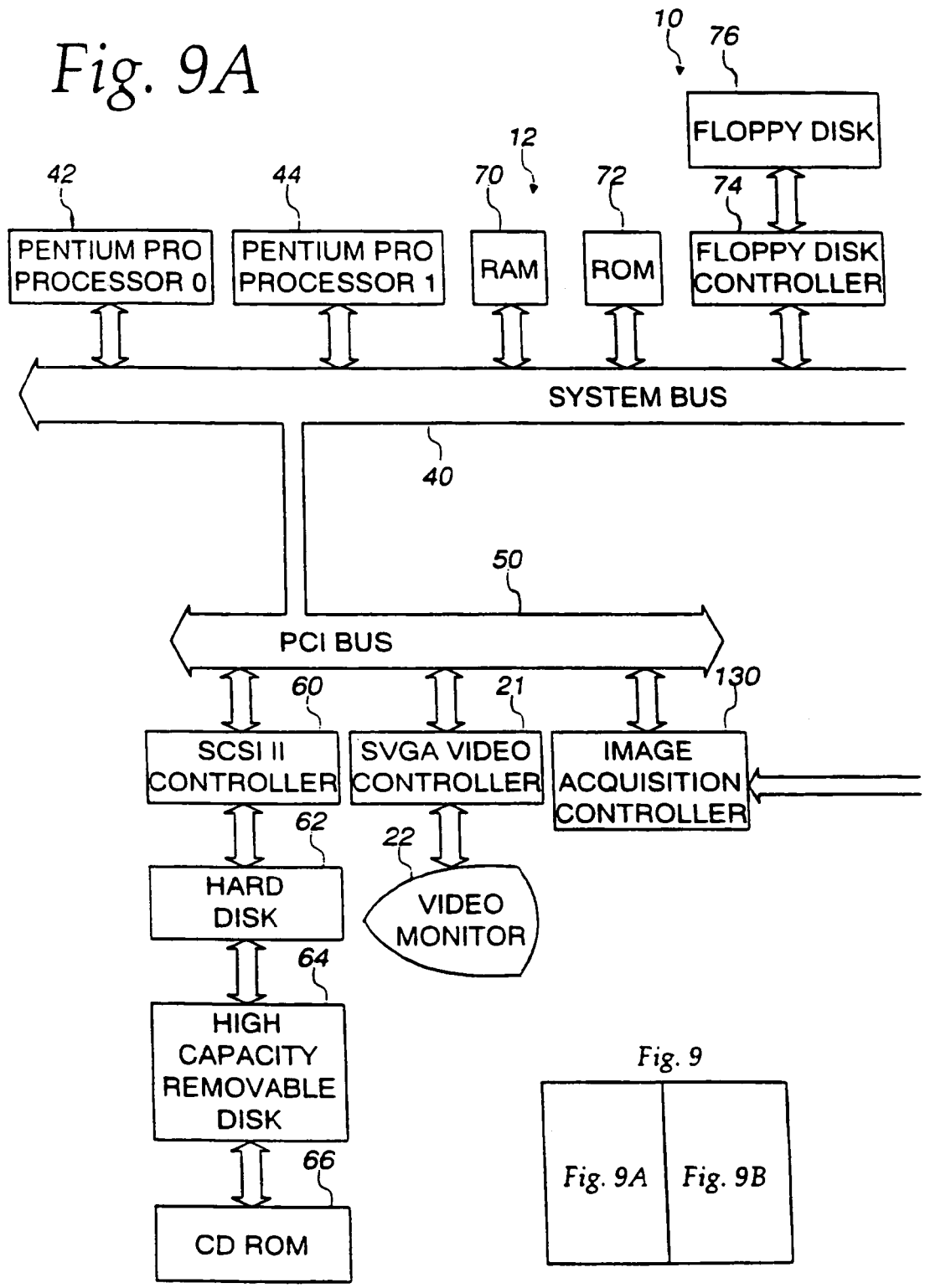

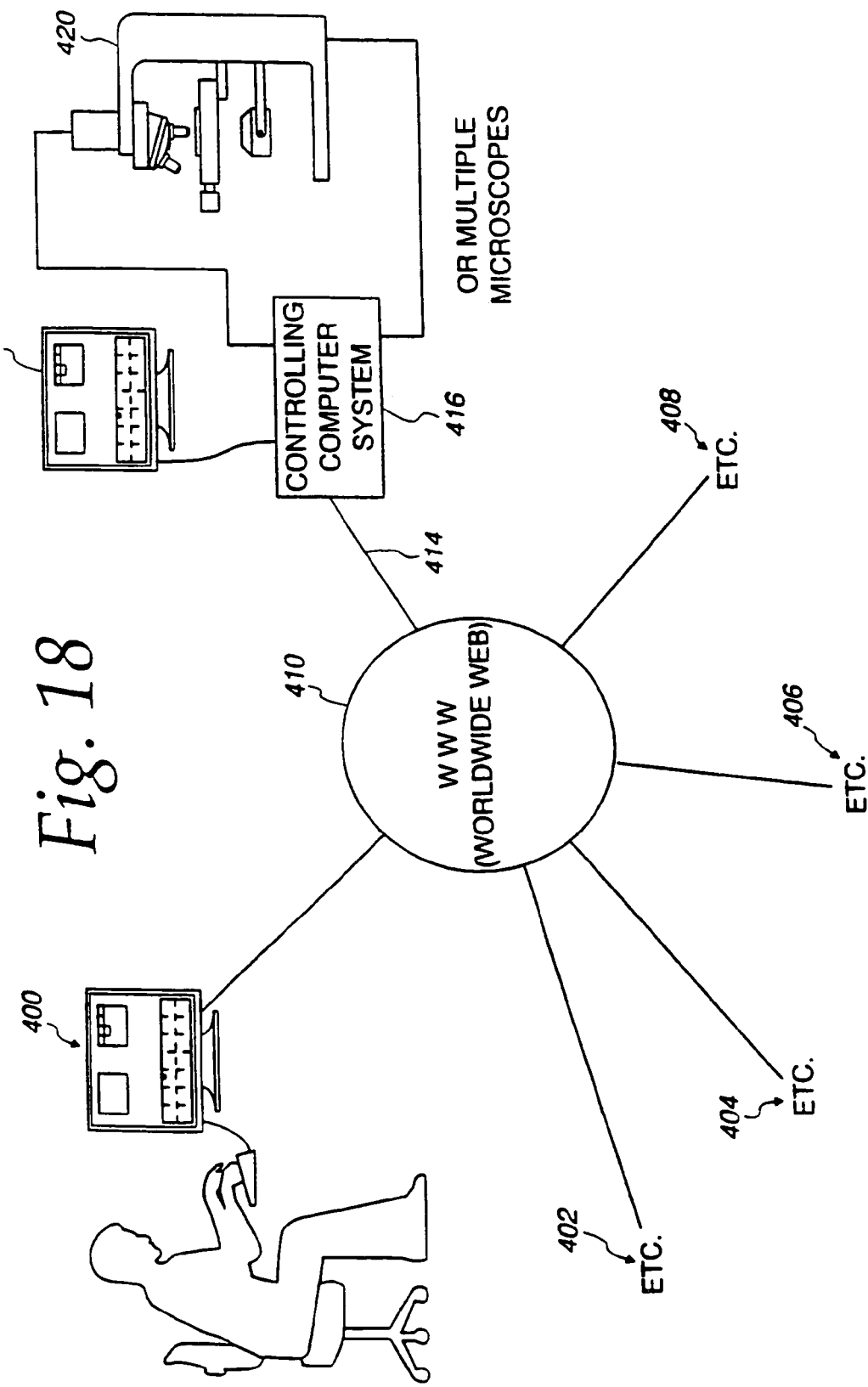

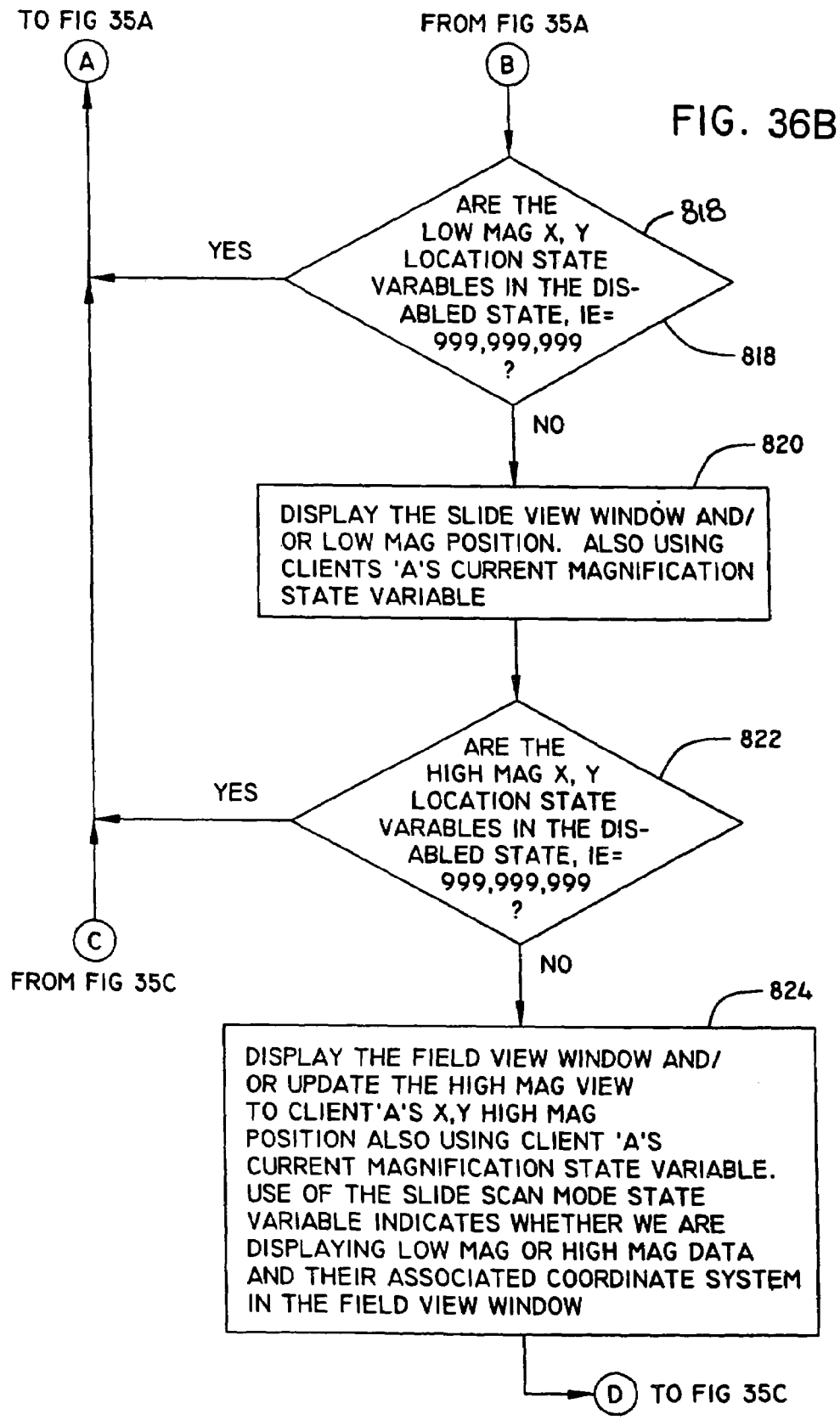

US 7,149,332 B2

METHOD AND APPARATUS FOR INTERNET, INTRANET, AND LOCAL VIEWING OF VIRTUAL MICROSCOPE SLIDES

CROSS REFERENCE TO RELATED APPLICATIONS

This is a continuation of U.S. patent application Ser. No. 10/017,673, filed Dec. 14, 2001, now U.S. Pat. No. 6,674,881, which is hereby incorporated by reference in its entirety, which is a continuation application of U.S. patent application Ser. No. 09/592561, filed Jun. 12, 2000, now U.S. Pat. No. 6,396,941. This application claims the benefit of U.S. Provisional Patent Application No. 60/177,550 filed Jan. 12, 2000, which is a continuation-in-part of U.S. patent application Ser. No. 09/032,514 filed Feb. 27, 1998, now U.S. Pat. No. 6,272,235 which is a continuation-in-part of U.S. patent application Ser. No. 08/805,856 filed Mar. 3, 1997, now U.S. Pat. No. 6,101,265, which is a continuation-in-part of U.S. patent application Ser. No. 08/701,974 filed Aug. 23, 1996, now U.S. Pat. No. 6,031,930.

BACKGROUND OF THE INVENTION

The invention relates to a method of and an apparatus for storing and viewing virtual microscope slides. The method and apparatus are usable over the Internet, an intranet, or on a local computer, and provide an integrated and interlocked combination of a digital image server and multiple virtual microscope client viewers.

Examination of tissue sections, aspirated tissue, and the like, has typically been a localized activity. That is, the tissue is sectioned in a lab. It may be stained and microscopically examined by a light microscope after which a technician and/or a pathologist reaches a conclusion as to the characteristics of the tissue; for instance whether the tissue is benign or malignant and what stage of malignancy the tissue might be in. A number of patents awarded to the instant inventors are directed to that sort of system.

In some cases, however, it may be desirable where results are indefinite or where particular sophistication is needed for the human analysis of the images to be able to supply the slides to an offsite expert who might be across the country or on the other side of the world. In the past, the approach which has been taken to solve this problem has involved the transfer of the slides themselves by air express or post, often involving significant time delays which it would be desirable to avoid if a patient is suspected of being severely ill.

In the alternative, telepathology systems have been made available involving the use of television transmissions requiring a 6 MHz bandwidth, either through a satellite link or possibly through a coaxial cable, both of which must, in effect, be dedicated lines and previously set up. Such a system, however, requires a great deal of customization and expense although such systems do include the use of computer-controlled microscopes. Such microscopes receive commands from a remote location to move to a particular position on a slide so that the television camera may send a television signal out representative of the field of view.

This type of system is relatively expensive and clumsy to use do to the necessity for a very expensive robotically-controlled microscope which receives specialized signals over a dedicated link.

What is needed then is a system and apparatus which can allow a remote consult to take place related to tissue specimens, and the like, which may be done quickly, conveniently, and easily.

SUMMARY OF THE INVENTION

The invention relates to a method for viewing virtual microscope slides. Virtual microscope slides comprise sets of tiled images. The tiles of the tiled images represent a field of view which may be captured from a microscope having a high-precision controlled stage typically with a stage resolution in the neighborhood of a 1/10th micron step. The images are captured on a CCD array which generates images in color or black and white and stores them in a frame buffer or on disk in tiled format. Such images are usually very large due to the number of pixels required to reproduce a substantial size tissue specimen at a high magnification, such as 40 power. In addition, in order to provide ease of use, particularly on a remote basis, other sets of tiled images have a lower magnification, for instance at 1.25 power. All of the images are tiled and stored in digital format on a server which may communicate using the hypertext transport protocol used for web-based communications over a packet switching network such as the Internet or an intranet. Because the images have already been captured and coordinated in tiled form, it is unnecessary to provide a robotically-controlled microscope or even the original specimens themselves.

One or more clients may communicate with the server containing the image to download a portion or all of the tiled image. The client provides requests to the server indicating the portion which is desired to be viewed and the server supplies the appropriate tiles for that portion of the image. The tiles are received by the client and are assembled into a seamless view which may be scrolled through and scanned in the same manner as a pathologist may move about a microscope slide to find regions of interest. In addition, the low-magnification image may be displayed in a first window at the client and a higher-magnification image may simultaneously be displayed which retains coherence with the lower-magnification image in order to provide ease of scanning for areas of interest by the pathology, or the like.

Furthermore, the client/server relationship may be carried out over multiple clients with one of the clients having control over the image positioning as fed by the server for all other clients via communication between the first client and the server, and then subsequent updating coherent communication between the server and the downstream clients. This does not necessarily require that repeated loading take place of the client images, but only that signals be sent between the server and the secondary clients reflecting the field which the first client is viewing. In this way, the overall system can operate similarly to a multiheaded optical microscope of the type used to train physicians in pathology. Furthermore, the system can be used as a multiheaded microscope during a consult so that al persons simultaneously involved in the consult are looking at the same portion of the image and no confusion can arise.

A further advantage of the present invention is to provide packet switched chat communications along with the multiheaded virtual microscope feature to allow text to be transferred among the various clients while the images are being viewed.

Finally, additional lines of communication may be provided among the users of the multiple remote client locations so that they can discuss telephonically or even using a voice-over-Internet protocol-based system to confer in real time on the images that are being seen at each of the client stations.

Furthermore, the client in control of the image may relinquish control to a second client; the first client operating on a peer basis with the other clients in a secondary relationship thereafter.

In order to provide further analysis features, a linear measuring or tape measuring feature may be provided in order to determine the distance in microns, or the like, between a pair of points identified by pointing and clicking on portions of the image in order to determine the actual size of particular features shown in the specimen image. The size, of course, is computed on the basis of the magnification of the image being shown.

Other objects and advantages of the present invention will become obvious to one of ordinary skill in the art upon a perusal of the following specification and claims in light of the accompanying drawings.

BRIEF DESCRIPTION OF THE DRAWINGS

FIG. 2 is a screen view of a system embodying the present invention showing a low magnification image of a specimen on a microscope slide in one window, a high magnification image of a portion of the low magnification image selected by a region marker and a control window;

FIG. 3 is a view of a display screen of the apparatus embodying the present invention showing the control window a low magnification window having a plurality of high magnification micro image regions delineated therein and a high magnification window including one or more of the micro image regions;

FIG. 7A is a file listing such as would be seen under Windows 95 file manager showing the data files included in a data structure for a breast cancer specimen;

FIG. 7B is a file listing of a Java applet for controlling a data structure;

FIG. 8 is file listing such as would be seen under Windows 95 file manager showing the data files included in an alternate data structure for a breast cancer specimen;

FIGS. 9A and 9B are a block diagram of the apparatus embodying the present invention;

FIG. 18 is a block diagram of a remote networked system for distributing and accessing diagnostic images and data, i.e. virtual microscope slides, through a hypertext transport protocol based server directly or over a packet network;

FIGS. 36A through 36D are flow charts showing the operation of a server and a plurality of clients connected to the server for performing a virtual multi-headed microscope task.

DETAILED DESCRIPTION OF THE PREFERRED EMBODIMENT

Figure 1:
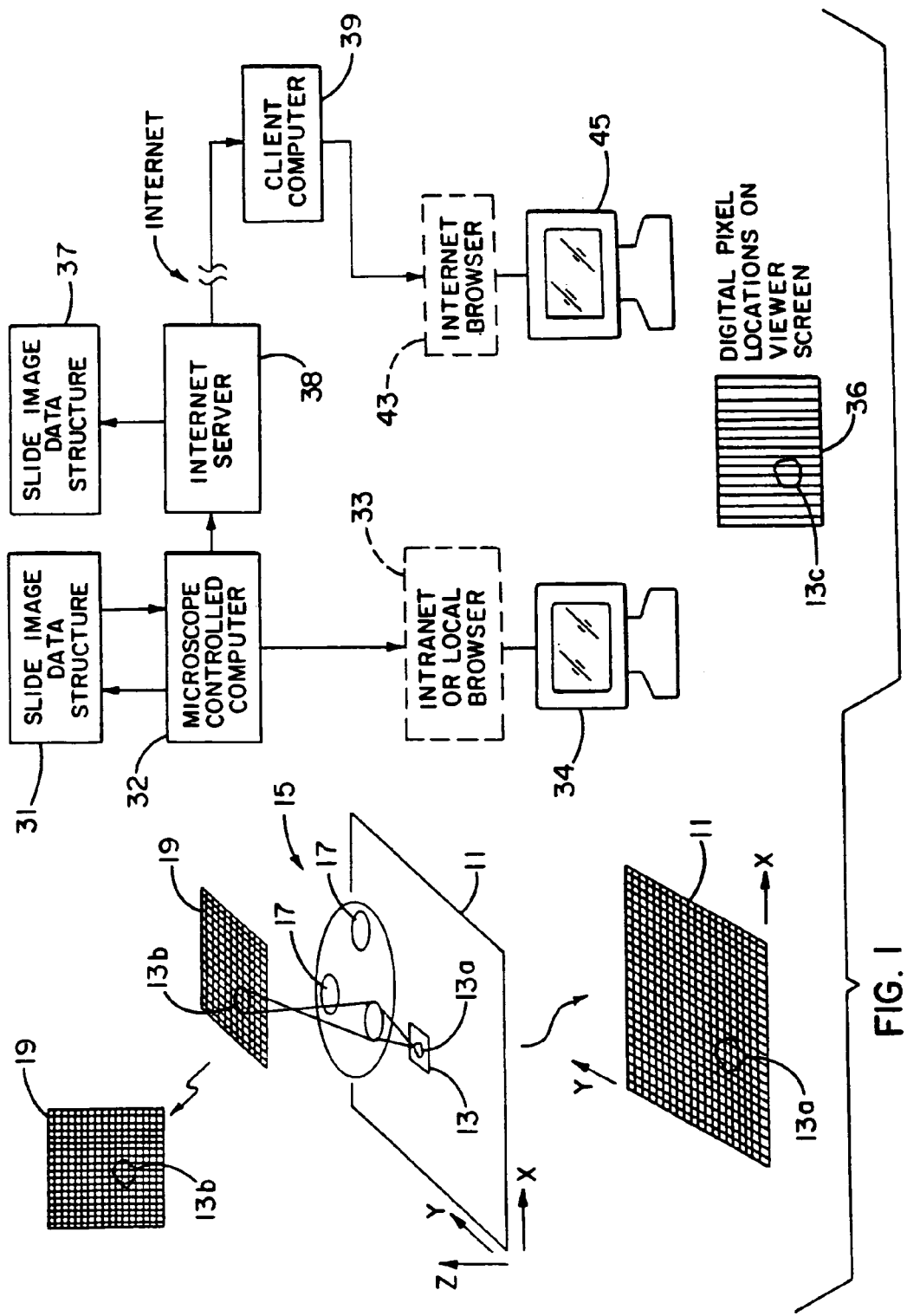
FIG. 1 is a block diagram of a system according to the invention for creating and transmitting locally, over an intranet or via the Internet data structures of an image of specimen on a microscope slide.

Referring now to the drawings and especially to FIG. 1, a system 10 according to the invention is shown therein for creating, and transmitting over an intranet or via the Internet a virtual microscope slide, i.e. interrelated data structures, which may or may not include display procedures, depicting at multiple resolutions, images of a specimen on a microscope slide. The system includes a microscope with a digital platform for supporting the microscope slide. Digital platform or stage 11 has been specially calibrated to include a large number of increments for locating portions of specimen images with high precision. After calibration and initial registration of stage 11 in the microscope setup, a microscope slide 13 or other substrate with a specimen 13a to be scanned is placed on stage 11.

For exemplary purposes, the creation of virtual microscope slide specimen according to the invention will be described with respect to a breast cancer specimen. The first step in creating a data structure according to the invention is to establish a macro image of the entire specimen (or that portion of the specimen desired to be stored as the macro image). The purpose for creating the macro or large area thumbnail image is to enable the viewer to see the entire specimen at once and to use the entire image to choose those significant portions thereon for viewing at greater magnification. In this example, the user has selected 1.25× as the magnification to display the entire breast cancer slide. Once specimen 13a has been placed on stage 11, rotating optical assembly 15 are rotated to select lens 17 which corresponds to the 1.25× magnification.

Figure 1B:
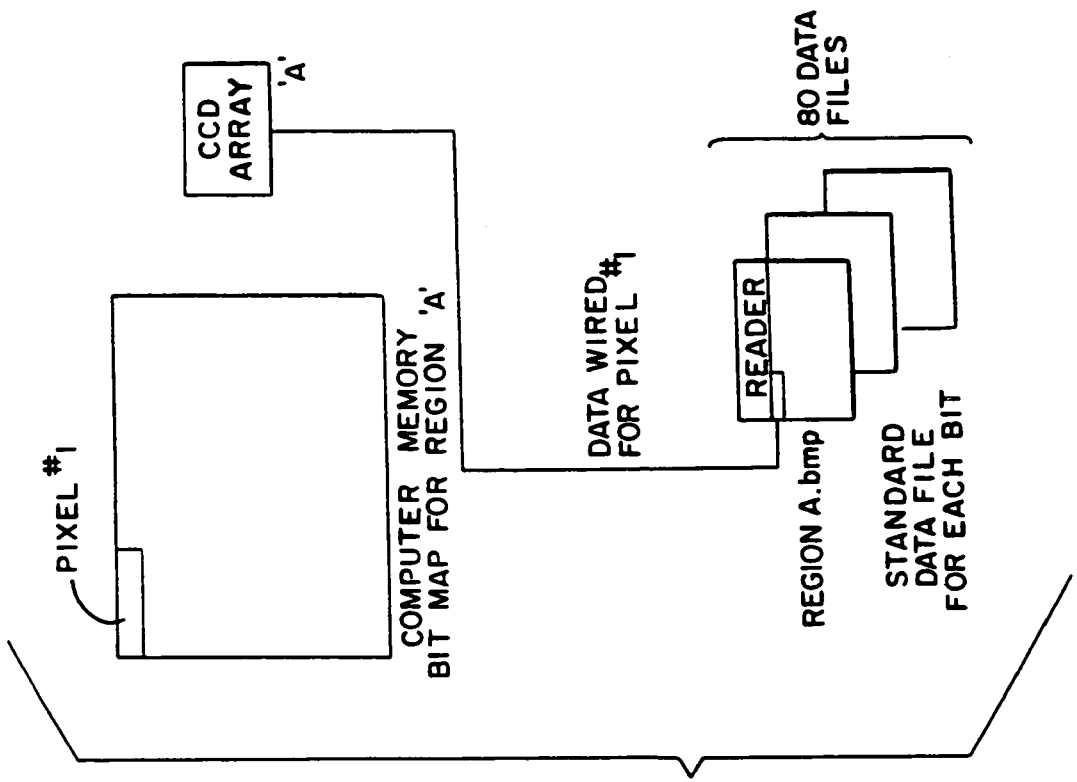
FIG. 1B is a representation of the detected signals of the individual pixel sensors in a CCD optical array after detecting a selected image area to tile and the referenced data files containing the information describing the detected signals.
Figure 1A:
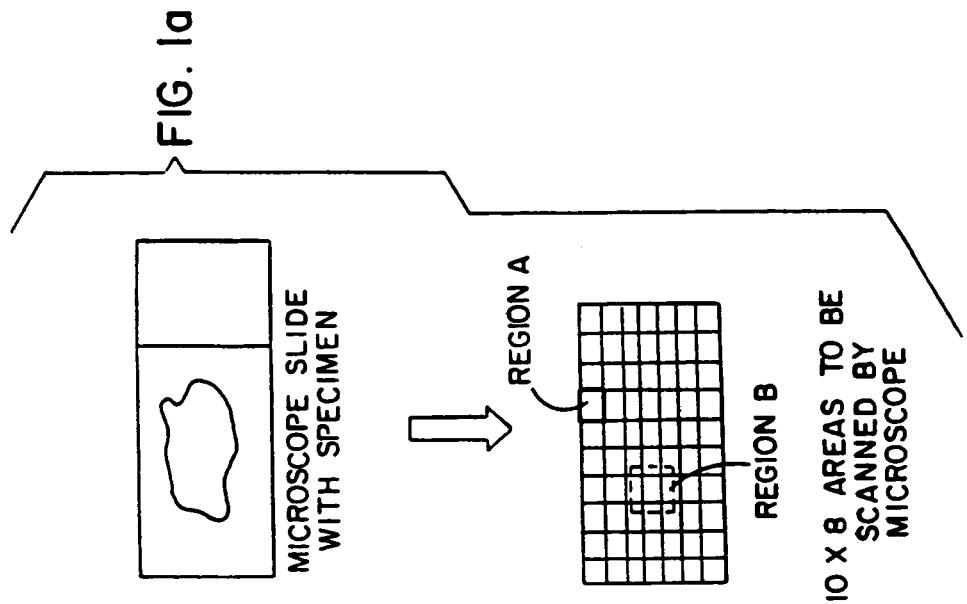
FIG. 1A is representation of a microscope slide which has been arbitrarily assigned to be scanned into eighty tiled images.

In accordance with the teachings of the prior patent application, the computer controlled microscope is moved to scan the entire image of specimen 13a. The focusing system is programmed to step through increments which detect/select only the high resolution center area of the field of view in order to avoid storing the blurred areas at the periphery of the field of view. In this example, the macro image will be stored in a 10 by 8 array, for a total of 80 contiguous image tiles, as shown in FIG. 1A.

A typical microscope slide is about 77 mm by 25 mm, where the usable area, without including the label, is about 57 mm by 25 m. Each of the 80 image segments is about 4.8 mm by 3.5 mm in dimension. This means each of the 80 image segments will be scanned separately and stored as a separate image tile.

The precision of the microscope systems is set up so that each step of the motor has a precision of 0.1 micron (micrometer). In this example, the microscope is set up to move 48,143 steps in the x direction and 35,800 steps in the Y direction at 1.25× magnification for each of the 80 image areas. At higher magnifications, the image areas to be scanned are considerably smaller, so the number of steps is corresponding smaller. For each of the 80 image areas, the microscope lens will detect only the high resolution center area of the field of view.

The optical image from the desired image area is then detected by an optical array sensor 19, which preferably is a CCD sensor array. In this embodiment each of the 80 scanned areas is sensed by the entire array 19, which includes 752 pixels by 480 pixels. The optical array sensor 19 sends electrical signals indicative of the detected image to a microscope-controlled computer 32. The computer 32 stores the scanned images, including the top left X-Y stage coordinates for each of the 80 individual areas of the microscope slide. Each of the 80 scanned image areas' pixel locations are stored in a bit-mapped file (i.e., a file which contains a map of the location of each bit in the area) which corresponds to the layout of the individual images thereon. Thus, all of the pixels from the image tile derived from region A on FIG. 1A, which is the seventh from the left and in the top row, are individually assigned unique locations in the computer memory's bit-mapped file (FIG. 6), and are also stored in the data structure image tile file as shown in FIG. 1B.

Each of the stored data image tiles is a standard image file with extension .bmp, and is of the order of one megabyte, i.e. each of the 752×480 pixels is stored as 3 bytes of red, green and blue image data (752×480×32=1,082,880 bytes). Since the location of each image tile is known according to the bitmap, the complete microscope image can be recreated by painting (displaying) each image tile in accordance with its grid location.

To display the resulting image, the computer 32 calculates the appropriate portion to be displayed from each image tile depending upon the relative size of the display screen. Since the stored image data is usually greater than the size of the typical monitor, the viewer must scroll through the image on the window to view it entirely. However, an optional compression algorithm can be used to compress the entire image into the viewing window. The X-Y coordinate information is used by the viewing and manipulation program to reconstruct the image tiles into a complete image of the specimen. The resulting image is larger, and with better resolution than would be achieved if optics technology were able to construct a single lens capable of viewing the entire specimen in one field of view. In this example, each of the 80 image tiles has digital resolution of 752×480 pixels, with corresponding optical resolution of approximate 0.2 microns at 40× to approximately 6.4 microns at 1.25×.

After the macro or thumbnail images are digitally scanned and stored with their X-Y coordinate information, the user then examines the macro image or original specimen for significant details. Typically, the user will highlight with a marking pen the areas to be viewed at higher magnification. The user then changes the magnification of optics system 15 to the desired higher magnification, moves the scanning system to bring the selected region into view. The computer 32 then repeats the scanning and image tile creation process for the selected region, but at higher magnification and with a new grid system to locate the scanned selected regions.

In the preferred embodiment example, the user has selected region B shown on FIG. 1A to perform a second view at a higher magnification. For example the user selects a 40× magnification. The computer 32 calculates the number of tiles needed to fill the selected area at 40× magnification and sets up a second grid.

It should be noted that region B crosses over several of the larger tiles in FIG. 1A. Because of the extremely precise 0.1 micron resolution of the instrument, locating such selected regions with high resolution is readily accomplished. As noted above, the computer 32 calculates the size of the image portion, in this case as an example, X=1500 and Y=1200 stepping increments. Each image portion at the 40× resolution is detected by the optical sensor array, 752 by 480 pixels. Each resulting data file is stored in a separate, high magnification mapped area of memory so that the computer can easily recall the location of region B, or any of its 200 individual image tiles, when requested by a user.

Once the user has completed selecting and having the computer controlled microscope system scan and store the digital images in image tiles, the computer 32 stores the mapped .bmp files along with their coordinate information and creates the slide image data structure 31 shown in FIG. 1. Slide image data structure 31 includes all of the bit-mapped image tile files at both magnifications (note that similarly, additional images could be stored at further magnifications, if desired), as well as X-Y coordinate information for the location of the various image tiles.

FIG. 7A is a file listing such as would be seen under a Windows 95 file manager showing the data files included in a data structure for a breast cancer specimen. Included in the file listing are FinalScan.ini and SlideScan.ini as well as sixty bit-mapped data files. Slidescan.ini is a listing of all the original bit-mapped (.bmp) files. The bit-mapped files represent the individual image tiles in the scan at, say, 1.25× magnifications. Slidescan.ini is set forth below in Table 1 and describes the X-Y coordinates for each image tile file. When the data structure is viewed by a control program, the program uses the X-Y coordinates to display all the image tiles contiguously.

TABLE 1

| Slidescan.ini |
|---|
| [Header] |
| x=278000 |
| y=142500 |
| lXStepSize=48143 |
| lYStepSize=35800 |
| iScannedCount=37 |
| [Ss1] |
| x=181714 |
| y=142500 |
| [Ss2] |
| x=133571 |
| y=142500 |
| [Ss3] |
| x=37285 |
| y=106700 |
| [Ss4] |
| x=85428 |
| y=106700 |
| [Ss5] |
| x=133571 |
| y=106700 |
| [Ss6] |
| x=181714 |
| y=106700 |
| [Ss7] |
| x=229857 |
| y=106700 |
| [Ss8] |
| x=229857 |
| y=70900 |
| [Ss9] |
| X=181714 |
| y=70900 |
| [Ss10] |
| x=133571 |
| y=70900 |
| [Ss11] |

TABLE 1-continued

| Slidescan.ini |
|---|
| x=85428 |
| y=70900 |
| [Ss12] |
| x=37285 |
| y=70900 |
| [Ss13] |
| x=−10858 |
| y=70900 |
| [Ss14] |
| x=−10858 |
| y=35100 |
| [Ss15] |
| x=37285 |
| y=35100 |
| [Ss16] |
| x=85428 |
| y=35100 |
| [Ss17] |
| x=133571 |
| y=35100 |
| [Ss18] |
| X=181714 |
| y=35100 |
| [Ss19] |
| x=229857 |
| y=35100 |
| [Ss20] |
| x=278000 |
| y=−700 |
| [Ss21] |
| x=229857 |
| y=−700 |
| [Ss22] |
| x=181714 |
| y=−700 |
| [Ss23] |
| x=133571 |
| y=−700 |
| [Ss24] |
| x=85428 |
| y=−700 |
| [Ss25] |
| x=37285 |
| y=−700 |
| [Ss26] |
| x=−10858 |
| y=−700 |
| [Ss27] |
| x=−10858 |
| y=−36500 |
| [Ss28] |
| x=37285 |
| y=−36500 |
| [Ss29] |
| x=85428 |
| y=−36500 |
| [Ss30] |
| x=133571 |
| y=−36500 |
| [Ss31] |
| x=181714 |
| y=−36500 |
| [Ss32] |
| x=229857 |
| y=−36500 |
| [Ss33] |
| x=278000 |
| y=−36500 |
| [Ss34] |
| x=278000 |
| y=−72300 |
| [Ss35] |
| x=229857 |
| y=−72300 |
| [Ss36] |
| x=181714 |
| y=−72300 |

TABLE 1-continued

Slidescan.ini

[Ss37]
x=133571
y=−72300

Table 2 is a listing of the file FinalScan.ini, which is a listing the X-Y coordinates of the high magnification image tiles scanned and stored.

TABLE 2

FinalScan.ini

[Header]
tPatientID=mda027
tAccession=
tOperatorID=jwb
tTimeOfScan=8/4/97 1:19:56 PM
lXStageRef=278000
lYStageRef=142500
iImageWidth=752
iImageHeight=480
lXStepSize=1590
lYStepSize=1190
lXOffset=−1900
lYOffset=−400
dMagnification=40
lAnalysisImageCount=105
lCalibrationImageCount=0
[Da0]
x=214532
y=65584
[Da1]
x=212996
y=65584
[Da2]
x=211460
y=65584
[Da3]
x=209924
y=65584
[Da4]
x=208388
y=65584
[Da5]
x=206852
y=65584
[Da6]
x=205316
y=65584
[Da7]
x=203780
y=65584
[Da8]
x=214532
y=64400
[Da9]
x=212996
y=64400
[Da10]
x=211460
y=64400
[Da11]
x=209924
y=64400
[Da12]
x=208388
y=64400
[Da13]
x=206852
y=64400
[Da14]
x=205316
y=64400

TABLE 2-continued

FinalScan.ini

[Da15]
x=203780
y=64400
[Da16]
x=214532
y=63216
[Da17]
x=212996
y=63216
[Da18]
x=211460
y=63216
[Da19]
x=209924
y=63216
[Da20]
x=208388
y=63216
[Da21]
x=206852
y=63216
[Da22]
x=205316
y=63216
[Da23]
x=203780
y=63216
[Da24]
x=214532
y=62032
[Da25]
x=212996
y=62032
[Da26]
x=211460
y=62032
[Da27]
x=209924
y=62032
[Da28]
x=208388
y=62032
[Da29]
x=206852
y=62032
[Da30]
x=205316
y=62032
[Da31]
x=203780
y=62032
[Da32]
x=214632
y=60848
[Da33]
x=212996
y=60848
[Da34]
x=211460
y=60848
[Da35]
x=209924
y=60848
[Da36]
x=208388
y=60848
[Da37]
x=206852
y=60848
[Da38]
x=205316
y=60848
[Da39]
x=203780
y=60848
[Da40]
x=214532

TABLE 2-continued

FinalScan.ini y=59664
[Da41]
x=212996
y=59664
[Da42]
x=211460
y=59664
[Da43]
x=209924
y=59664
[Da44]
x=208388
y=59664
[Da45]
x=206852
y=59664
[Da46]
x=205316
y=59664
[Da47]
x=203780
y=59664
[Da48]
x=214532
y=58480
[Da49]
x=212996
y=58480
[Da50]
x=211460
y=58480
[Da51]
x=209924
y=58480
[Da52]
x=208388
y=58480
[Da53]
x=206852
y=58480
[Da54]
x=205316
y=58480
[Da55]
x=203780
y=58480
[Da56]
x=180740
y=82160
[Da57]
x=179204
y=82160
[Da58]
x=177668
y=82160
[Da59]
x=176132
y=82160
[Da60]
x=174596
y=82160
[Da61]
x=173060
y=82160
[Da62]
x=171524
y=82160
[Da63]
x=180740
y=80976
[Da64]
x=179204
y=80976
[Da65]
x=177668
y=80976
[Da66]

TABLE 2-continued

FinalScan.ini x=176132
y=80976
[Da67]
x=174596
y=80976
[Da68]
x=173060
y=80976
[Da69]
X=171524
y=80976
[Da70]
x=180740
y=79792
[Da71]
x=179204
y=79792
[Da72]
x=177668
y=79792
[Da73]
x=176132
y=79792
[Da74]
x=174596
y=79792
[Da75]
x=173060
y=79792
[Da76]
x=171524
y=79792
[Da77]
x=180740
y=78608
[Da78]
x=179204
y=78608
[Da79]
x=177668
y=78608
[Da80]
x=176132
y=78608
[Da81]
x=174596
y=78608
[Da82]
x=173060
y=78608
[Da83]
x=171524
y=78608
[Da84]
x=180740
y=77424
[Da85]
x=179204
y=77424
[Da86]
x=177668
y=77424
[Da87]
X=176132
y=77424
[Da88]
x=174596
y=77424
[Da89]
x=173060
y=77424
[Da90]
x=171524
y=77424
[Da91]
x=180740
y=76240

TABLE 2-continued

FinalScan.ini

[Da92]
x=179204
y=76240
[Da93]
x=177668
y=76240
[Da94]
x=176132
y=76240
[Da95]
x=174596
y=76240
[Da96]
x=173060
y=76240
[Da97]
x=171524
y=76240
[Da98]
x=180740
y=75056
[Da99]
x=179204
y=75056
[Da100]
x=177668
y=75056
[Da101]
x=176132
y=75056
[Da102]
x=174596
y=75056
[Da103]
x=173060
y=75056
[Da104]
x=171524
y=75056

Computer 32 can also use the scanned image files to create a self-executing data structure. By compressing the .bmp images to .jpg and adding a dynamic, self-executing program which enables the user to view, reconstruct and manipulate the image tiles, the user can use the data structure as a virtual microscope slide of the original specimen. Preferably, the dynamic, self-executing program is a Java applet, such as shown on FIG. 7B.

Computer 32 can provide the slide image data structure 31 directly or via an intranet browser 33 to local viewer 34, or via an Internet server 38. Slide image data structure 37 is shown as being directly accessible from Internet server 38. Alternatively, a user can download the slide image data structure on his own computer 39, use an internet browser 43 and view the reconstructed images. Another alternative is for computer 32 to store the slide image data structure on a CD-ROM, Jazz drive or other storage medium.

To view slide image data structure 31 or 37, the user, who for example, has acquired the data structure via a CD-ROM, first installs the CD-ROM in the CD-ROM drive of his computer. Then the user opens up a browser or other applications program which can read the Java applet installed on the CD-ROM with the image tiles. Note that in some instances no separate browser program may be required. In some case, the CD-ROM may include the complete applications program for viewing, reconstructing and manipulating the image tiles. In the instant example, the user will then select the icon or file listing for the slide image data structure and the control program will display the data files.

Figure 4:
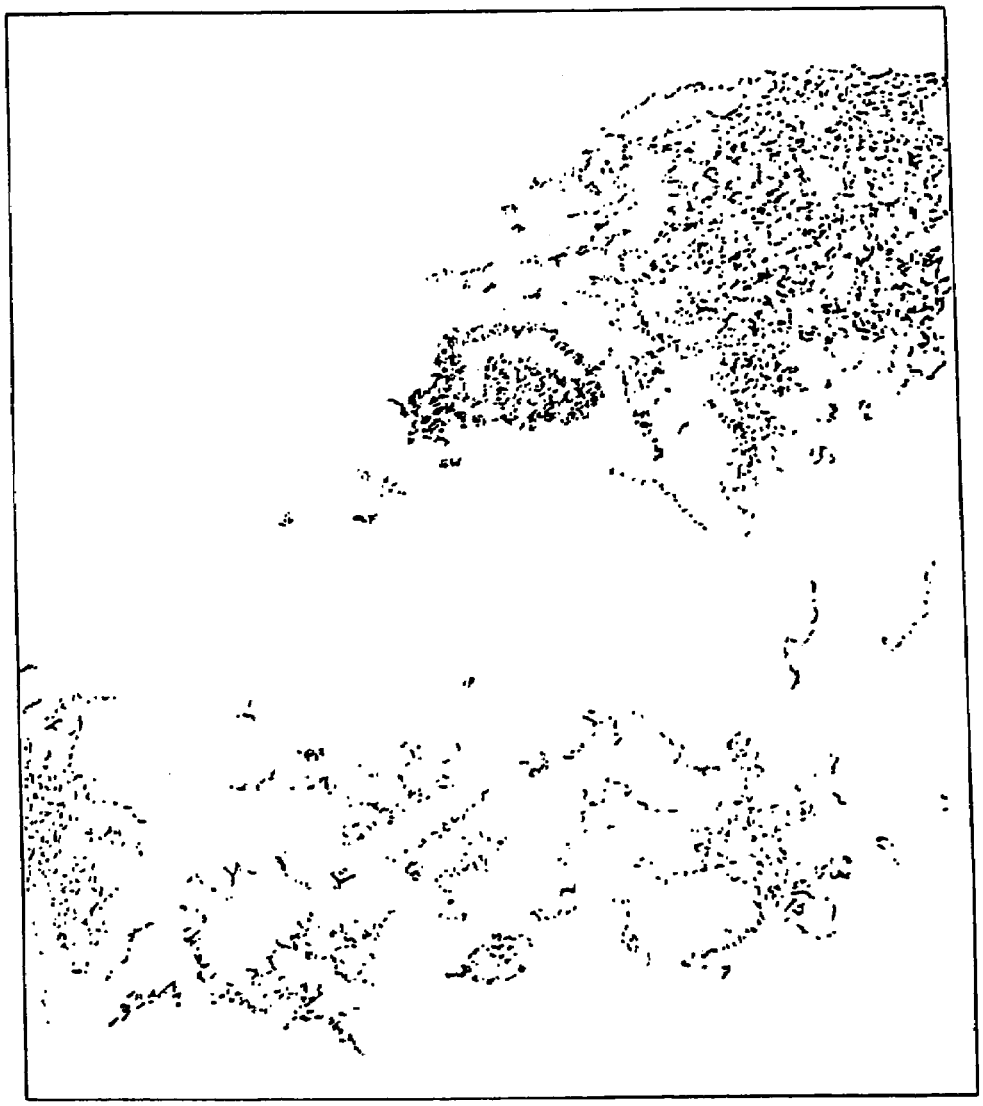
FIG. 4 is a view of a macro image of an actual breast cancer specimen displayed at 1.25× as seen on a computer monitor.
Figure 5:
FIG. 5 is a view of the grid portion of FIG. 4 outlining a region of interest selected by a pathologist displayed at 40× magnification.

FIG. 2 is a screen view of a system embodying the present invention showing a low magnification image 24 of a specimen on a microscope slide in one window, a high magnification image 26 of a portion of the low magnification image selected by a region marker 30 and a control window 28. FIG. 3 is a view of a display screen of the apparatus embodying the present invention showing the control window 28, a low magnification window 24 having a plurality of high magnification micro image regions 310 delineated therein and a high magnification window 26 including one or more of the micro image regions 310, 314, 316. FIG. 4 is a view of a macro image of an actual breast cancer specimen displayed at 1.25× as seen on a computer monitor. FIG. 5 is a view of the grid portion of FIG. 4 outlining a region of interest selected by a pathologist displayed at 40× magnification.

Recall that region A in FIG. 1A was about 4.8 mm by 3.5 mm. This area creates 752 by 480 pixels of sensed data, or 360,930 pixels of information. Each pixel sends information about its location and the image it sensed to the computer. The computer stores this information in a series of data files (typically .bmp format, but .tif or .gif could also be used). Thus, it can be seen that several more pixels of sensed data are available for viewing on a computer monitor operating at 640 by 480. To view the entire image, the user must scroll through the image tiles. However, scrolling need not be done on a tile, by tile basis. Rather, the user scrolls by pointing to a pixel on the monitor.

Figure 6:
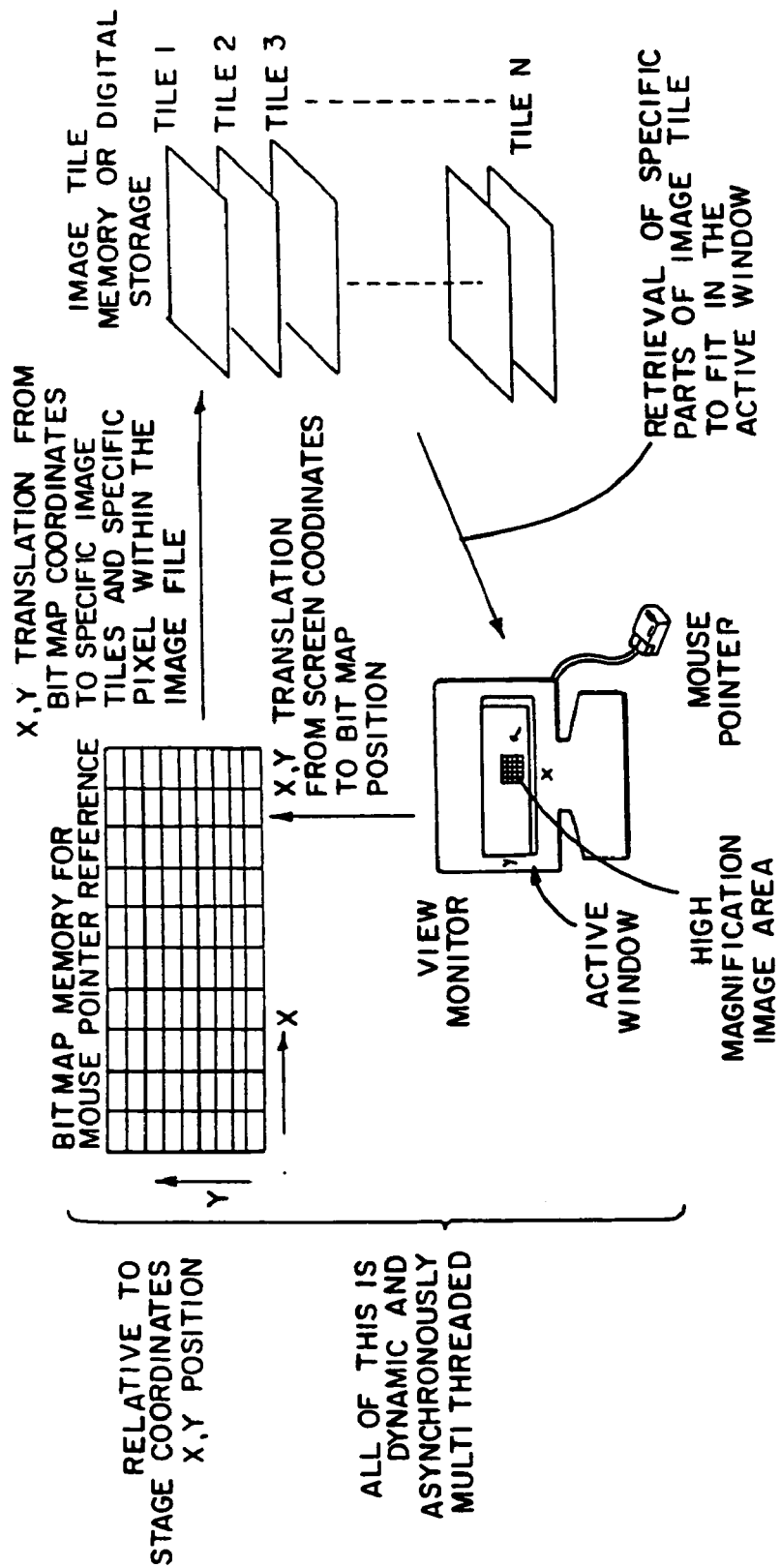
FIG. 6 is a block diagram of the steps in the mapping of the scanned image from the optical sensor array to computer bit map in memory to the display on a user's monitor.

FIG. 6 is a block diagram showing how the control program locates and scrolls through the stored image tiles. Using the example from FIG. 1a, a complete data structure has been created. When the user loads the data structure (of the microscope slide) into his personal computer or views it from an Internet browser, the control program recreates a bit map of the stored data. The bit map of the entire slide is shown in FIG. 6. Image tile A is also high-lighted. This bit map enables a user to point to or otherwise reference a location on the slide.

The X-Y coordinate information specified in the data structure enables X-Y translation of the specific image tiles and specific pixels within the image tile. When the control program first loads the image, because this image file is so large, only a small number of the available tiles are displayed in the active window on the user's monitor. The user uses his mouse or pointing device to scroll through the active window to view the entire macro image. The X-Y coordinate information selected by the mouse translates into specific image tiles or portions therein. The computer takes the mouse pointer information and retrieves the image data from the series of stored tile images and displays them on the monitor for viewing the by user.

Because of the large amount of CCD pixel information stored, actual CCD pixel information can be recreated in the viewing window. The entire system operates in a loop, where the user inputs a mouse location, the computer translates the mouse location from the screen coordinates (screen pixels) to the X-Y coordinates on the bit map.

Similarly, the user may select the high magnification data images. These are outlined by a dark grid, indicating the areas stored. The user operates the mouse in the same manner as described above. The control program locates the stored X-Y coordinates and retrieves the selected parts of the image, CCD stored pixel by CCD stored pixel.

As mentioned above, to save storage space, computer 32 can perform a data compression on each of the image tile files. A preferred data compression is JPEG, which is readily transferred and recognized by most Internet browser programs. Also, JPEG allows flexibility in the amount of data to be compressed, from 20 to 80 percent. FIG. 8 is file listing such as would be seen under Windows 95 file manager showing the data files included in an alternate data structure, one in which the data files have been compressed or converted to JPEG (.jpg) format for a breast cancer specimen. The file index.html (shown in Table 3) is the listing which contains the X-Y coordinate information for these data files. This is the information that is read by the dynamic, self-executing program for viewing, reconstructing and manipulating the image tiles into the macro and micro views.

TABLE 3 index.html

```
<HTML>
<TITLE>
DCIS_027 - Web Slide
</TITLE>
<BODY>
<APPLET CODE=WebSlide/BliWebSlide.class NAME=DCIS_027
WIDTH=3384 HEIGHT=960 HSPACE=0 VSPACE=0 ALIGN=Middle>
<PARAM NAME = "tPatientID" VALUE = "mda027">
<PARAM NAME = "tAccession" VALUE = "">
<PARAM NAME = "tOperatorID" VALUE = "jwb">
<PARAM NAME = "tTimeOfScan" VALUE = "8/4/97 1:19:56 PM">
<PARAM NAME = "lXStageRef" VALUE = "278000">
<PARAM NAME = "lYStageRef" VALUE = "142500">
<PARAM NAME = "iImageWidth" VALUE = "752">
<PARAM NAME = "iImageHeight" VALUE = "480">
<PARAM NAME = "lXStepSize" VALUE = "1590">
<PARAM NAME = "lYStepSize" VALUE = "1190">
<PARAM NAME = "lXOffset" VALUE = "-1900">
<PARAM NAME = "lYOffset" VALUE = "-400">
<PARAM NAME = "dMagnification" VALUE = "40">
<PARAM NAME = "iImageCount" VALUE = "105">
<PARAM NAME = "lXSsStepSize" VALUE = "48143">
<PARAM NAME = "lYSsStepSize" VALUE = "35800">
<PARAM NAME = "iScannedCount" VALUE = "37">
<PARAM NAME = "lStartX" VALUE = "278000">
<PARAM NAME = "lStartY" VALUE = "142500">
<PARAM NAME = "Ss1_X" VALUE = "181714">
<PARAM NAME = "Ss1_Y" VALUE = "142500">
<PARAM NAME = "Ss2_X" VALUE = "133571">
<PARAM NAME = "Ss2_Y" VALUE = "142500">
<PARAM NAME = "Ss3_X" VALUE = "37285">
<PARAM NAME = "Ss3_Y" VALUE = "106700">
<PARAM NAME = "Ss4_X" VALUE = "85428">
<PARAM NAME = "Ss4_Y" VALUE = "106700">
<PARAM NAME = "Ss5_X" VALUE = "133571">
<PARAM NAME = "Ss5_Y" VALUE = "106700">
<PARAM NAME = "Ss6_X" VALUE = "181714">
<PARAM NAME = "Ss6_Y" VALUE = "106700">
<PARAM NAME = "Ss7_X" VALUE = "229857">
<PARAM NAME = "Ss7_Y" VALUE = "106700">
<PARAM NAME = "Ss8_X" VALUE = "229857">
<PARAM NAME = "Ss8_Y" VALUE = "70900">
<PARAM NAME = "Ss9_X" VALUE = "181714">
<PARAM NAME = "Ss9_Y" VALUE = "70900">
<PARAM NAME = "Ss10_X" VALUE = "133571">
<PARAM NAME = "Ss10_Y" VALUE = "70900">
<PARAM NAME = "Ss11_X" VALUE = "85428">
<PARAM NAME = "Ss11_Y" VALUE = "70900">
<PARAM NAME = "Ss12_X" VALUE = "37285">
<PARAM NAME = "Ss12_Y" VALUE = "70900">
<PARAM NAME = "Ss13_X" VALUE = "-10858">
<PARAM NAME = "Ss13_Y" VALUE = "70900">
<PARAM NAME = "Ss14_X" VALUE = "-10858">
<PARAM NAME = "Ss14_Y" VALUE = "35100">
<PARAM NAME = "Ss15_X" VALUE = "37285">
<PARAM NAME = "Ss15_Y" VALUE = "35100">
<PARAM NAME = "Ss16_X" VALUE = "85428">
<PARAM NAME = "Ss16_Y" VALUE = "35100">
<PARAM NAME = "Ss17_X" VALUE = "133571">
<PARAM NAME = "Ss17_Y" VALUE = "35100">
<PARAM NAME = "Ss18_X" VALUE = "181714">
<PARAM NAME = "Ss18_Y" VALUE = "35100">
<PARAM NAME = "Ss19_X" VALUE = "229857">
```

TABLE 3-continued index.html

```
<PARAM NAME = "Ss19_Y" VALUE = "35100">
<PARAM NAME = "Ss20_X" VALUE = "278000">
<PARAM NAME = "Ss20_Y" VALUE = "-700">
<PARAM NAME = "Ss21_X" VALUE = "229857">
<PARAM NAME = "Ss21_Y" VALUE = "-700">
<PARAM NAME = "Ss22_X" VALUE = "181714">
<PARAM NAME = "Ss22_Y" VALUE = "-700">
<PARAM NAME = "Ss23_X" VALUE = "133571">
<PARAM NAME = "Ss23_Y" VALUE = "-700">
<PARAM NAME = "Ss24_X" VALUE = "85428">
<PARAM NAME = "Ss24_Y" VALUE = "-700">
<PARAM NAME = "Ss25_X" VALUE = "37285">
<PARAM NAME = "Ss25_Y" VALUE = "-700">
<PARAM NAME = "Ss26_X" VALUE = "-10858">
<PARAM NAME = "Ss26_Y" VALUE = "-700">
<PARAM NAME = "Ss27_X" VALUE = "-10858">
<PARAM NAME = "Ss27_Y" VALUE = "-36500">
<PARAM NAME = "Ss28_X" VALUE = "37285">
<PARAM NAME = "Ss28_Y" VALUE = "-36500">
<PARAM NAME = "Ss29_X" VALUE = "85428">
<PARAM NAME = "Ss29_Y" VALUE = "-36500">
<PARAM NAME = "Ss30_X" VALUE = "133571">
<PARAM NAME = "Ss30_Y" VALUE = "-36500">
<PARAM NAME = "Ss31_X" VALUE = "181714">
<PARAM NAME = "Ss31_Y" VALUE = "-36500">
<PARAM NAME = "Ss32_X" VALUE = "229857">
<PARAM NAME = "Ss32_Y" VALUE = "-36500">
<PARAM NAME = "Ss33_X" VALUE = "278000">
<PARAM NAME = "Ss33_Y" VALUE = "-36500">
<PARAM NAME = "Ss34_X" VALUE = "278000">
<PARAM NAME = "Ss34_Y" VALUE = "-72300">
<PARAM NAME = "Ss35_X" VALUE = "229857">
<PARAM NAME = "Ss35_Y" VALUE = "-72300">
<PARAM NAME = "Ss36_X" VALUE = "181714">
<PARAM NAME = "Ss36_Y" VALUE = "-72300">
<PARAM NAME = "Ss37_X" VALUE = "133571">
<PARAM NAME = "Ss37_Y" VALUE = "-72300">
<PARAM NAME = "Da0_X" VALUE = "214532">
<PARAM NAME = "Da0_Y" VALUE = "65584">
<PARAM NAME = "Da1_X" VALUE = "212996">
<PARAM NAME = "Da1_Y" VALUE = "65584">
<PARAM NAME = "Da2_X" VALUE = "211460">
<PARAM NAME = "Da2_Y" VALUE = "65584">
<PARAM NAME = "Da3_X" VALUE = "209924">
<PARAM NAME = "Da3_Y" VALUE = "65584">
<PARAM NAME = "Da4_X" VALUE = "208388">
<PARAM NAME = "Da4_Y" VALUE = "65584">
<PARAM NAME = "Da5_X" VALUE = "206852">
<PARAM NAME = "Da5_Y" VALUE = "65584">
<PARAM NAME = "Da6_X" VALUE = "205316">
<PARAM NAME = "Da6_Y" VALUE = "65584">
<PARAM NAME = "Da7_X" VALUE = "203780">
<PARAM NAME = "Da7_Y" VALUE = "65584">
<PARAM NAME = "Da8_X" VALUE = "214532">
<PARAM NAME = "Da8_Y" VALUE = "64400">
<PARAM NAME = "Da9_X" VALUE = "212996">
<PARAM NAME = "Da9_Y" VALUE = "64400">
<PARAM NAME = "Da10_X" VALUE = "211460">
<PARAM NAME = "Da10_Y" VALUE = "64400">
<PARAM NAME = "Da11_X" VALUE = "209924">
<PARAM NAME = "Da11_Y" VALUE = "64400">
<PARAM NAME = "Da12_X" VALUE = "208388">
<PARAM NAME = "Da12_Y" VALUE = "64400">
<PARAM NAME = "Da13_X" VALUE = "206852">
<PARAM NAME = "Da13_Y" VALUE = "64400">
<PARAM NAME = "Da14_X" VALUE = "205316">
<PARAM NAME = "Da14_Y" VALUE = "64400">
<PARAM NAME = "Da15_X" VALUE = "203780">
<PARAM NAME = "Da15_Y" VALUE = "64400">
<PARAM NAME = "Da16_X" VALUE = "214532">
<PARAM NAME = "Da16_Y" VALUE = "63216">
<PARAM NAME = "Da17_X" VALUE = "212996">
<PARAM NAME = "Da17_Y" VALUE = "63216">
<PARAM NAME = "Da18_X" VALUE = "211460">
<PARAM NAME = "Da18_Y" VALUE = "63216">
<PARAM NAME = "Da19_X" VALUE = "209924">
<PARAM NAME = "Da19_Y" VALUE = "63216">
```

TABLE 3-continued index.html

| | |
|---|---|
| <PARAM NAME = "Da20_X" VALUE = "208388"> | <PARAM NAME = "Da59_X" VALUE = "176132"> |
| <PARAM NAME = "Da20_Y" VALUE = "63216"> | <PARAM NAME = "Da59_Y" VALUE = "82160"> |
| <PARAM NAME = "Da21_X" VALUE = "206852"> | <PARAM NAME = "Da60_X" VALUE = "174596"> |
| <PARAM NAME = "Da21_Y" VALUE = "63216"> | <PARAM NAME = "Da60_Y" VALUE = "82160"> |
| <PARAM NAME = "Da22_X" VALUE = "205316"> | <PARAM NAME = "Da61_X" VALUE = "173060"> |
| <PARAM NAME = "Da22_Y" VALUE = "63216"> | <PARAM NAME = "Da61_Y" VALUE = "82160"> |
| <PARAM NAME = "Da23_X" VALUE = "203780"> | <PARAM NAME = "Da62_X" VALUE = "171524"> |
| <PARAM NAME = "Da23_Y" VALUE = "63216"> | <PARAM NAME = "Da62_Y" VALUE = "82160"> |
| <PARAM NAME = "Da24_X" VALUE = "214532"> | <PARAM NAME = "Da63_X" VALUE = "180740"> |
| <PARAM NAME = "Da24_Y" VALUE = "62032"> | <PARAM NAME = "Da63_Y" VALUE = "80976"> |
| <PARAM NAME = "Da25_X" VALUE = "212996"> | <PARAM NAME = "Da64_X" VALUE = "179204"> |
| <PARAM NAME = "Da25_Y" VALUE = "62032"> | <PARAM NAME = "Da64_Y" VALUE = "80976"> |
| <PARAM NAME = "Da26_X" VALUE = "211460"> | <PARAM NAME = "Da65_X" VALUE = "177668"> |
| <PARAM NAME = "Da26_Y" VALUE = "62032"> | <PARAM NAME = "Da65_Y" VALUE = "80976"> |
| <PARAM NAME = "Da27_X" VALUE = "209924"> | <PARAM NAME = "Da66_X" VALUE = "176132"> |
| <PARAM NAME = "Da27_Y" VALUE = "62032"> | <PARAM NAME = "Da66_Y" VALUE = "80976"> |
| <PARAM NAME = "Da28_X" VALUE = "208388"> | <PARAM NAME = "Da67_X" VALUE = "174596"> |
| <PARAM NAME = "Da28_Y" VALUE = "62032"> | <PARAM NAME = "Da67_Y" VALUE = "80976"> |
| <PARAM NAME = "Da29_X" VALUE = "206852"> | <PARAM NAME = "Da68_X" VALUE = "173060"> |
| <PARAM NAME = "Da29_Y" VALUE = "62032"> | <PARAM NAME = "Da68_Y" VALUE = "80976"> |
| <PARAM NAME = "Da30_X" VALUE = "205316"> | <PARAM NAME = "Da69_X" VALUE = "171524"> |
| <PARAM NAME = "Da30_Y" VALUE = "62032"> | <PARAM NAME = "Da69_Y" VALUE = "80976"> |
| <PARAM NAME = "Da31_X" VALUE = "203780"> | <PARAM NAME = "Da70_X" VALUE = "180740"> |
| <PARAM NAME = "Da32 _X" VALUE = "214532"> | <PARAM NAME = "Da70_Y" VALUE = "79792"> |
| <PARAM NAME = "Da32_Y" VALUE = "60848"> | <PARAM NAME = "Da71_X" VALUE = "179204"> |
| <PARAM NAME = "Da33_X" VALUE = "212996"> | <PARAM NAME = "Da71_Y" VALUE = "79792"> |
| <PARAM NAME = "Da33_Y" VALUE = "60848"> | <PARAM NAME = "Da72_X" VALUE = "177668"> |
| <PARAM NAME = "Da34_X" VALUE = "211460"> | <PARAM NAME = "Da72_Y" VALUE = "79792"> |
| <PARAM NAME = "Da34_Y" VALUE = "60848"> | <PARAM NAME = "Da73_X" VALUE = "176132"> |
| <PARAM NAME = "Da35_X" VALUE = "209924"> | <PARAM NAME = "Da73_Y" VALUE = "79792"> |
| <PARAM NAME = "Da35_Y" VALUE = "60848"> | <PARAM NAME = "Da74_X" VALUE = "174596"> |
| <PARAM NAME = "Da36_X" VALUE = "208388"> | <PARAM NAME = "Da74_Y" VALUE = "79792"> |
| <PARAM NAME = "Da36_Y" VALUE = "60848"> | <PARAM NAME = "Da75_X" VALUE = "173060"> |
| <PARAM NAME = "Da37_X" VALUE = "206852"> | <PARAM NAME = "Da75_Y" VALUE = "79792"> |
| <PARAM NAME = "Da37_Y" VALUE = "60848"> | <PARAM NAME = "Da76_X" VALUE = "171524"> |
| <PARAM NAME = "Da38_X" VALUE = "205316"> | <PARAM NAME = "Da76_Y" VALUE = "79792"> |
| <PARAM NAME = "Da38_Y" VALUE = "60848"> | <PARAM NAME = "Da77_X" VALUE = "180740"> |
| <PARAM NAME = "Da39_X" VALUE = "203780"> | <PARAM NAME = "Da77_Y" VALUE = "78608"> |
| <PARAM NAME = "Da39_Y" VALUE = "60848"> | <PARAM NAME = "Da78_X" VALUE = "179204"> |
| <PARAM NAME = "Da40_X" VALUE = "214532"> | <PARAM NAME = "Da78_Y" VALUE = "78608"> |
| <PARAM NAME = "Da40_Y" VALUE = "59664"> | <PARAM NAME = "Da79_X" VALUE = "177668"> |
| <PARAM NAME = "Da41_X" VALUE = "212996"> | <PARAM NAME = "Da79_Y" VALUE = "78608"> |
| <PARAM NAME = "Da41_Y" VALUE = "59664"> | <PARAM NAME = "Da80_X" VALUE = "176132"> |
| <PARAM NAME = "Da42_X" VALUE = "211460"> | <PARAM NAME = "Da80_Y" VALUE = "78608"> |
| <PARAM NAME = "Da42_Y" VALUE = "59664"> | <PARAM NAME = "Da81_X" VALUE = "174596"> |
| <PARAM NAME = "Da43_X" VALUE = "209924"> | <PARAM NAME = "Da81_Y" VALUE = "78608"> |
| <PARAM NAME = "Da43_Y" VALUE = "59664"> | <PARAM NAME = "Da82_X" VALUE = "173060"> |
| <PARAM NAME = "Da44_X" VALUE = "208388"> | <PARAM NAME = "Da82_Y" VALUE = "78608"> |
| <PARAM NAME = "Da44_Y" VALUE = "59664"> | <PARAM NAME = "Da83_X" VALUE = "171524"> |
| <PARAM NAME = "Da45_X" VALUE = "206852"> | <PARAM NAME = "Da83_Y" VALUE = "78608"> |
| <PARAM NAME = "Da45_Y" VALUE = "59664"> | <PARAM NAME = "Da84_X" VALUE = "180740"> |
| <PARAM NAME = "Da46_X" VALUE = "205316"> | <PARAM NAME = "Da84_Y" VALUE = "77424"> |
| <PARAM NAME = "Da46_Y" VALUE = "59664"> | <PARAM NAME = "Da85_X" VALUE = "179204"> |
| <PARAM NAME = "Da47_X" VALUE = "203780"> | <PARAM NAME = "Da85_Y" VALUE = "77424"> |
| <PARAM NAME = "Da47_Y" VALUE = "59664"> | <PARAM NAME = "Da86_X" VALUE = "177668"> |
| <PARAM NAME = "Da48_X" VALUE = "214532"> | <PARAM NAME = "Da86_Y" VALUE = "77424"> |
| <PARAM NAME = "Da48_Y" VALUE = "58480"> | <PARAM NAME = "Da87_X" VALUE = "176132"> |
| <PARAM NAME = "Da49_X" VALUE = "212996"> | <PARAM NAME = "Da87_Y" VALUE = "77424"> |
| <PARAM NAME = "Da49_Y" VALUE = "58480"> | <PARAM NAME = "Da88_X" VALUE = "174596"> |
| <PARAM NAME = "Da50_X" VALUE = "211460"> | <PARAM NAME = "Da88_Y" VALUE = "77424"> |
| <PARAM NAME = "Da50_Y" VALUE = "58480"> | <PARAM NAME = "Da89_X" VALUE = "173060"> |
| <PARAM NAME = "Da51_X" VALUE = "209924"> | <PARAM NAME = "Da89_Y" VALUE = "77424"> |
| <PARAM NAME = "Da51_Y" VALUE = "58480"> | <PARAM NAME = "Da90_X" VALUE = "171524"> |
| <PARAM NAME = "Da52_X" VALUE = "208388"> | <PARAM NAME = "Da90_Y" VALUE = "77424"> |
| <PARAM NAME = "Da52_Y" VALUE = "58480"> | <PARAM NAME = "Da91_X" VALUE = "180740"> |
| <PARAM NAME = "Da53_X" VALUE = "206852"> | <PARAM NAME = "Da91_Y" VALUE = "76240"> |
| <PARAM NAME = "Da53_Y" VALUE = "58480"> | <PARAM NAME = "Da92_X" VALUE = "179204"> |
| <PARAM NAME = "Da54_X" VALUE = "205316"> | <PARAM NAME = "Da92_Y" VALUE = "76240"> |
| <PARAM NAME = "Da54_Y" VALUE = "58480"> | <PARAM NAME = "Da93_X" VALUE = "177668"> |
| <PARAM NAME = "Da55_X" VALUE = "203780"> | <PARAM NAME = "Da93_Y" VALUE = "76240"> |
| <PARAM NAME = "Da55_Y" VALUE = "58480"> | <PARAM NAME = "Da94_X" VALUE = "176132"> |
| <PARAM NAME = "Da56_X" VALUE = "180740"> | <PARAM NAME = "Da94_Y" VALUE = "76240"> |
| <PARAM NAME = "Da56_Y" VALUE = "82160"> | <PARAM NAME = "Da95_X" VALUE = "174596"> |
| <PARAM NAME = "Da57_X" VALUE = "179204"> | <PARAM NAME = "Da95_Y" VALUE = "76240"> |
| <PARAM NAME = "Da57_Y" VALUE = "82160"> | <PARAM NAME = "Da96_X" VALUE = "173060"> |
| <PARAM NAME = "Da58_X" VALUE = "177668"> | <PARAM NAME = "Da96_Y" VALUE = "76240"> |
| <PARAM NAME = "Da58_Y" VALUE = "82160"> | <PARAM NAME = "Da97_X" VALUE = "171524"> |

TABLE 3-continued index.html

```
<PARAM NAME = "Da97_Y" VALUE = "76240">
<PARAM NAME = "Da98_X" VALUE = "180740">
<PARAM NAME = "Da98_Y" VALUE = "75056">
<PARAM NAME = "Da99_X" VALUE = "179204">
<PARAM NAME = "Da99_Y" VALUE = "75056">
<PARAM NAME = "Da100_X" VALUE = "177668">
<PARAM NAME = "Da100_Y" VALUE = "75056">
<PARAM NAME = "Da101_X" VALUE = "176132">
<PARAM NAME = "Da101_Y" VALUE = "75056">
<PARAM NAME = "Da102_X" VALUE = "174596">
<PARAM NAME = "Da102_Y" VALUE = "75056">
<PARAM NAME = "Da103_X" VALUE = "173060">
<PARAM NAME = "Da103_Y" VALUE = "75056">
<PARAM NAME = "Da104_X" VALUE = "171524">
<PARAM NAME = "Da104_Y" VALUE = "75056">
</APPLET>
</BODY>
</HTML>
```

Figure 9B:
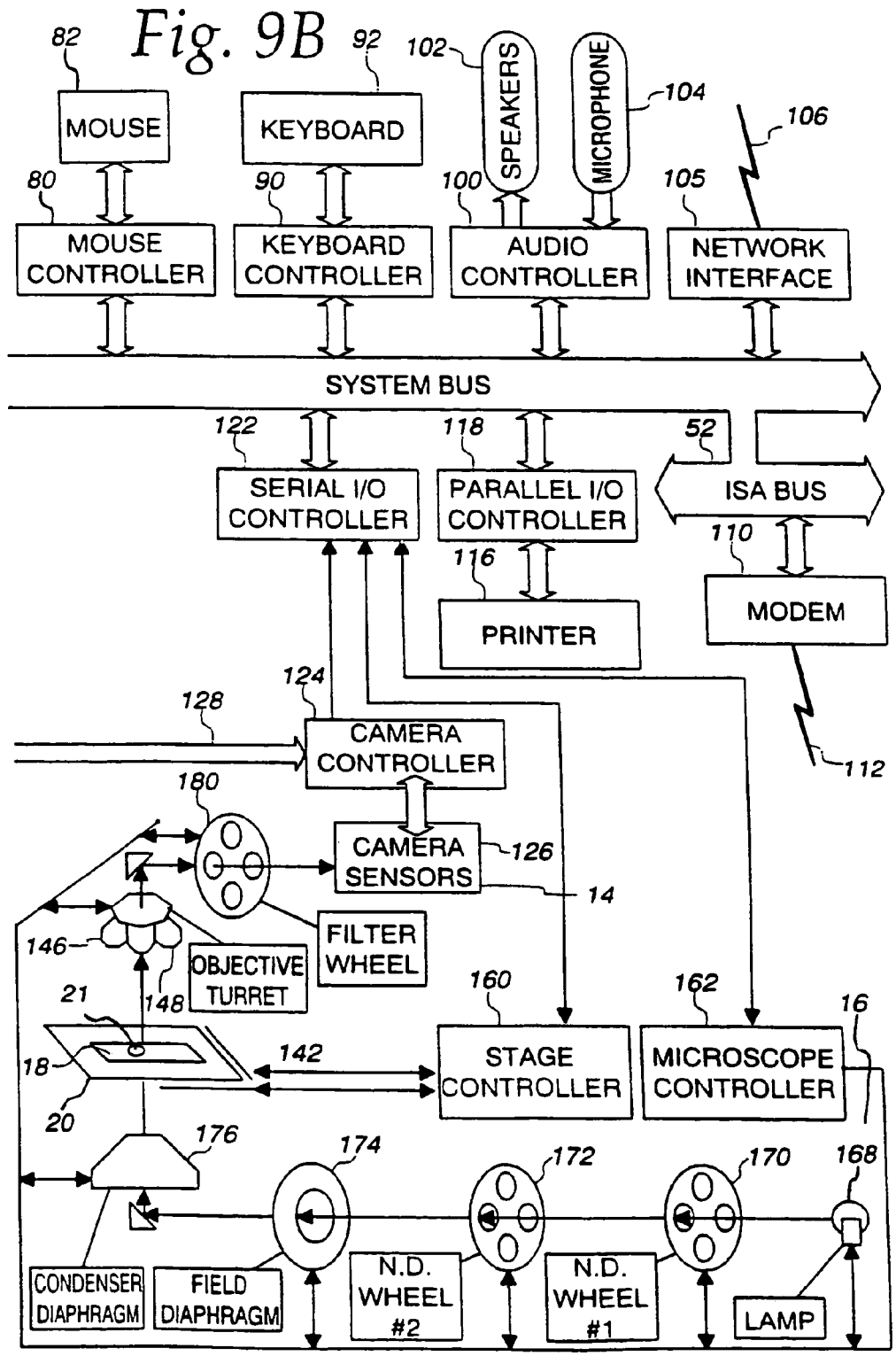
Figure 10:
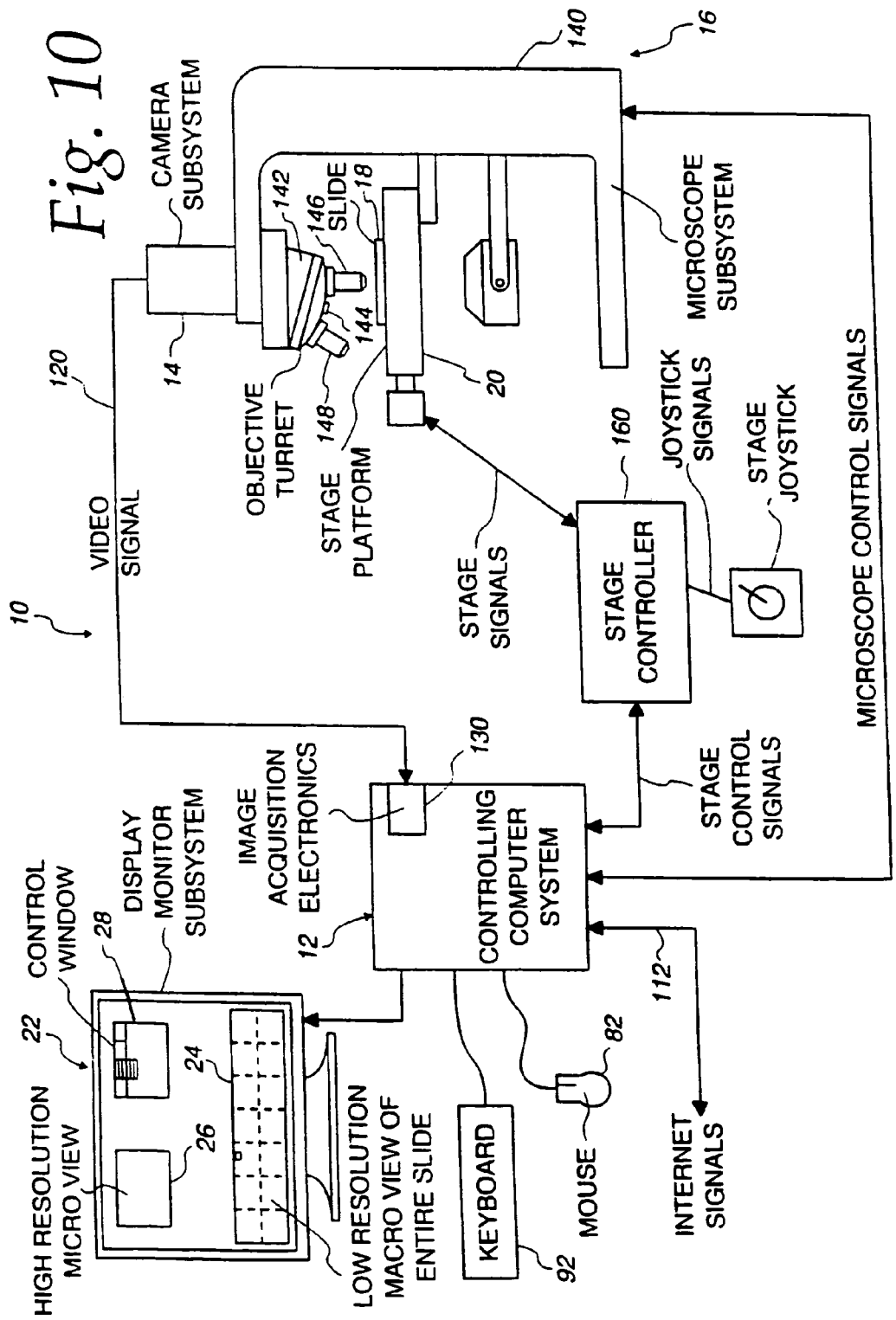
FIG. 10 is a block diagram of a portion of the apparatus shown in FIG. 9 showing details of a mechanical arrangement of a microscope.
Figure 11:
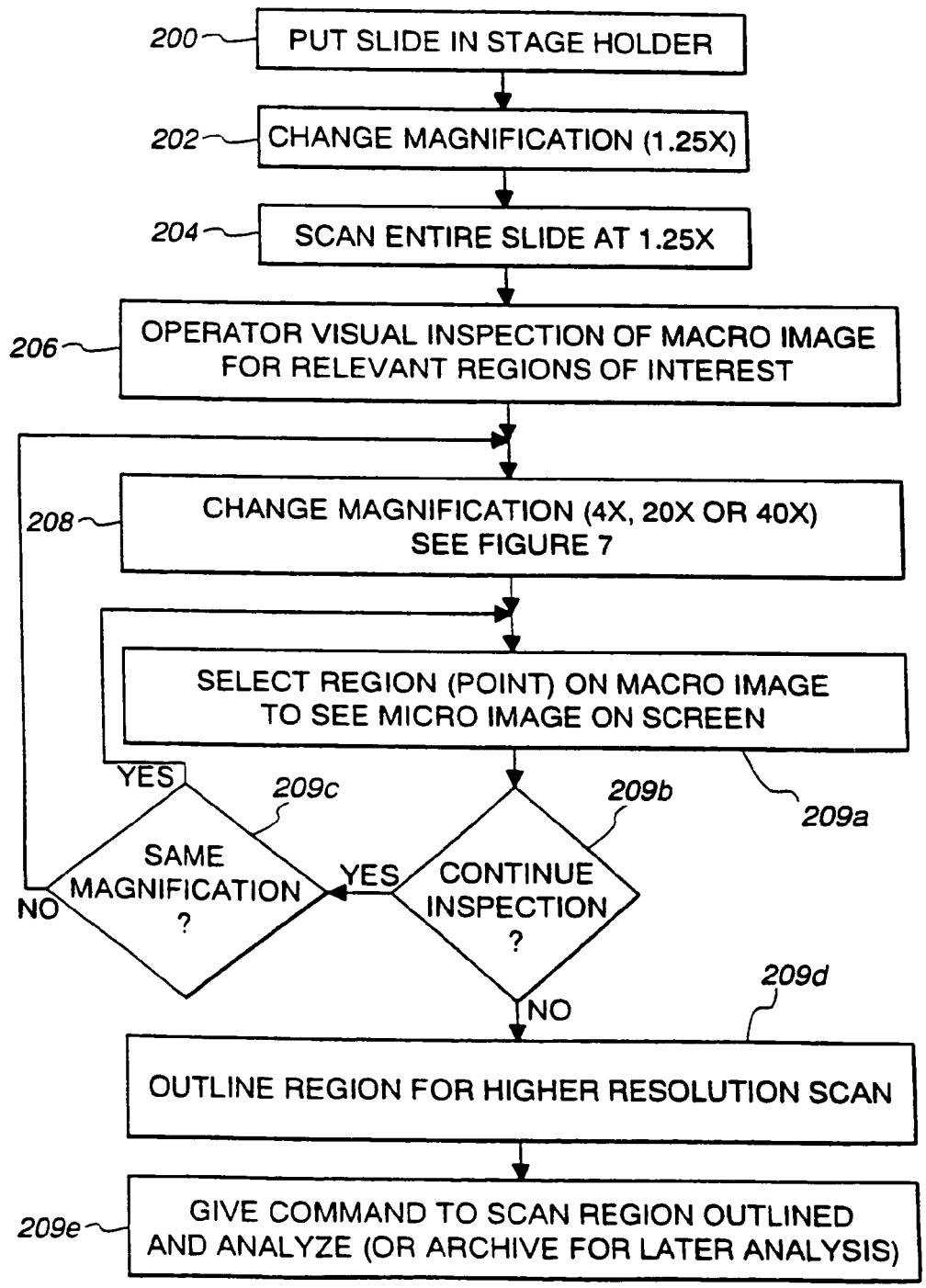
FIG. 11 is a flow diagram related to operation of the apparatus.

Referring now to the drawings, and especially to FIGS. 9A, 9B and 10, apparatus for synthesizing low magnification and high magnification microscopic images is shown therein and generally identified by reference numeral 10. The system includes a computer 12 which is a dual Pentium Pro personal computer in combination with a Hitachi HV-C20 video camera 14 associated with a Zeiss Axioplan 2 microscope 16. The computer system 12 is able to receive signals from the camera 14 which captures light from the microscope 16 having a microscope slide 10 positioned on an LUDL encoded motorized stage 20. The encoded motorized stage 20 includes a MAC 2000 stage controller for controlling the stage in response to the computer 12. A microscope slide 18 includes a biological specimen 21 which is to be viewed by the microscope and whose image is to be digitized both at low magnification and at high magnification as selected by a user. The low magnification digitized image is then displayed on a 21 inch Iiyama video display monitor 22 having resolution of 1600 by 1200 to provide display screens of the type shown in FIGS. 1 through 3 including a low magnification image 24, for instance, at 1.25 power, a high magnification image 26, for instance at 40× power and a control window or image 28. The low magnification image may have identified therein a region 30 which is reproduced at high magnification in high magnification screen or window 26 so that a pathologist or other operator of the system can review architectural regions of interest in low magnification image 24 and simultaneously view them in high magnification in the high magnification screen or window 26 to determine whether the cells forming a portion of the architectural feature need be examined further for cancer or the like or not.

The computer 10 is constructed around a PCI system bus 40 and has a first-Pentium Pro microprocessor 42 and a second pentium pro microprocessor 44 connected thereto. The system bus 40 has connected to it a PCI bus 50 and an ISA bus 52. The PCI bus 50 has a SCSI controller 60 connected thereto to send and receive information from a hard disk 62. The hard disk 62 also is coupled in daisy chain SCSI fashion to a high capacity removal disk and to a CD Rom drive 66. The hard disks 62 contains the programs for operating the system for controlling the microscope 16 and for processing the images as well as for doing a quantitative analysis of the selected portions of the histological specimens being viewed on the slide 18. The system bus 40 also has connected to it a random access memory 70 within which portions of the program being executed are stored as well as a read only memory 72 for holding a bootstrap loader as well as portions of the basic input/output operating system. A floppy disk controller 74 is coupled to the system bus 40 and has connected to it a floppy disk drive 76 for reading and writing information to a floppy disk as appropriate. A mouse controller 80 is coupled to the system bus and has a mouse 82 which operates as a pointing device for controlling manipulations on the screen 22 and within the windows 24, 26 and 28. A keyboard controller 90 is connected to the system bus and has a keyboard 92 connected thereto. The keyboard 92 may be used to send and receive alpha numeric signals to other portions of the computer. An audio controller 100 has a plurality of speakers 102 and a microphone 104 connected thereto for audio input and output and is coupled to the system bus 40. A network interface, such as a network interface card 104, is connected to the system bus and can provide signals via a channel 106 to other portions of a network or internet to which the system may be connected. Likewise, signals can be sent out of the system through a modem 110 connected to the ISA bus 52 and may be sent via a channel 112, for instance, to the internet. A printer 116 is connected via a parallel I/O controller 118 to the system bus in order to provide printouts as appropriate of screens and other information as it is generated. A serial I/O controller 122 is connected to the system bus and has connected to it a camera controller 124 which is coupled to CCD sensors 126 in the cameras. The CCD sensors 126 supply pixel or image signals representative of what is found on the slide 18 to an Epix pixci image acquisition controller 130 coupled to the PCI bus 50.

The microscope 16 includes a base 140 having a stage 20 positioned thereon as well as an objective turret 142 having a plurality of objectives 144, 146 and 148 thereon. The objective 144, for instance, may be of 1.25× objective. The objective 146 may be a 20× objective. The objective 148 may be a 40× objective. Signals from the camera sensors and controller are supplied over a bus 128 to the image acquisition system where they are digitized and supplied to the PCI bus for storage in RAM or for backing storage on the hard disk 62.

Figure 14:
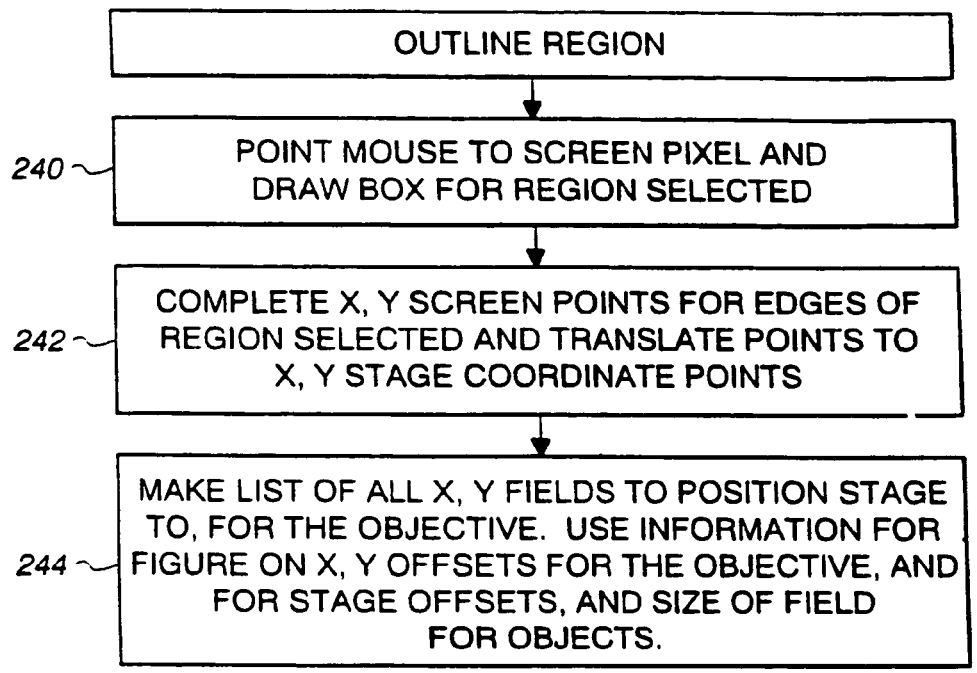
FIG. 14 is a flow chart for a region outlying routine.

When a specimen is on the slide 18 the stage 20 may be manipulated under the control of the computer through a stage controller 160 coupled to the serial I/O controller 122. Likewise, a microscope controller 162 controls aspects of the microscope such as the illumination, the color temperature or spectral output of a lamp 168 and the like. For instance, in normal operation, when a specimen is placed on the slide, specimen slide 18 is placed on the stage 20 in a step 200, as shown in FIG. 14, the processors 42 or 44 send a command through the system bus to cause the serial I/O controller 122 to signal the microscope controller to change magnification to 1.25× in a step 202. This is done by rotating the objective turret of the Axioplan 2 microscope to select the objective 144. Likewise, the controller sets the color temperature of the lamp 168, sets a pair of neutral density filter wheels 170 and 172 and sets a field diaphragm 174 for the correct illumination. A condenser diaphragm 176 is also controlled and a color filter wheel 180 may also be controlled to apply the appropriate filter color to the CCD censors 126 in the camera. The entire slide is then scanned in a step 204. The images are tiled and melded together into the overall image 24 supplied on the screen 22 to provide the operator in the step 206 with a visually inspectable macro image of relevant regions of the slide of interest.

In order to provide the magnified image, the mouse may be moved to identify a marker segment or region which, for instance, may be a rectangular region which will cause the microscope to change magnification as at step 208 to 4×, 20×, 40×, etc., by rotating the turret to bring the appropriate objective lens system into viewing position.

Next the user, in a step 209*a*, uses the mouse to select the region on the macro image in order to select the micro image to be viewed on the screen 22. In a step 209*b* a test is made to determine whether the user has commanded continued inspection. If the user has, a test is made in a step 209*c* to determine if the magnification is to be changed by changing the selected objective. In the event the magnification is to be changed control is transferred to the step 208. If the magnification is to remain unchanged control is transferred to the step 209*a*. In the event inspection is not to continue the region selected is outlined for higher magnification scan in a step 209*d*. In a step 209*e*, a command may be received to scan or acquire the higher magnification image for display in screen 26. The image may then be archived for later analysis, displayed or analyzed immediately.

In order to perform the magnification called for in step 206, the overall illumination and control of the microscope will be controlled so that in a step 210 the objective turret 142 will be rotated to place the higher power objective above the slide 18. In a step 212 voltage to the lamp will be changed to adjust the lamp 168 to provide the proper illumination and color temperature as predetermined for the selected objective. In a step 214, the condenser diaphragm 176 will have its opening-selected as appropriate to provide the proper illumination for that objective. In a step 216, the filter turret 180 will select the proper light wavelength filter to be supplied to the camera sensors. For instance, a red, blue or green filter, as appropriate, particularly if the specimen has been stained. In a step 218 the field diaphragm 174 will have its opening changed. In a step 220 the neutral density filter wheel 170 will select a neutral density filter and in a step 222 the neutral density filter wheel 172 will also select a neutral density filter. In a step 224 the X, Y and Z offsets will be used for reconstruction of the recorded image at the magnification and in a step 226 the current position will be read from encoders in the stage which are accurate to 0.10 micron.

In order to identify the selected region the mouse is moved to that area of the region in a pointing operation in a step 240 as shown in FIG. 14. The mouse may be moved to draw a box around the region selected. In a step 242 the X and Y screen points are computed for the edges of the regions selected and the computed image or pixel points are translated to stage coordinate points in order to control the stage of the microscope. In a step 244 a list of all of the X fields for positioning the stage for the objective is stored in random access memory and may be backed up on the hard disk. The information from the X offsets for the objective and the stage offsets is used as well as the size of the field to position the slide properly under the objective to capture the micro image.

Figure 15:
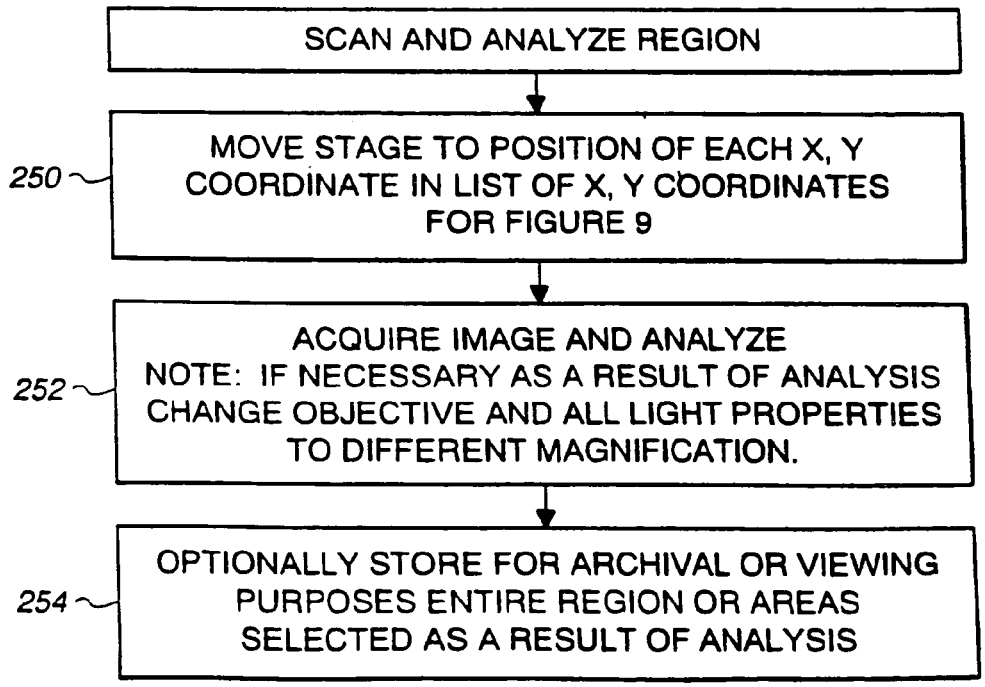
FIG. 15 is a flow chart for a scanning and analyzing routine.

When the slide has been positioned properly, as shown in FIG. 15 in a step 250 the stage is positioned for each of the X and Y coordinate values in stage coordinate values and the digitized image is captured by the cameras and stored in RAM and backed up on the hard disk. The image may be then analyzed quantitatively in various manners such as those set forth in the previously-identified United States application. Optionally the image may be stored for archival purposes in a step 254.

Figure 12:
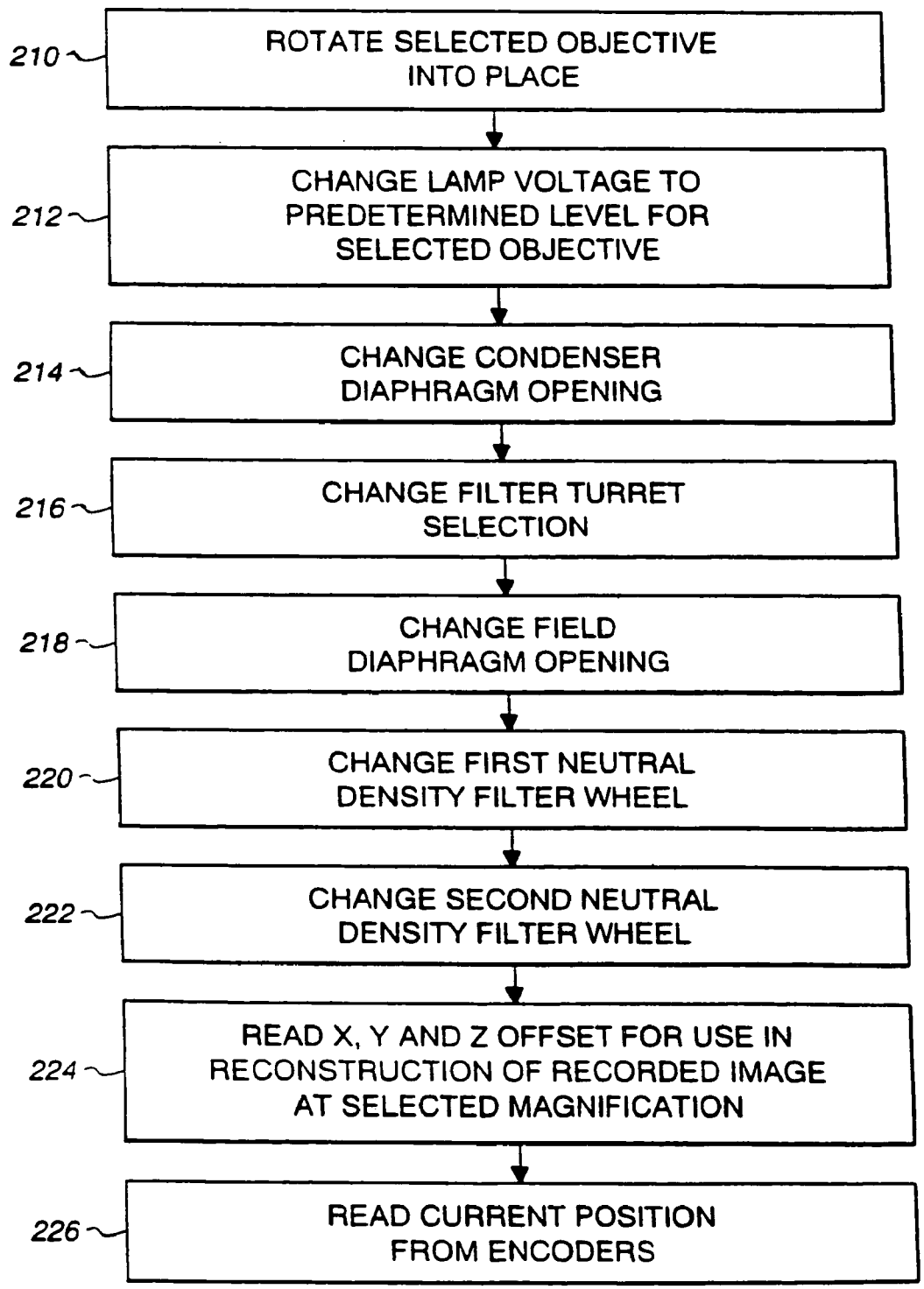
FIG. 12 is a flow diagram of details of one of the steps in FIG. 11.
Figure 13:
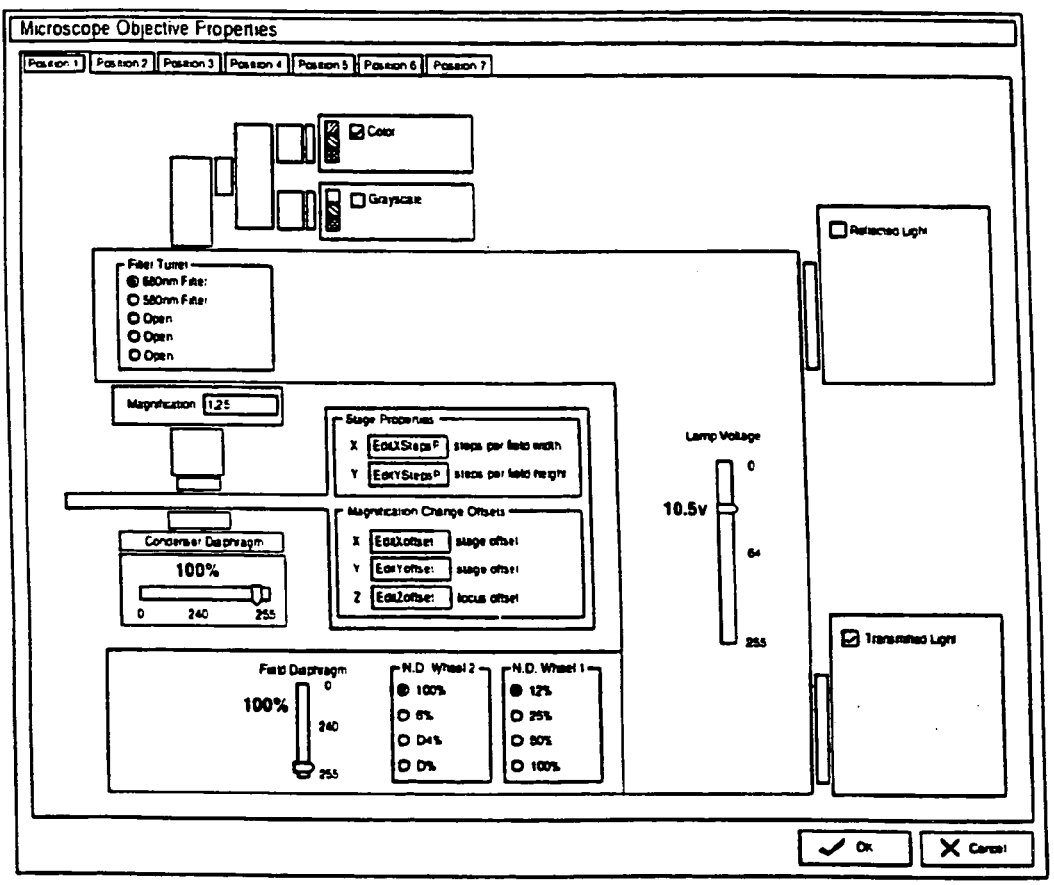
FIG. 13 is a display screen showing control parameters to be manipulated thereon.

In order to override the specific control functions that take place as shown in FIG. 12, a screen is provided as shown in FIG. 13 wherein the X-Y step size can be edited, the X, Y and Z offset can be edited, the lamp voltage can be selected, the neutral density filter can be selected as well as the opening of the field diaphragm and several other microscopic characteristics. FIG. 13 is a view of the settings of the microscope objective properties of the Axioplan 2, computer-controlled microscope.

Figure 16:
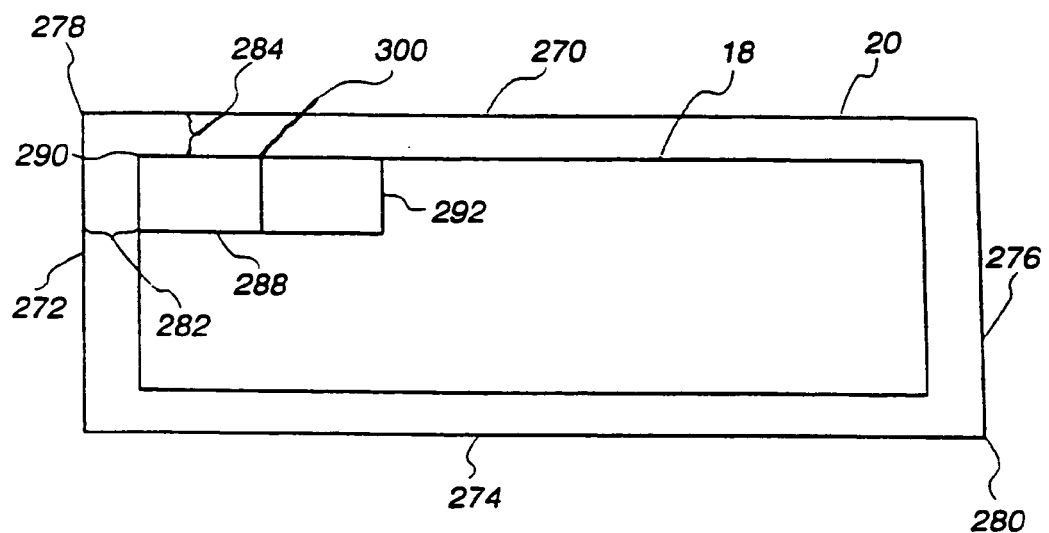
FIG. 16 is a schematic showing of the limits of travel of the microscope stage with respect to the image tiles.

The X and Y positioning is specifically carried out as shown in FIG. 16 where the slide 18 is shown with a slide boundary 270, 272, 274 and 276. Stage boundary for limits of the stage travel for purposes of the stage the stage can be moved all the way from an upper left hand corner of travel 276 to a lower right hand corner of travel 280. At the upper left hand bounded corner of travel 278 limits which a signal that the end of travel has been reached and the stage is then translated a short distance 282 in the extra action and a short distance 284 in the Y direction to define the first tile 288 in terms of a reference point 290 at its upper left hand corner. Since the size of the macro image tile 288 is known, the next macro image tile 292 may be placed contiguous with it by moving the stage appropriately and by measuring the location of the stage from the stage in counters without the necessity of performing any image manipulation. The image tiles 288 and 292 may be abutted without any substantial overlap or they may be overlapped slightly, such as a one pixel with overlap, which is negligible insofar as blurring of any adjacent edges of abutted image tiles. The upper left hand corner 300 of the tile 292 defines the rest of 292 and other tiles can be so defined. Micro image tiles can likewise be defined so that they are contiguous but not substantially overlapping, as would interfere with the composite image. This avoids the problems encountered with having to perform extended computations on digital images in a frame storer or multiple frame storage in order to match or bring the images into contiguity without blurriness at the edges of contiguous image tiles. It may be appreciated that the low power image 24 has a plurality of micro images defined therein which are tiled and which are shown in higher magnification as individual tiles 312, 314, 316 and the like. In addition, the region 310 when magnified as shown in the window 26 may exceed the bounds of the window and thus the window may include scroll bars or other means for allowing the image 310 which is larger than the window 26 to be examined from within the window 26.

Figure 16A:
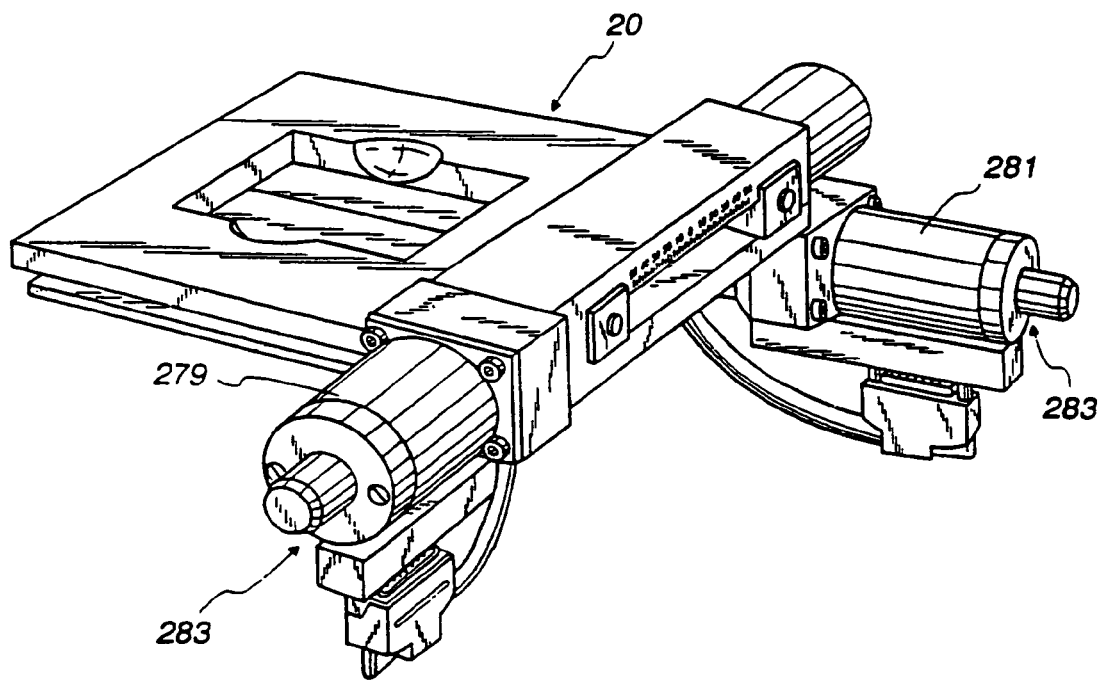
FIG. 16A is a perspective view of the microscope stage and stepper motors and encoders providing a closed loop drive for the motors.
Figure 17:
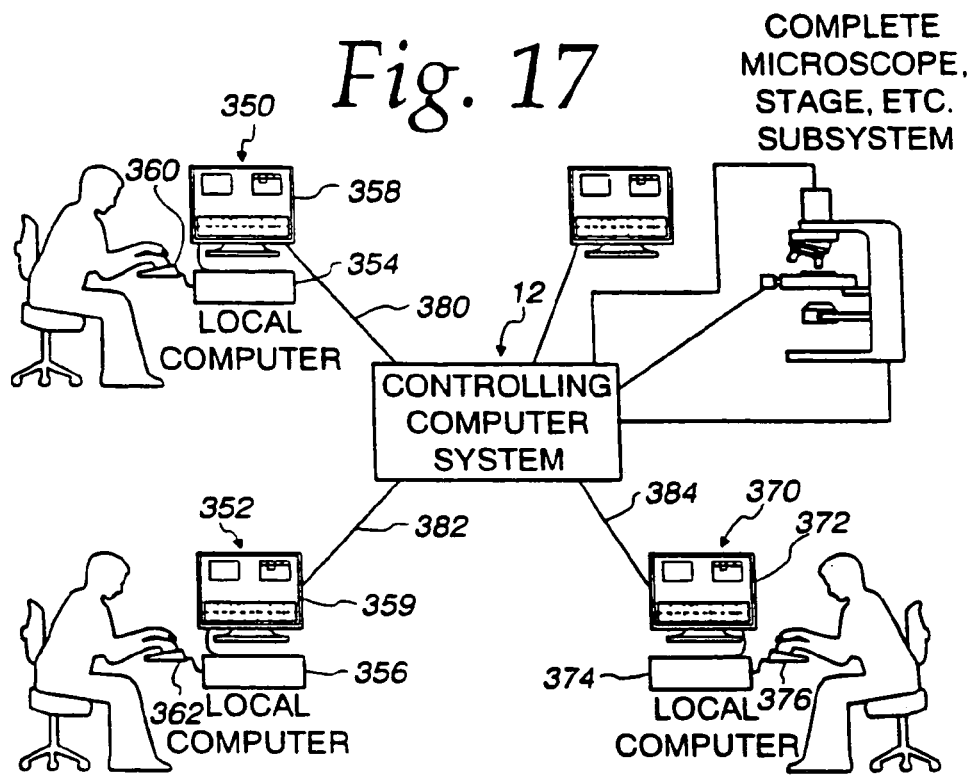
FIG. 17 is a block diagram of a networked system allowing multiple workstations to obtain access to the microscope and to manipulate the microscope locally at each workstation.
Figure 17A:
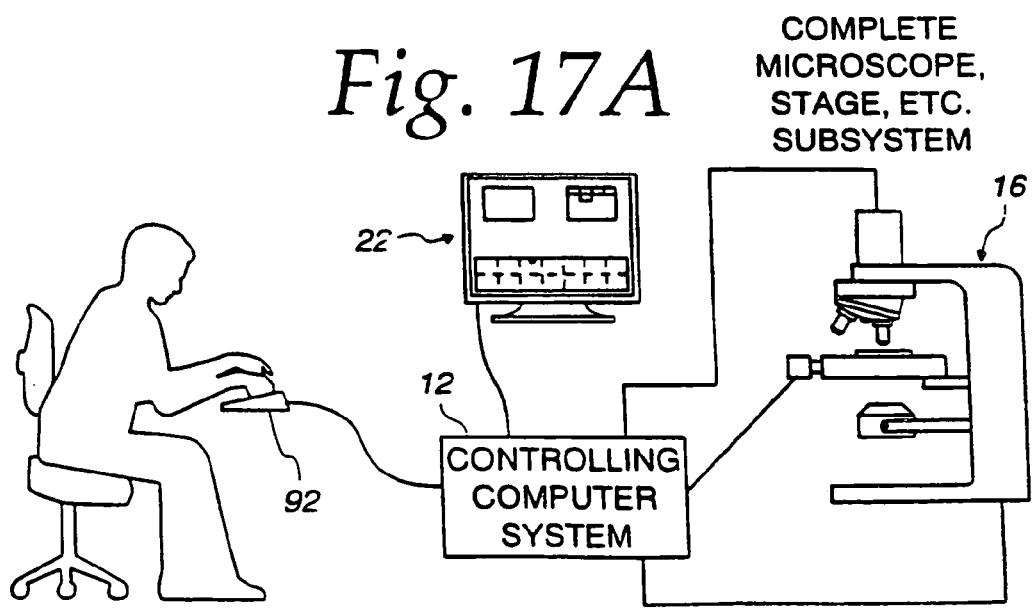
FIG. 17A is a view of the system described in connection with FIG. 10.

The stage 200 is best seen in FIG. 16A and includes the X and Y stepper motors 279 and 281 with their respective encoders, which provide a closed loop system to give the 0.1 micron accuracy versus the usual 5 or 6 micron accuracy of most microscope stages without a closed loop system. This closed loop system and this very high accuracy allow the abutting of the tile images for both high magnification and low magnification images without the substantial overlap and the time-consuming and expensive software currently used to eliminate the overlap and blurriness at the overlapping edges of adjacent image tiles. With the precisely positioned stage and by using the tiling system described in connection with FIG. 16, where the slide is precisely positioned relative to a center point CP for the slide, and the known position of point 278 is always taken from the same point, the tiles may be positioned precisely in a horizontal row and precisely in vertical rows to reconstruct the macro image and the micro image. This reconstruction is done without the use, as in the prior art, of extensive software manipulation to eliminate overlapping image tiles, horizontally or vertically or the haphazard orientation of image tiles.

The present invention also includes the facility for allowing remote observation to occur by being able to couple the system either over a network communication facility to an intranet, for instance via the network interface, or via a modem or other suitable connection, to an internet so that once the image has been scanned and stored in memory or, hard disks or other storage, remote users may be able to access the low magnification image as well as the high magnification image and move around within both images to make determinations as to the histological characteristics of the samples.

An additional feature of the system includes a plurality of networked workstations coupled to a first computer console 12 having a display screen 22 connected to the microscope 14. Satellite work stations 350 and 352 are substantially identical to the work station 12 including respective computers 354 and 356 coupled to displays 358 and 360. The devices can be manipulated through input devices 360 and 362 which may include a keyboard, mouse and the like. Also a third device can be connected including a work station 370, having a display 372, a computer 374 and an input device 376. Each of the devices is connected over respective network lines 380, 382, 384 to the computer 12 which transmission may be via either net or the like. Each of the different operators at the physically separate viewing stations can locate regions from the view of entire tissue cross sections via a macro view and label the regions for subsequent scanning and/or quantitative analysis. A single operator at the instrument station 12 can locate regions to view the entire tissue cross section. Those regions can be labeled for subsequent scanning and/or quantitative analysis with subsequent review and physically remote viewing stations, for instance, in an operating room or in individual pathologists' signout areas in order to review analysis results while still maintaining and reviewing the entire macro view of the tissue and/or the individual stored images from which the quantitative results were obtained. The viewing stations 350, 352 and 370 can comprise desk top computers, laptops, etc. There is no need for a microscope at the network stations 350, 352 and 370.

In a still further alternative embodiment, remote workstations 400, 402, 404, 406 and 408 may be connected through a server 410 which may be supplied via a packet switched network. The server 410 and may be a hypertext transport protocol based server of the type used for the World Wide Web or may be a telnet type server as used previously in internet remote operation applications. The server 410 communicates via a communications channel 414 with a local computer 416 having a display 418 associated therewith, the local computer 416 being connected to the Microscope 420. Each of the remote work stations 400, 402, 404, 406 and 408 may perform the same operations as the stations 350, 352 and 370 although they do it from nearby buildings or even from around the world, thus providing additional flexibility for others to make use of the specimen obtained and being viewed under the microscope 420. In addition, stored images may be disseminated through the server 410 to the remote servers 400 through 408 for further analysis and review.

The server was designed to interact with either a thin client browser or with a Java applet viewer, operating through an HTML browser such as Netscape or the Microsoft Internet Explorer.

Figure 28:
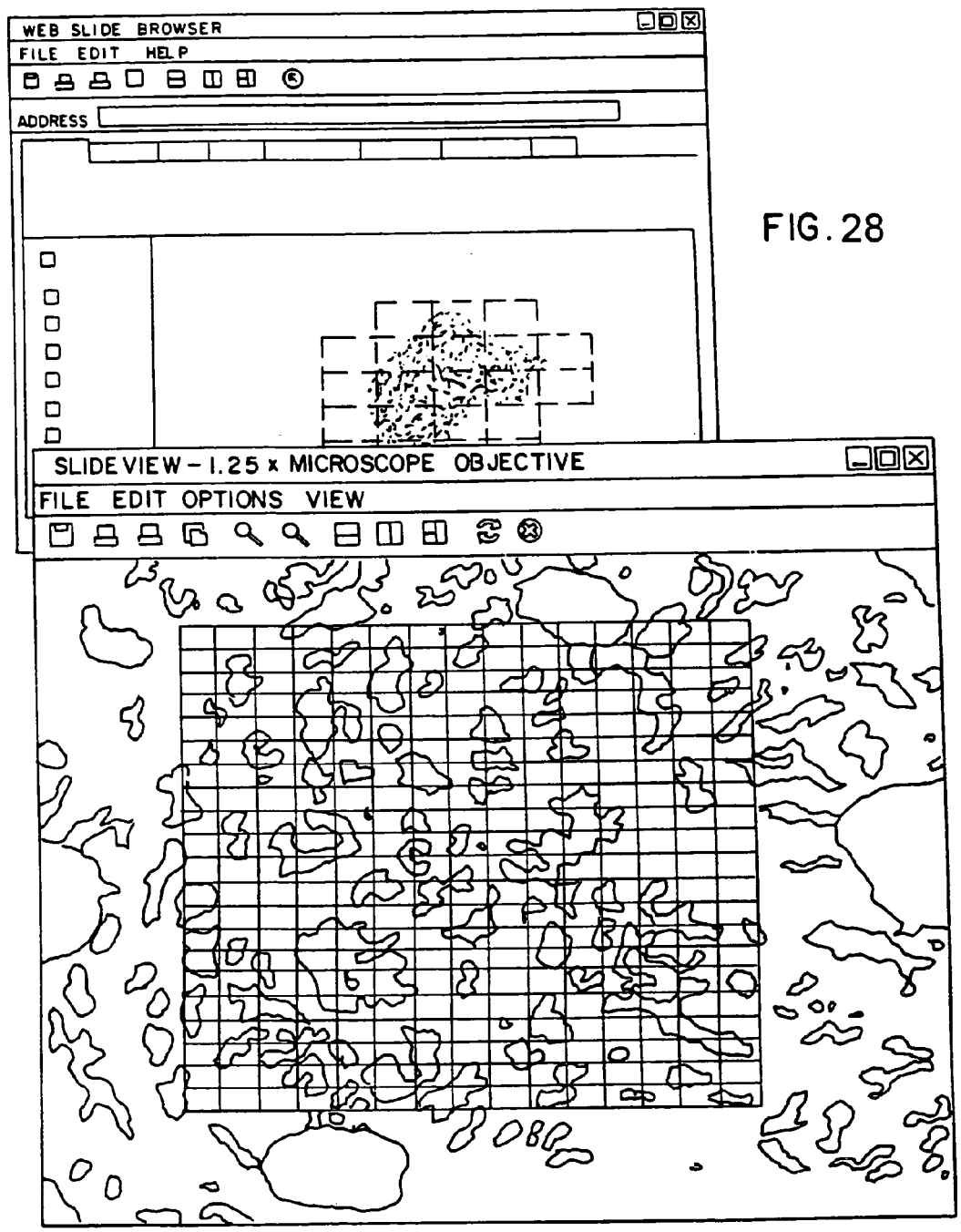
FIG. 28 shows a Slide View window chosen by selecting a point on the browser main window thumbnail image, a Slide View image shows an overlay set of a tiled region from which one or more higher-magnification Field View images may be chosen.

The server runs on a standard PC under a Windows operating system. It uses HTTP Internet communication protocols. The computer has stored on its storage media already collected data files having the data structure disclosed above. This data structure consists of "tiled" sets of digital images, with x, y information organized to aid the viewer program to "reconstruct" and spatially align physically-contiguous images, at multiple resolutions. The server responds to HTTP "Get" requests from multiple thin client browsers or other browsers with embedded Java applet viewers. As such, it uses a "listening socket" and a number of short-lived "threads" which handle "Get" requests independently and simultaneously, as shown in FIG. 28.

Figure 29:
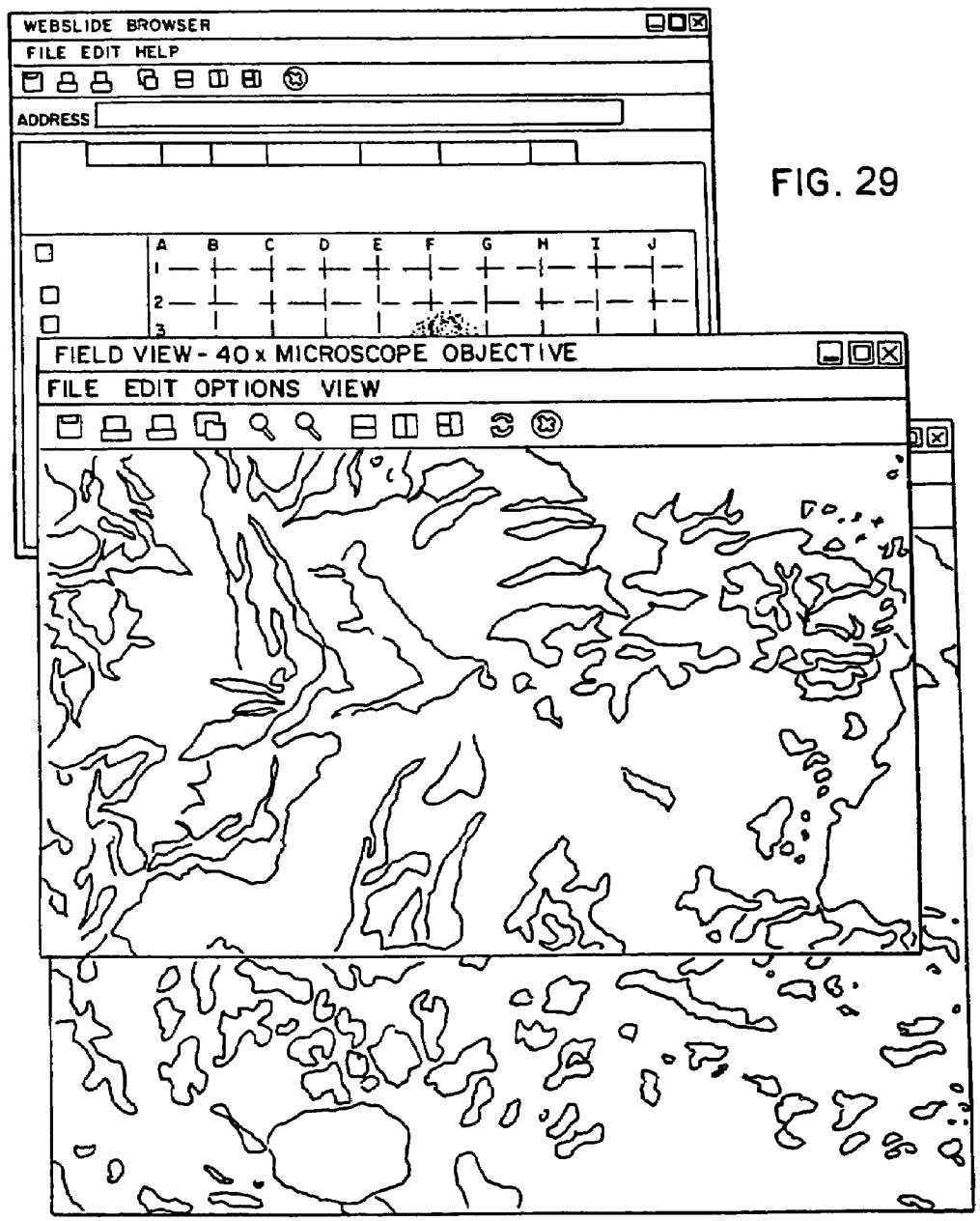
FIG. 29 shows a Field View window chosen by selecting an image tile region of the Slide View window shown in FIG. 28 using a pointer.

After initial logic, as shown in FIG. 29, to determine whether the HTTP request is valid and, if so, whether it is a Java request for a thin client request, the server generates a response thread, depending upon the request as detailed in Table 1, to send back the requested information to the client. Large numbers of these requests can be handled at one time.

The server 12 was designed to interact with a client having either a thin client browser or with a Java applet viewer, operating through an HTML browser such as Netscape Navigator or Microsoft Internet Explorer.

Figure 19:
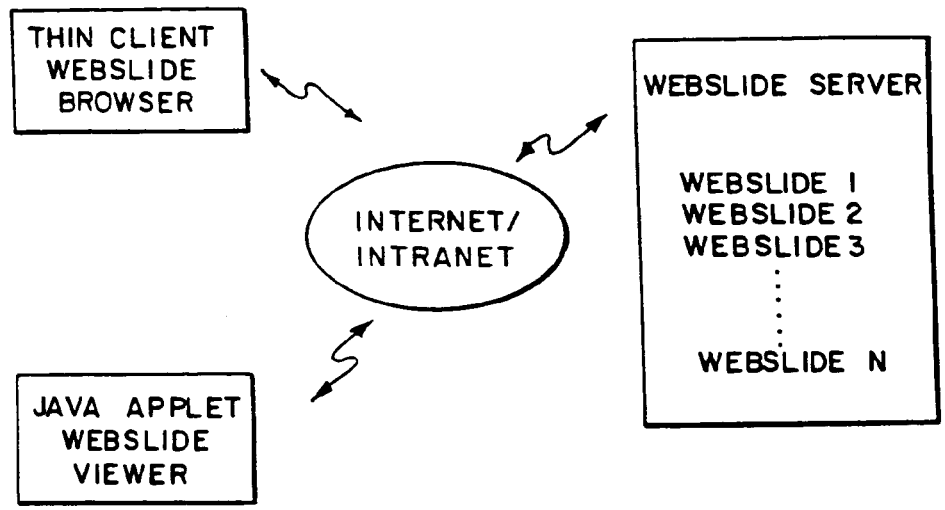
FIG. 19 shows a system having interlinking and an integrated combination of image viewer and server concept using an Internet or intranet connection embodying the present invention.

The server 12 runs on a standard PC under a Windows operating system. It uses the HTTP communication protocol. The computer 12 has stored on its storage media already collected data files of with the data structure disclosed in U.S. application Ser. No. 09/032,514, filed Feb. 27, 1998, which is incorporated herein by reference. This data structure consists of "tiled" sets of digital images, with x, y information organized to aid the viewer program to "reconstruct" and spatially align physically-contiguous images, at multiple resolutions. The server responds to HTTP "GET" requests from multiple thin client browsers or other browsers with embedded Java applet viewers. As such, it uses a "listening socket" and a number of short-lived "threads" which handle "GET" requests independently and simultaneously, as shown in FIG. 19.

Figure 20:
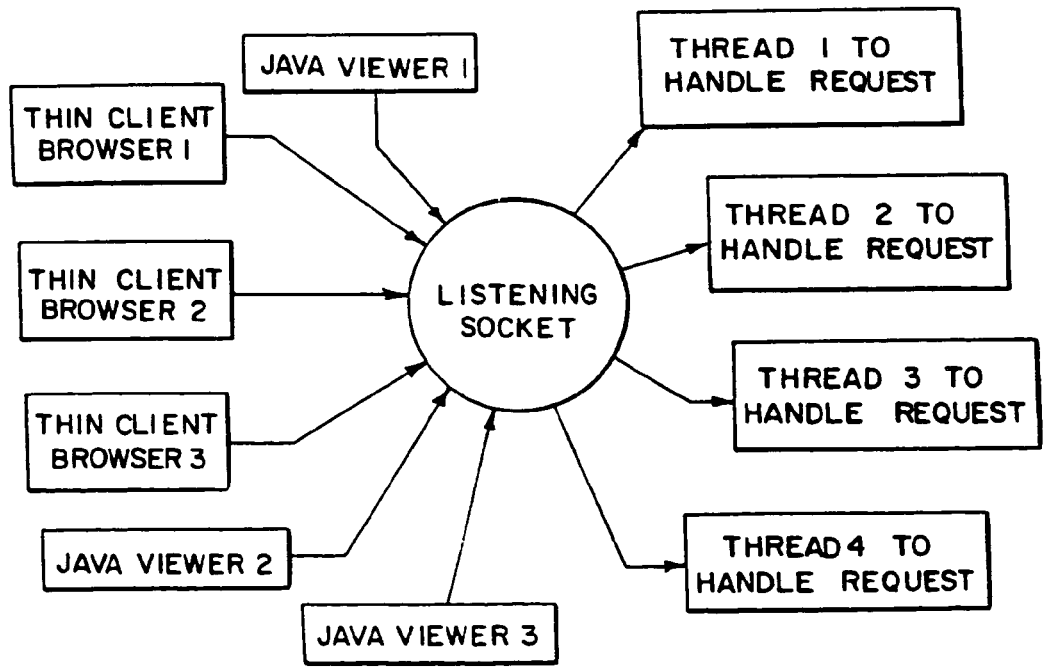
FIG. 20 shows a server comprising a portion of the system shown in FIG. 19 and functioning as a listening socket to respond to GET requests and create event threads in a simultaneous multi-threaded operating environment.

After initial logic, as shown in FIG. 20, to determine whether the HTTP request is valid and, if so, whether it is a Java request or a thin client request, the server generates a response thread, depending upon the request as detailed in Table 4, to send back the requested information to the client. Large numbers of these requests can be handled at one time.

TABLE 4

Client - Server "GET" Interactions

| Client Requests | | Server Responses |
|---|---|---|
| Login Request<br>User Name<br>Nickname<br>E-mail address | > < | Acknowledges<br>Assigns and sends ID#<br>to Client |
| Slide Tray Request | > < | Sends Slide Tray Information<br>List of image names and URL<br>path locations on the server,<br>extracted folder names and<br>header text |
| Update Request<br>User Name<br>Nickname<br>E-mail address<br>Tray index<br>Slide Name<br>Slide View Window<br>Information<br>Zoom Level<br>x, y position<br>Field View Window<br>Information<br>Zoom Level<br>x, y position<br>Action Status<br>Pointer Location x, y<br>Chat Buffer Index | > < | Sends same information to<br>requesting Client, for all<br>of Clients currently logged<br>in, i.e., User Name,<br>Nickname, etc. |
| Chat Line Request<br>ID# | > < | Sends Chat Line message<br>string |

TABLE 4-continued

Client - Server "GET" Interactions

| Client Requests | | Server Responses |
|---|---|---|
| Select Slide Request Modified URL Path of Selected Slide | > < | Sends x, y coordinate list for all tiles associated with clients selected URL and the Preview Slide image. |
| Image Request | > < | Send specified image, e.g., an image tile or thumbnail image |
| Logoff Request | > < | Acknowledge Release User ID# |
| Java Applet Request | > < | Send Java Applet |
| Java Login and Virtual Slide Request Slide Name Verify Server Identity | > < | Send thumbnail and Preview Images and x, y list of title images |
| Java Image Tile Request | > < | Send requested image tile |

In addition to the tiled image data, and the x, y coordinate lists for each tile of the image data, as set forth in Table 5 below there are several small reconstructed images that are stored in the individual folder, or on the server. These facilitate bringing image content to the client viewing screen rapidly, and can be used as an aid in determining what viewing options to choose in the various viewing programs.

TABLE 5

| | | | |
|---|---|---|---|
| DA0 | JPG | 57,996 | Da0.jpg |
| Da1 | JPG | 75,646 | Da1.jpg |
| Da10 | JPG | 75,874 | Da10.jpg |
| Da100 | JPG | 61,564 | Da100.jpg |
| Da101 | JPG | 65,982 | Da101.jpg |
| Da102 | JPG | 76,912 | Da102.jpg |
| Da103 | JPG | 75,729 | Da103.jpg |
| Da104 | JPG | 70,727 | Da104.jpg |
| Da105 | JPG | 68,184 | Da105.jpg |
| Da106 | JPG | 73,355 | Da106.jpg |
| Da107 | JPG | 21,296 | Da107.jpg |
| Da108 | JPG | 29,384 | Da108.jpg |
| Da109 | JPG | 28,163 | Da109.jpg |
| Da11 | JPG | 79,808 | Da11.jpg |
| Da110 | JPG | 76,373 | Da110.jpg |
| Da111 | JPG | 35,540 | Da111.jpg |
| Da112 | JPG | 21,293 | Da112.jpg |
| Da113 | JPG | 34,366 | Da113.jpg |
| Da114 | JPG | 76,120 | Da114.jpg |
| Da115 | JPG | 70,933 | Da115.jpg |
| Da116 | JPG | 47,658 | Da116.jpg |
| Da117 | JPG | 77,465 | Da117.jpg |
| Da118 | JPG | 79,024 | Da118.jpg |
| Da119 | JPG | 78,256 | Da119.jpg |
| Da12 | JPG | 72,381 | Da12.jpg |
| Da120 | JPG | 76,733 | Da120.jpg |
| Da121 | JPG | 79,086 | Da121.jpg |
| Da122 | JPG | 79,003 | Da122.jpg |
| Da123 | JPG | 71,881 | Da123.jpg |
| Da124 | JPG | 75,408 | Da124.jpg |
| Da125 | JPG | 74,486 | Da125.jpg |
| Da126 | JPG | 80,568 | Da126.jpg |
| Da127 | JPG | 79,061 | Da127.jpg |
| Da128 | JPG | 79,495 | Da128.jpg |
| Da129 | JPG | 70,019 | Da129.jpg |
| Da13 | JPG | 73,489 | Da13.jpg |
| Da14 | JPG | 76,530 | Da14.jpg |
| Da15 | JPG | 76,353 | Da15.jpg |
| Da16 | JPG | 29,611 | Da16.jpg |
| Da17 | JPG | 72,668 | Da17.jpg |
| Da18 | JPG | 66,130 | Da18.jpg |
| Da19 | JPG | 83,813 | Da19.jpg |
| Da2 | JPG | 76,115 | Da2.jpg |
| Da20 | JPG | 69/762 | Da20.jpg |
| Da21 | JPG | 79,036 | Da21.jpg |

TABLE 5-continued

| | | | |
|---|---|---|---|
| Da22 | JPG | 80,779 | Da22.jpg |
| Da23 | JPG | 38,576 | Da23.jpg |
| Da24 | JPG | 65,975 | Da24.jpg |
| Da25 | JPG | 73,812 | Da25.jpg |
| Da26 | JPG | 80,660 | Da26.jpg |
| Da27 | JPG | 72,939 | Da27.jpg |
| Da28 | JPG | 88,332 | Da28.jpg |
| Da29 | JPG | 66,672 | Da29.jpg |
| Da3 | JPG | 78,399 | Da3.jpg |
| Da30 | JPG | 29,994 | Da30.jpg |
| Da31 | JPG | 57,465 | Da31.jpg |
| Da32 | JPG | 74,006 | Da32.jpg |
| Da33 | JPG | 78,765 | Da33.jpg |
| Da34 | JPG | 54,120 | Da34.jpg |
| Da35 | JPG | 82,550 | Da35.jpg |
| Da36 | JPG | 63,735 | Da36.jpg |
| Da37 | JPG | 41,253 | Da37.jpg |
| Da38 | JPG | 69,759. | Da38.jpg |
| Da39 | JPG | 49,376 | Da39.jpg |
| Da4 | JPG | 77,922 | Da4.jpg |
| Da40 | JPG | 52,514 | Da40.jpg |
| Da41 | JPG | 68,291 | Da41.jpg |
| Da42 | JPG | 69,726 | Da42.jpg |
| Da43 | JPG | 79,840 | Da43.jpg |
| Da44 | JPG | 80,526 | Da44.jpg |
| Da45 | JPG | 84,245 | Da45.jpg |
| Da46 | JPG | 50,315 | Da46.jpg |
| Da47 | JPG | 73,069 | Da47.jpg |
| Da48 | JPG | 73,188 | Da48.jpg |
| Da49 | JPG | 69,155 | Da49.jpg |
| Da5 | JPG | 69,257 | Da5.jpg |
| Da50 | JPG | 69,087 | Da50.jpg |
| Da51 | JPG | 74,156 | Da51.jpg |
| Da52 | JPG | 82,847 | Da52.jpg |
| Da53 | JPG | 74,838 | Da53.jpg |
| Da54 | JPG | 69,003 | Da54.jpg |
| Da55 | JPG | 73,524 | Da55.jpg |
| Da56 | JPG | 65,242 | Da56.jpg |
| Da57 | JPG | 67,796 | Da57.jpg |
| Da58 | JPG | 70,367 | Da58.jpg |
| Da59 | JPG | 39,998 | Da59.jpg |
| Da6 | JPG | 68,210 | Da6.jpg |
| Da60 | JPG | 14,487 | Da60.jpg |
| Da61 | JPG | 76,801 | Da61.jpg |
| Da62 | JPG | 74,394 | Da62.jpg |
| Da63 | JPG | 69,446 | Da63.jpg |
| Da64 | JPG | 63,296 | Da64.jpg |
| Da65 | JPG | 17,568 | Da65.jpg |
| Da66 | JPG | 71,935 | Da66.jpg |
| Da67 | JPG | 71,736 | Da67.jpg |
| Da68 | JPG | 67,406 | Da68.jpg |
| Da69 | JPG | 74,488 | Da69.jpg |
| Da7 | JPG | 69,660 | Da7.jpg |
| Da70 | JPG | 45,382 | Da70.jpg |
| Da71 | JPG | 69,849 | Da71.jpg |
| Da72 | JPG | 12,009 | Da72.jpg |
| Da73 | JPG | 62,862 | Da73.jpg |
| Da74 | JPG | 68,522 | Da74.jpg |
| Da75 | JPG | 67,734 | Da75.jpg |
| Da76 | JPG | 60,510 | Da76.jpg |
| Da77 | JPG | 26,689 | Da77.jpg |
| Da78 | JPG | 68,839 | Da78.jpg |
| Da79 | JPG | 67,137 | Da79.jpg |
| Da8 | JPG | 71,914 | Da8.jpg |
| Da80 | JPG | 65,232 | Da80.jpg |
| Da81 | JPG | 78,365 | Da81.jpg |
| Da82 | JPG | 63,535 | Da82.jpg |
| Da83 | JPG | 74,889 | Da83.jpg |
| Da84 | JPG | 71,895 | Da84.jpg |
| Da85 | JPG | 65,744 | Da85.jpg |
| Da86 | JPG | 76,849 | Da86.jpg |
| Da87 | JPG | 74,373 | Da87.jpg |
| Da88 | JPG | 73,449 | Da88.jpg |
| Da89 | JPG | 69,255 | Da89.jpg |
| Da9 | JPG | 74,054 | Da9.jpg |
| Da90 | JPG | 65,637 | Da90.jpg |
| Da91 | JPG | 62,566 | Da91.jpg |
| Da92 | JPG | 75,703 | Da92.jpg |
| Da93 | JPG | 70,315 | Da93.jpg |

TABLE 5-continued

| Da94 | JPG | 63,884 | Da94.jpg |
| Da95 | JPG | 62,949 | Da95.jpg |
| Da96 | JPG | 69,046 | Da96.jpg |
| Da97 | JPG | 77,595 | Da97.jpg |
| Da98 | JPG | 71,528 | Da98.jpg |
| Da99 | JPG | 58,862 | Da99.jpg |

Each image has a PreviewSlide.jpg image contained in its data structure. This is a "thumbnail" image reconstructed from all of the tiles from the low magnification, 1.25× slide view image tiles. The reconstructed composite image has been digitally reduced to an image size of 454×240. During server startup, for each data structure found as described below, this Preview Slide image is further converted to an additional thumbnail-image of 232×120. The use of the Preview Slide and thumbnail images will be described below. Also, if specific HTML Java applet views have been chosen, four reconstructed .jpg images from each view, corresponding to four different magnifications have also been stored on the server, as described in detail below under the Java applet creator description and image viewer descriptions.

Figure 21:
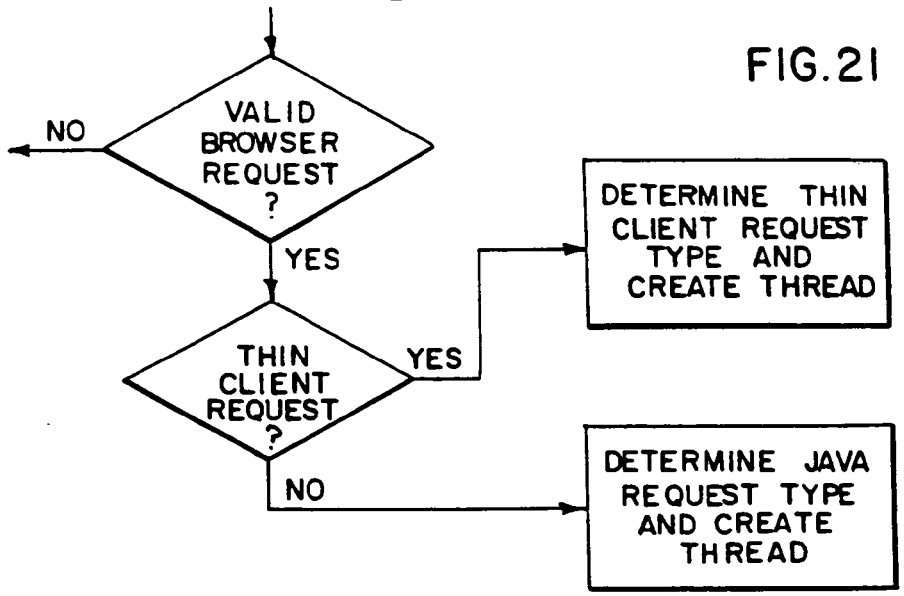
FIG. 21 shows logic to determine valid GET requests.
Figure 22A:
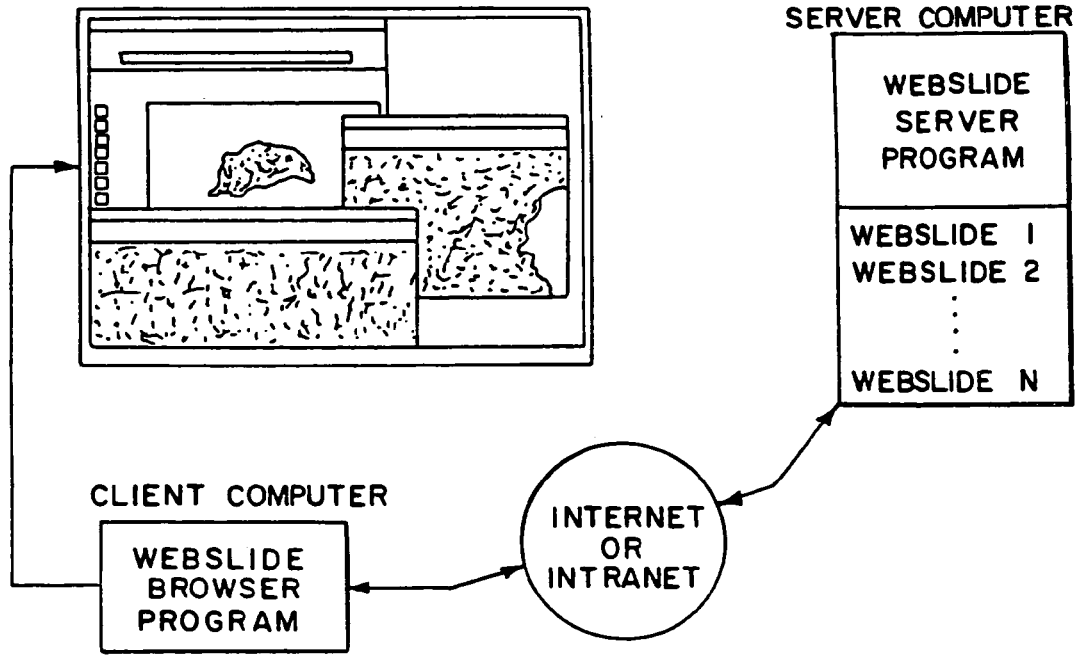
FIG. 22A shows an interaction between a thin client browser program and the Internet or intranet server computer with a server program as shown in FIG. 20.
Figure 22B:
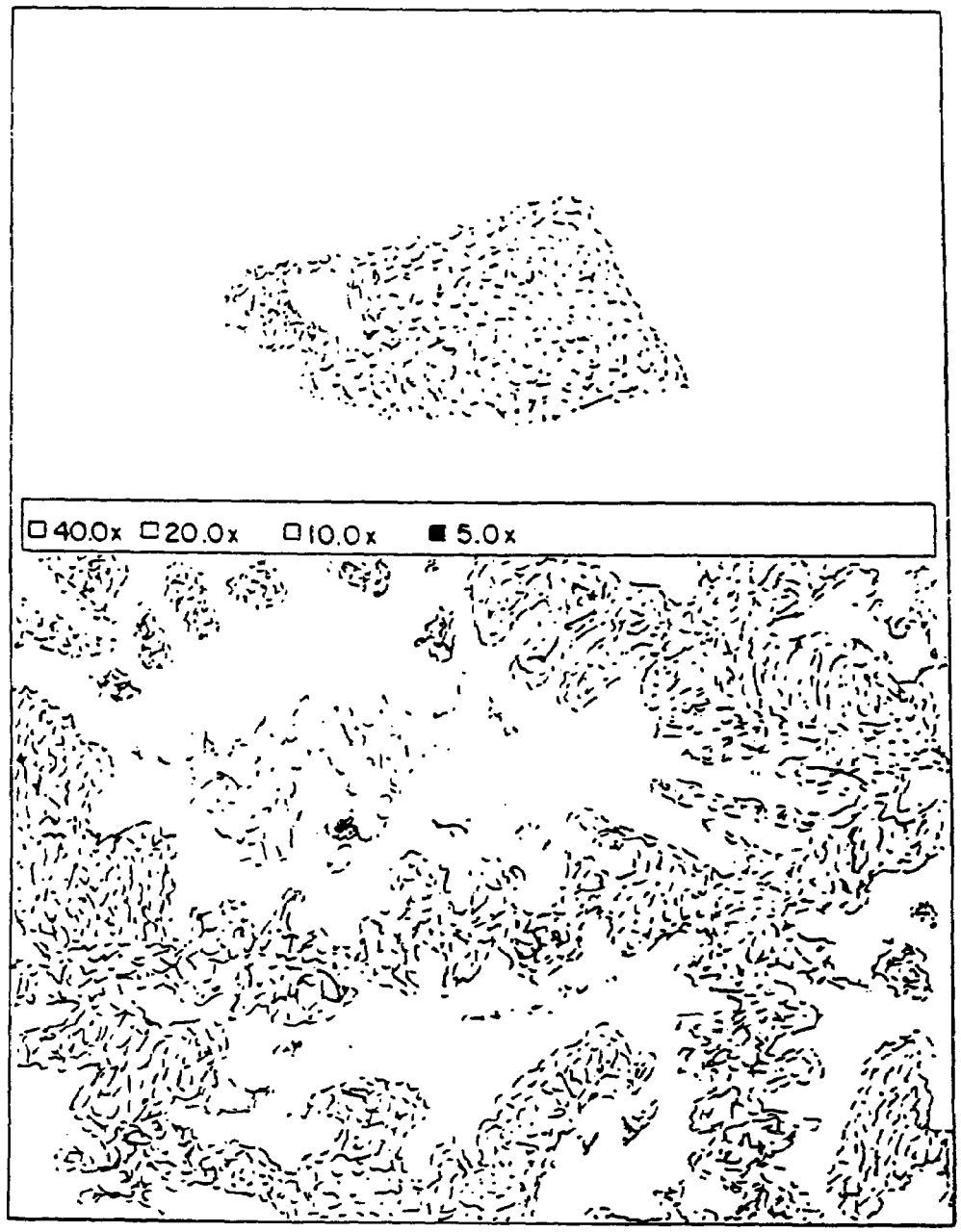
FIG. 22B shows an HTML-embedded Java applet viewer window for a client subsystem of the system shown in FIG. 19.
Figure 23:
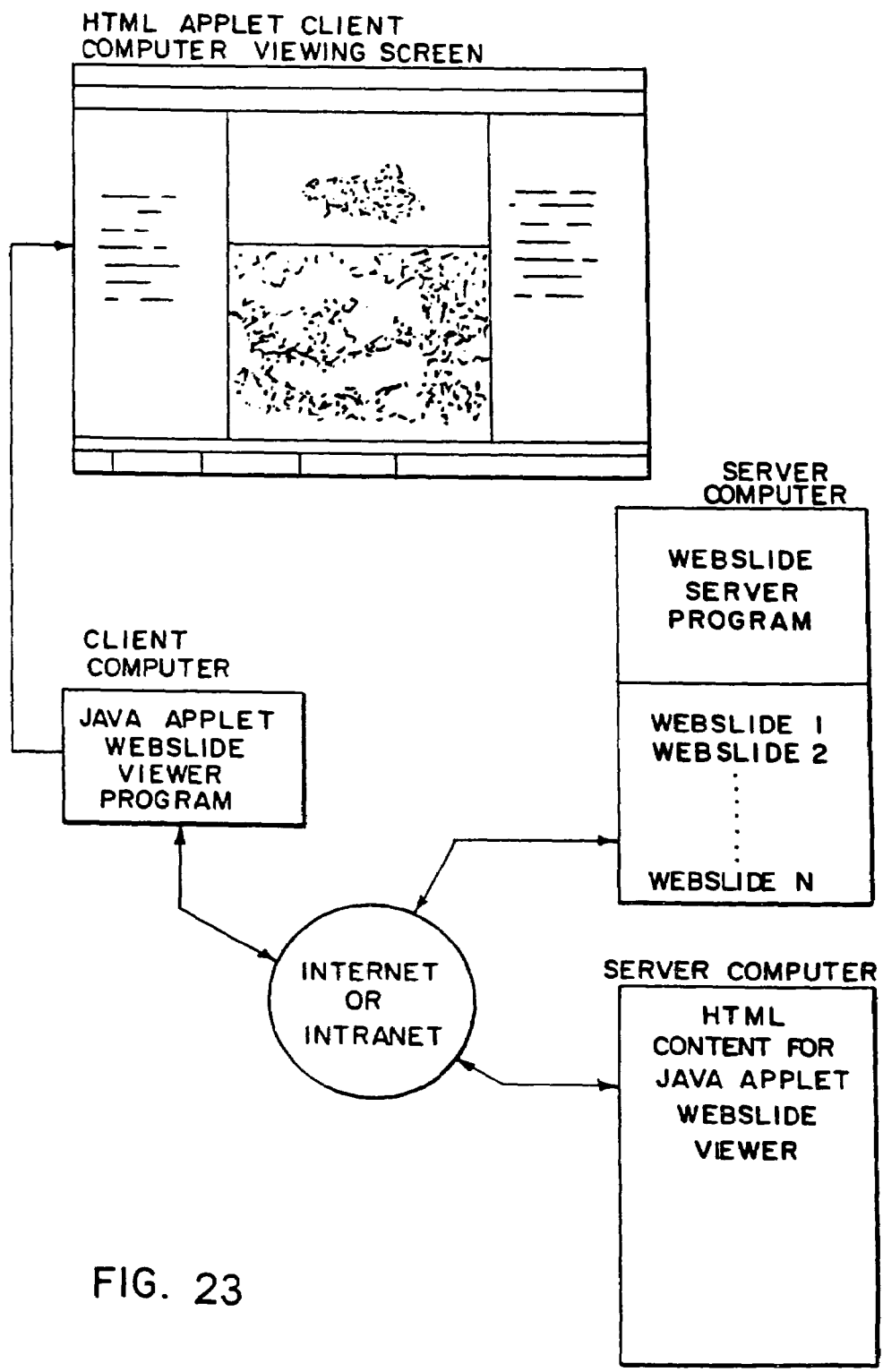
FIG. 23 shows an interaction between a Java applet program and Internet or intranet servers executing a server program and embodying the present invention.

FIGS. 21A, 21B and 22 illustrate two different virtual microscope slide viewing implementations. These suit two different needs. The thin client browser has three screens and many more functions. As described in more detail below, there is a main screen that displays the thumbnail Preview Slide image, and uses a tabbed interface to implement different functionalities to the browser. Some of these important functionalities are: (1) a SlideTray tab, which allows for the selection of any of the stored images hosted on the server computer; (2) a server tab, which allows coordination of views and chats with multiple other clients all logged-in at the same time; and (3) an Applet Creation tab to select specific region views for HTML applets viewed by the Java Applet viewer. The other two windows, Slide View and Field View, allow viewing of low-magnification tiled images and high-magnification tiled images with scrolling and coordination between the two views.

The thin client browser is more suited to secondary opinion expert pathology consultations, and sophisticated professional pathology users in departmental pathology practice, for review of cases and as archival backup virtual slide records. In operation, the browser program is loaded separately, once on a client computer. After that it can be used to access any number of servers, as described below, by simply typing in the Internet address of the server. It is faster than the JAVA applets because it comprises code which is already compiled, and is not based upon interpreted applet execution. It is unnecessary to load the thin client browser for every virtual microscope slide viewed. During creation of the image, only smaller regions of specific diagnostic material need be scanned at high magnification, thus saving time during the scanning process.

The HTML applet viewer is simpler than the thin client browser, and may be used in medical student, dental student, veterinary and undergraduate biology teaching situations. Advantage is taken of the fact that most students are familiar with an HTML browser. Instructors can easily add course "content" text to provide different descriptions of the virtual microscope slide images. Since the virtual microscope slides will often be used for longer periods, and since there is no premium on speed of scanning, entire specimens can be scanned offline at high magnification which takes a longer time. In this viewer simply acts as a "portal," or a small window, in a fixed position on a specific HTML page.

As described below, each applet instance relates to a specific image on a specific server computer. There are two parts to the view, the upper part of the portal is a display of the Preview Slide image. The bottom part of the portal initially shows a selected view from that image at one of four magnifications. A plurality of radio button choices loaded on a bar between the views allows for additional magnification choices in the bottom view. The bottom view is also scrollable, and can be changed by pointing the mouse to a region on the Preview Slide image.

It will-be appreciated that this viewer is simpler to learn initially and to operate than the thin client browser. It has the disadvantage of being slower and of only addressing one image at a time. It has an advantage of being simple, having various types of explanatory text right next to the image, and of being cross platform with regard to operating system, computer type and HTML browser type. These are all helpful in the educational market.

The Slide Tray-concept is used in the server and the browser programs and is central to providing an organizational construct to collections of images. It is set forth in Table 6 below.

TABLE 6

| FINALS~1 | INI | 3,902  | FinalScan.ini    |
| PREVIE~1 | JPG | 6,210  | PreviewSlide.jpg |
| SLIDES~1 | INI | 654    | SlideScan.ini    |
| SS1      | JPG | 10,285 | SS1.jpg          |
| SS10     | JPG | 63,150 | SS10.jpg         |
| SS11     | JPG | 70,838 | SS11.jpg         |
| SS12     | JPG | 15,535 | SS12.jpg         |
| SS13     | JPG | 12,071 | SS13.jpg         |
| SS14     | JPG | 73,847 | SS14.jpg         |
| SS15     | JPG | 70,783 | SS15.jpg         |
| SS16     | JPG | 25,178 | SS16.jpg         |
| SS17     | JPG | 2,983  | SS17.jpg         |
| SS18     | JPG | 9,035  | SS18.jpg         |
| SS19     | JPG | 15,629 | SS19.jpg         |
| SS2      | JPG | 25,194 | SS2.jpg          |
| SS20     | JPG | 4,200  | SS20.jpg         |
| SS3      | JPG | 9,936  | SS3.jpg          |
| SS4      | JPG | 10,118 | SS4.jpg          |
| SS5      | JPG | 4,559  | SS5.jpg          |
| SS6      | JPG | 35,961 | SS6.jpg          |
| SS7      | JPG | 86,933 | SS7.jpg          |
| SS8      | JPG | 16,212 | SS8.jpg          |
| SS9      | JPG | 33,872 | Ss9.jpg          |

[Header]
tPatientID=Prostate
tAccession=
tOperatorID=
tTimeOfScan=9/17/98 4:56:31 PM
lXStageRef=278000
lYStageRef=142500
iImageWidth=752
iImageHeight=480
lXStepSize=1588
lYStepSize=1184
lXOffset=0
lYOffset=0
dMagnification=40
tImageType=.jpg
iFinalImageQuality=60
lAnalysisImageCount=130
lCalibrationImageCount=0
iiTotalBytes=9221691
tFolder=Test WSTP
[Da0]
x=164208
y=45264
[Da1]
x=162672
y=45264

TABLE 6-continued

[Da2]
x=161136
y=45264
[Da3]
x=159600
y=45264
[Da4]
x=158064
y=45264
[Da5]
x=156528
y=45264
[Da6]
x=154992
y=45264
[Da7]
x=164208
y=44080
[Da8]
x=162672
y=44080
[Da9]
x=161136
y=44080
[Da10]
x=159600
y=44080
[Da11]
x=158064
y=44080
[Da12]
x=156528
y=44080
[Da13]
x=154992
y=44080
[Da14]
x=164208
y=42896
[Da15]
x=162672
y=42896
[Da16]
x=161136
y=42896
[Da17]
x=159600
y=42896
[Da18]
x=158064
y=42896
[Da19]
x=156528
y=42896
[Da20]
x=154992
y=42896
[Da21]
x=164208
y=41712
[Da22]
x=162672
y=41712
[Da23]
x=161136
y=41712
[Da24]
x=159600
y=41712
[Da25]
x=158064
y=41712
[Da26]
x=156528
y=41712
[Da27]
x=154992
y=41712
[Da28]

TABLE 6-continued x=164208
y=40528
[Da29]
x=162672
y=40528
[Da30]
x=161136
y=40528
[Da31]
x=159600
y=40528
[Da32]
x=158064
y=40528
[Da33]
x=156526
y=40528
[Da34]
x=154992
y=40528
[Da35]
x=164208
y=39344
[Da36]
x=162672
y=39344
[Da37]
x=161136
y=39344
[Da38]
x=159600
y=39344
[Da39]
x=158064
y=39344
[Da40]
x=156528
y=39344
[Da41]
x=154992
y=39344
[Da42]
x=164208
y=38160
[Da43]
x=162672
y=38160
[Da44]
x=161136
y=38160
[Da45]
x=159600
y=38160
[Da46]
x=158064
y=38160
[Da47]
x=156528
y=38160
[Da48]
x=154992
y=38160
[Da49]
x=164208
y=36976
[Da50]
x=162672
y=36976
[Da51]
x=161136
y=36976
[Da52]
x=159600
y=36976
[Da53]
x=158064
y=36976
[Da54]
x=156528

TABLE 6-continued y=36976
[Da55]
x=154992
y=36976
[Da56]
x=130160
y=48076
[Da57]
x=128624
y=48076
[Da58]
x=127088
y=48076
[Da59]
x=125552
y=48076
[Da60]
x=124016
y=48076
[Da61]
x=130160
y=46892
[Da62]
x=128624
y=46892
[Da63]
x=127088
y=46892
[Da64]
x=125552
y=46892
[Da65]
x=124016
y=46892
[Da66]
x=130160
y=45708
[Da67]
x=128624
y=45708
[Da68]
x=127088
y=45708
[Da69]
x=125552
y=45708
[Da70]
x=124016
y=45708
[Da71]
X=130160
y=44524
[Da72]
x=128624
y=44524
[Da73]
x=127088
y=44524
[Da74]
X=125552
y=44524
[Da75]
x=124016
y=44524
[Da76]
x=130160
y=43340
[Da77]
x=128624
y=43340
[Da78]
x=127088
y=43340
[Da79]
x=125552
y=43340
[Da80]
x=124016
y=43340

TABLE 6-continued

[Da81]
x=130160
y=42156
[Da82]
x=128624
y=42156
[Da83]
x=127088
y=42156
[Da84]
x=125552
y=42156
[Da85]
x=124016
y=42156
[Da86]
x=130160
y=40972
[Da87]
x=128624
y=40972
[Da88]
x=127088
y=40972
[Da89]
x=125552
y=40972
[Da90]
x=124016
y=40972
[Da91]
x=130160
y=39788
[Da92]
x=128624
y=39788
[Da93]
x=127088
y=39788
[Da94]
x=125552
y=39788
[Da95]
x=124016
y=39788
[Da96]
x=130160
y=38604
[Da97]
x=128624
y=38604
[Da98]
x=127088
y=38604
[Da99]
x=125552
y=38604
[Da100]
x=124016
y=38604
[Da101]
x=130160
y=37420
[Da102]
x=128624
y=37420
[Da103]
x=127088
y=37420
[Da104]
x=125552
y=37420
[Da105]
x=124016
y=37420
[Da106]
x=148848
y=24988
[[Da107]

TABLE 6-continued

```
x=147312
y=24988
[Da108]
x=145776
y=24988
[Da109]
x=144240
y=24988
[Da110]
x=148848
y=23804
[Da111]
x=147312
y=23804
[Da112]
x=145776
y=23804
[Da113]
x=144240
y=23804
[Da114]
x=148848
y=22620
[Da115]
x=147312
y=22620
[Da116]
x=145776
y=22620
[Da117]
x=144240
y=22620
[Da118]
x=148848
y=21436
[Da119]
x=147312
y=21436
[Da120]
x=145776
y=21436
[Da121]
x=144240
y=21436
[Da122]
x=148848
y=20252
[Da123]
x=147312
y=20252
[Da124]
x=145776
y=20252
[Da125]
x=144240
y=20252
[Da126]
x=148848
y=19068
[Da127]
x=147312
y=19068
[Da128]
x=145776
y=19068
[Da129]
x=144240
y=19068
```

It provides a flexible filing structure, whether the images are located in multiple places on a computer running a server program, or are collections held on removable storage media such as CD-ROMs and are just being viewed locally. The image data structure includes two modifiable text string byte arrays which are used to hold the file name and the folder name that identifies an individual image. When the server program is initiated, it searches all of its available storage (indicated in a setup file), finds any images present, reads the folder names and the file names of all of the images and creates URL path extensions for each one.

Figure 24:
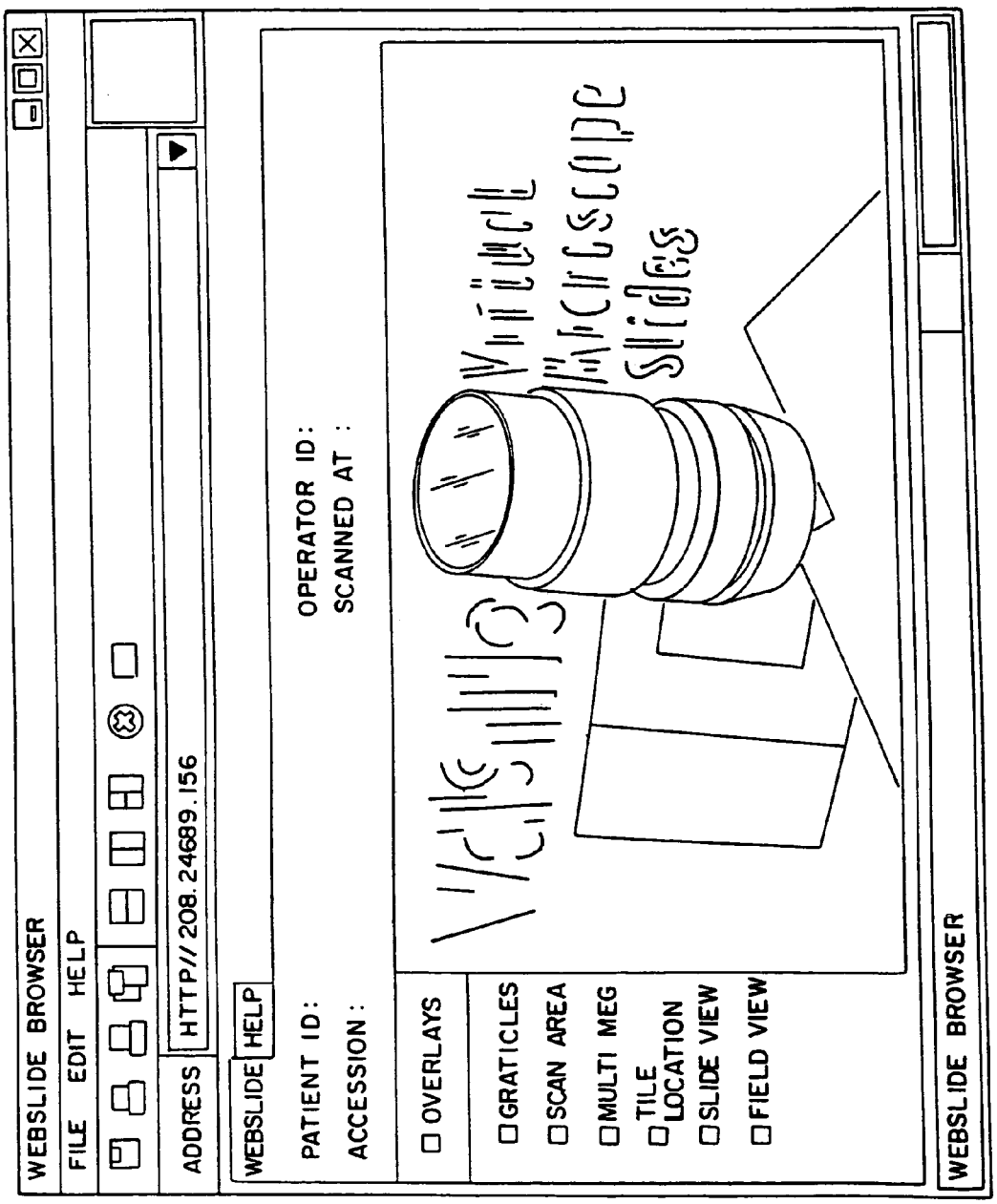
FIG. 24 shows a thin client browser main window upon initial activation of the thin client browser shown in FIG. 22A.
Figure 25:
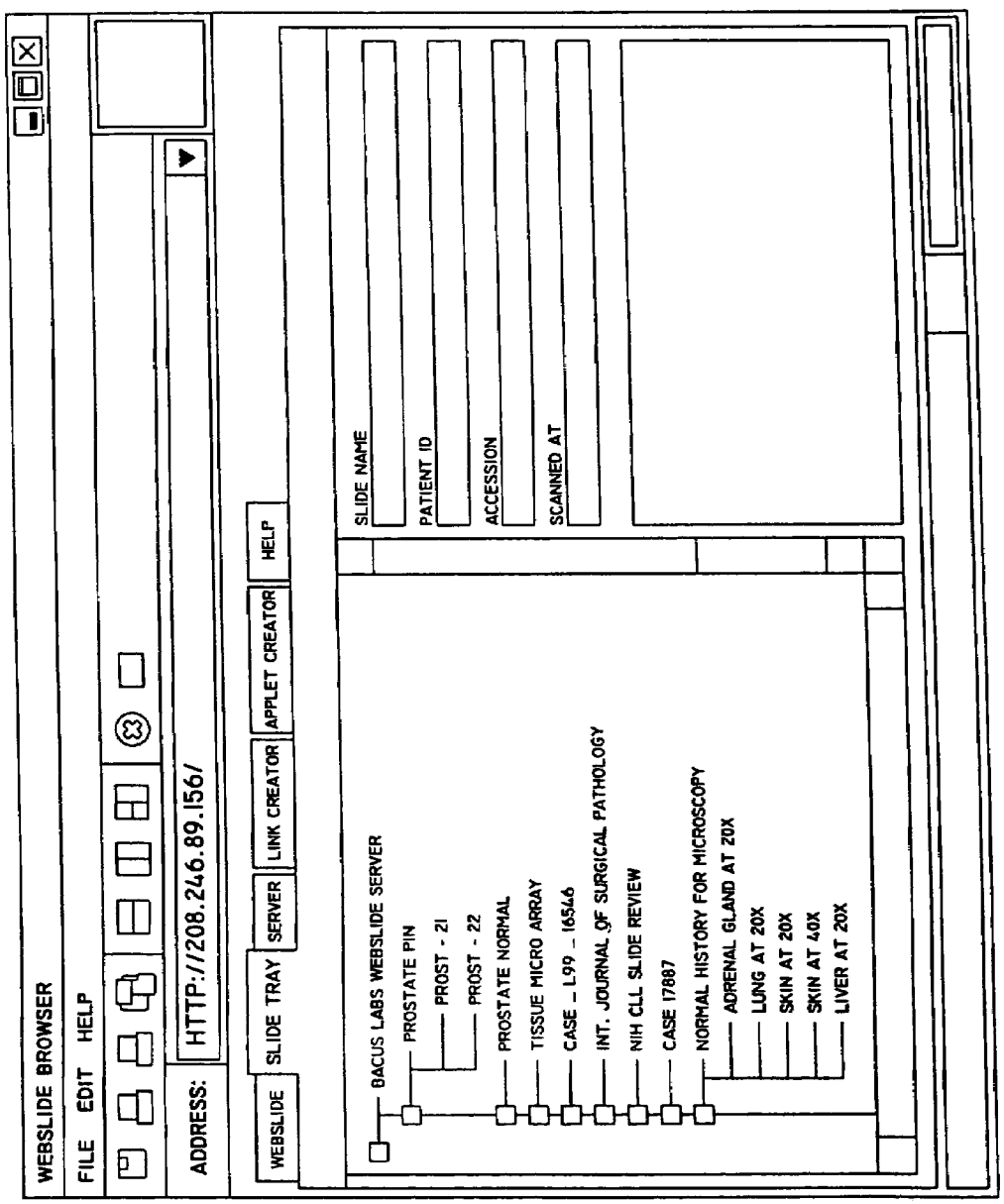
FIG. 25 shows a main window with a Slide Tray tab activated, showing available images from a remote server.

When the image browser initially starts its Main Window looks like FIG. 24. This is before a Login request has been initiated. The browser first sends a client Login Request using a specific server Internet address, such as shown in the address line of FIG. 20, and as indicated in Table 4. After the Login Request has been acknowledged, the browser then sends a Slide Tray Request. The server response to this is to send the list of image names and header text, their associated file folders, and the URL path extensions depending upon various image data structure storage locations on the server. The browser then constructs and displays in the Slide Tray tab of its main window a file folder tree structure display such as shown in FIG. 25. This is a dynamic display, such that a mouse click on the file folder opens up the file and displays its contained images. The browser responses are set forth in Tale 7 below.

TABLE 7

```
tResponse := tResponse + IntToStr0j0 + '&';
tResponse := tResponse + FrmMain.Client[j].tUserName + '&';
tResponse := tResponse + FrmMain.Client[j].tNickName + '&';
tResponse := tResponse + FrmMain.Client[j].tEmail + '&';
tResponse := tResponse + FrmMain.Client[j].tTrayIndex + '&';
tResponse := tResponse + FrmMain.Client[j].tSlide + '&';
tResponse := tResponse + FrmMain.Client[j].tSlideZoomLevel + '&';
tResponse := tResponse + FrmMain.Client[j].tSlideXRef + '&';
tResponse := tResponse + FrmMain.Client[j].tSlideYRef + '&';
tResponse := tResponse + FrmMain.Client[j].tFinalZoomLevel + '&';
tResponse := tResponse + FrmMain.Client[j].tXRef + '&';
tResponse := tResponse + FrmMain.Client[j].tYRef + '&';
tResponse := tResponse + FrmMain.Client[j].tSlideScanMode + '&';
tResponse := tResponse + FrmMain.Client[j].tPointerX + '&';
tResponse := tResponse + FrmMain.Client[j].tPointerY + '&';
if FrmMain.bLogoffClients then
    tResponse := tResponse + 'Server logoff issued...&'
else
    tResponse := tResponse + FrmMain.Client[j].tStatus + '&';
Inc(iCount);
  end;
end;
```

Figure 26:
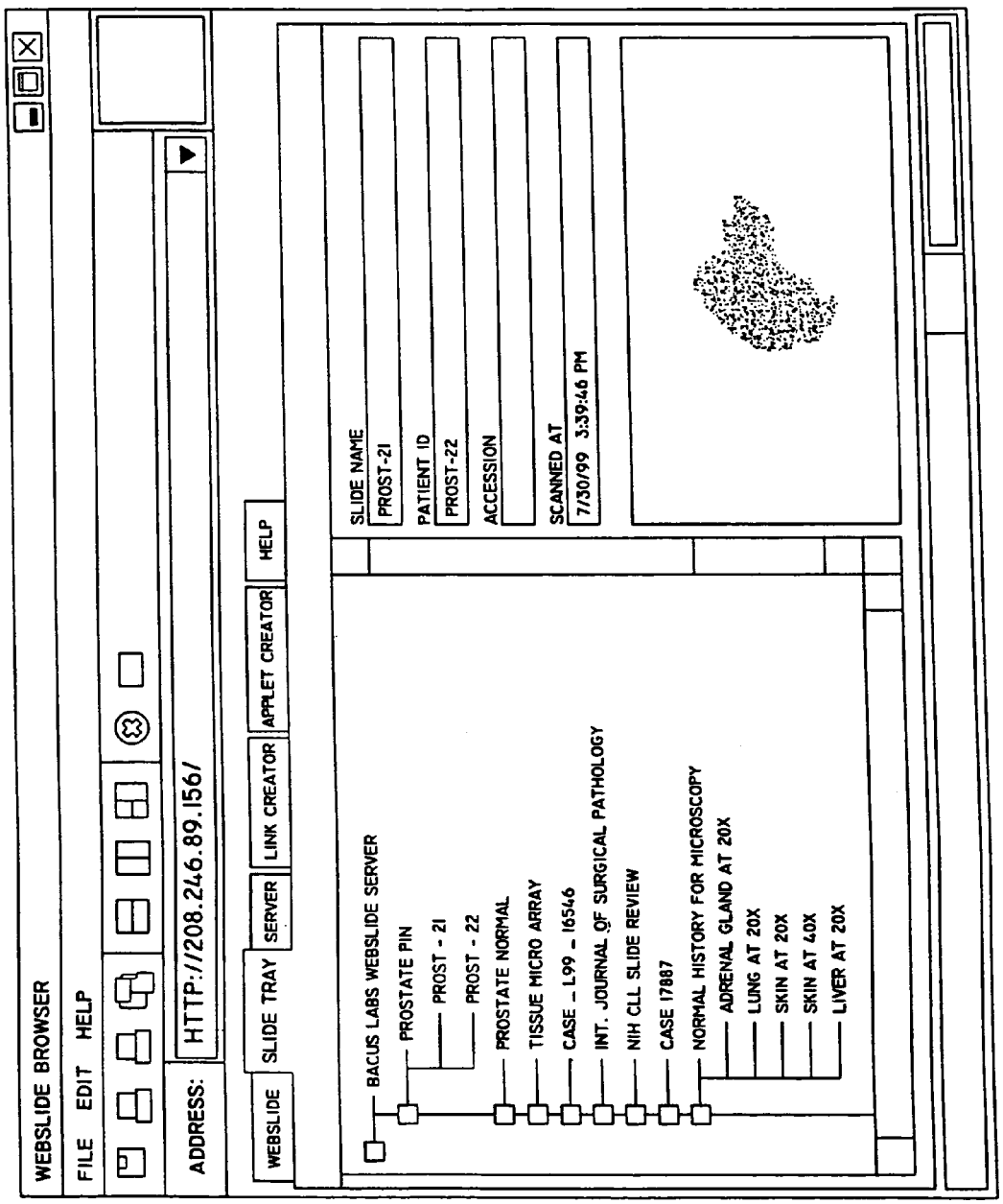
FIG. 26 shows a selection in the tray holding slide name Prost-z1 and showing a thumbnail image of a virtual slide together with associated identification information.

A mouse click on a specific image file name activates a client Image Request to the server, and the server sends back the requested thumbnail image which is displayed in the tab image area, as shown in FIG. 25. If one of the virtual microscope images is of further interest for more detailed observation, it can be retrieved by further mouse clicks, either on the thumbnail image or by a double click on the Slide Tray tree structure file name. In this case, the client browser sends a Select Slide Request. As indicated in Table 1, the server then sends the larger Preview Slide image along with the x, y coordinate list of all image tiles associated with that virtual slide. The tab changes from the Slide Tray to the image tab and the Preview Slide image is displayed in the image display area, as shown in FIG. 26.

One of the advantages of this virtual slide tray organizational design is that the folder names are carried as part of the image data set structure. This is different from a standard file structure where the file name is created and files are moved into the created folder. In a virtual microscope slide environment, collections of slides may come from different sources, e.g., on CD-ROMs or other storage media. This method carries the file folder information with the slide. The server can then automatically organize, on startup, all of the file folders depending upon the media in place at that time. For read/write media, the folder names can be edited to put specific images into different folders. This method also allows for automatic folder generation during the image creation process, which reduces the possibility of mixup for collections of slides that go together.

As described above, the image data set is created initially by scanning the microscope slide at two different magnifications. The initial scan, which is referred to as the Slide View scan, is performed with a 1.25× objective lens and can potentially use as many as 8×10, or 80 tiles, to cover the region of tissue or cells deposited on the slide. The second, higher-magnification scan is referred to as the Field View scan, and can occupy variable regions. These regions are mapped to the Slide View regions, and can be shown as overlaid areas.

Figure 27:
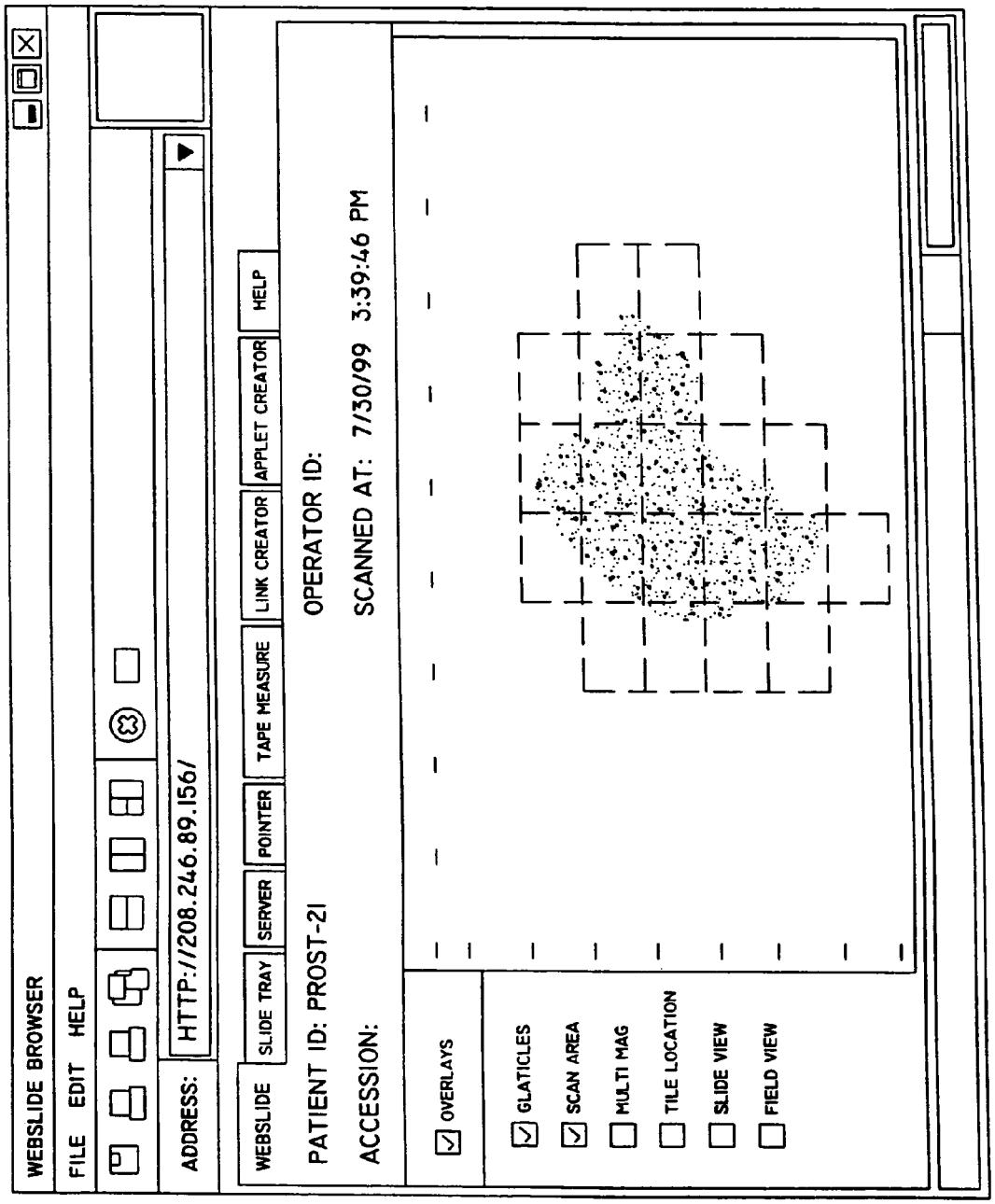
FIG. 27 shows a main window of the thin client browser showing a tab after selection of a virtual slide for detailed viewing in response to the Slide Tray tab.

As shown in FIG. 22, there are a number of overlays in the image tab of the main image browser window that can be used as aids in navigating the images. Two of these are shown there. They indicate potential regions that could have been scanned and those that were actually scanned on the specimen. Clicking on one of these regions, using the mouse as a pointer, instructs the browser to bring up the Slide Scan window, as shown in FIG. 27. Depending upon the size of the Slide View window and the location point specified in the Preview Slide image, the browser program can use the x, y image list and associated URL information that was transferred in response to the Select Slide Request to determine which Slide View scan image tiles are necessary. The browser then issues an Image Request for each image tile and paints in the received tiles to fill in the image display area in the window.

There are optional navigation overlays for this window also. The illustrated overlay shows regions where higher-magnification image tiles exist in the image data structure. By clicking in the region of one of these tiles, the browser is instructed to bring up its third window, the Field View window, shown overlain on top of the other two windows in FIG. 28. It uses the same procedure, e.g., the size of the Field View window to determine which high-magnification image tiles to request. The size of the Field View and Slide View windows can be changed to suit the user, for example, to fill the available viewing screen, and the browser program will request and fill in the necessary tiles to fill the viewing area.

A number of other viewing options are available, including changing the digital image magnification, i.e., lowering from 40× to 5×. In this case, more tiles are requested to fill in the available viewing area. The combination of the ability to change the various windows position and size, and the digital magnification (zoom) allows for full inspection of the virtual microscope specimen at high and low magnifications throughout the entire specimen. As additional image tiles are requested, they are cached locally so that additional inspection becomes quicker.

FIG. 29 is a flow chart of typical usage to further illustrate the above. This flow chart is shown as a sequence of related steps since some should occur before others and this is a typical sequence. However, it should be appreciated that the browser is multi-threaded as well as event driven. Most of the time, for example, the Update Request process is running on its own thread concurrently with client user event-driven processes, a shown in FIG. 29.

Referring back to FIGS. 18 and 19, Table 4 and the server description, it is clear that multiple clients can be logged-in at one time. All such clients independently view the same or different images. The design of the total combined system or all components is more powerful than that, however, through the use of the Update Request indicated in Table 1. Update Requests are generated by each user logged in the client browser at one-second intervals. Through the use of these Update Requests, the server is essentially functioning as a total system "state machine" for all of the logged-in users. Since each user is assigned an ID number upon login, the server can pass information regarding all of the other logged-in users, with regard to which slide they are viewing, where on that slide they are looking, the status of any pointer locations, etc. This all happens at one-second intervals for all logged-in clients. The browser then can use this information if desired to view the same images seen by other clients. This essentially means that the network of client viewers operates as a virtual multi-headed microscope, letting each other simultaneously view the same virtual slide.

Figure 30:
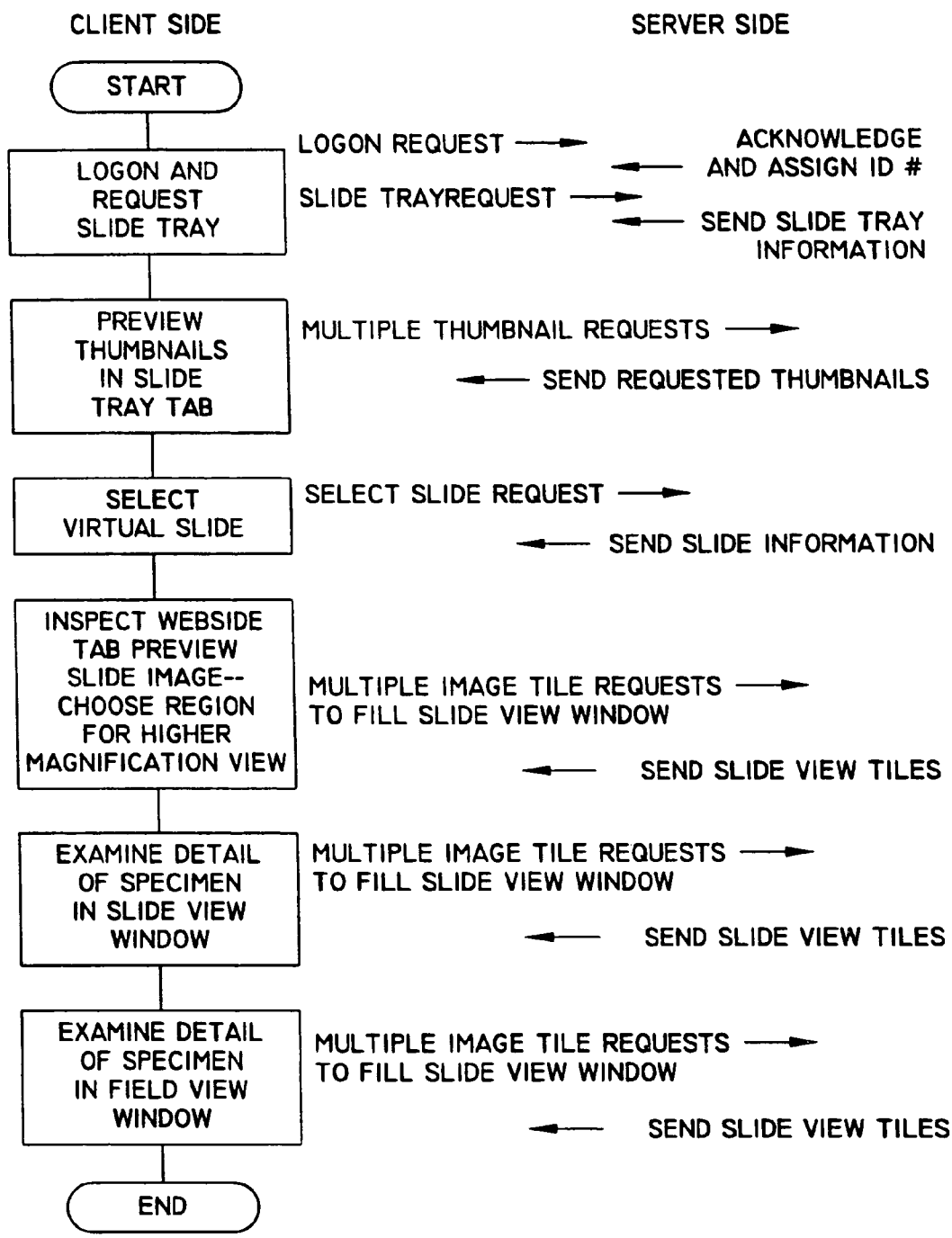
FIG. 30 is a flow chart of a typical sequence of interactions to view an image.

Additional features of the browser, as shown in FIG. 30, enhance this capability. The server tab in the main browser window, shown in FIG. 30, is used to activate a multi-headed virtual microscope function. A browser logged onto a server initially displays only the current user's information in the server tab. As Update Requests are serviced, if additional clients log onto the same server that information is also displayed in the Server tab, using additional login lines.

FIG. 30 shows two users logged into the same server. Also shown are buttons "Display another's view" and "Sync with another's view." After point and click highlighting of one of the logged-in user lines, the current user can then, for example, click on the button "Display another's view" and the browser will use the last update information on that user to send a Select Slide Request, and whatever Image Tile requests are necessary to display the same image view that the user is looking at. In a similar manner, if the user clicked on "Sync with another's view," then the browser would continue to use the update requests to change fields, zoom levels, etc. In the meantime, the various clients involved could communicate through the chat screen about the specimen under consideration.

Figure 31:
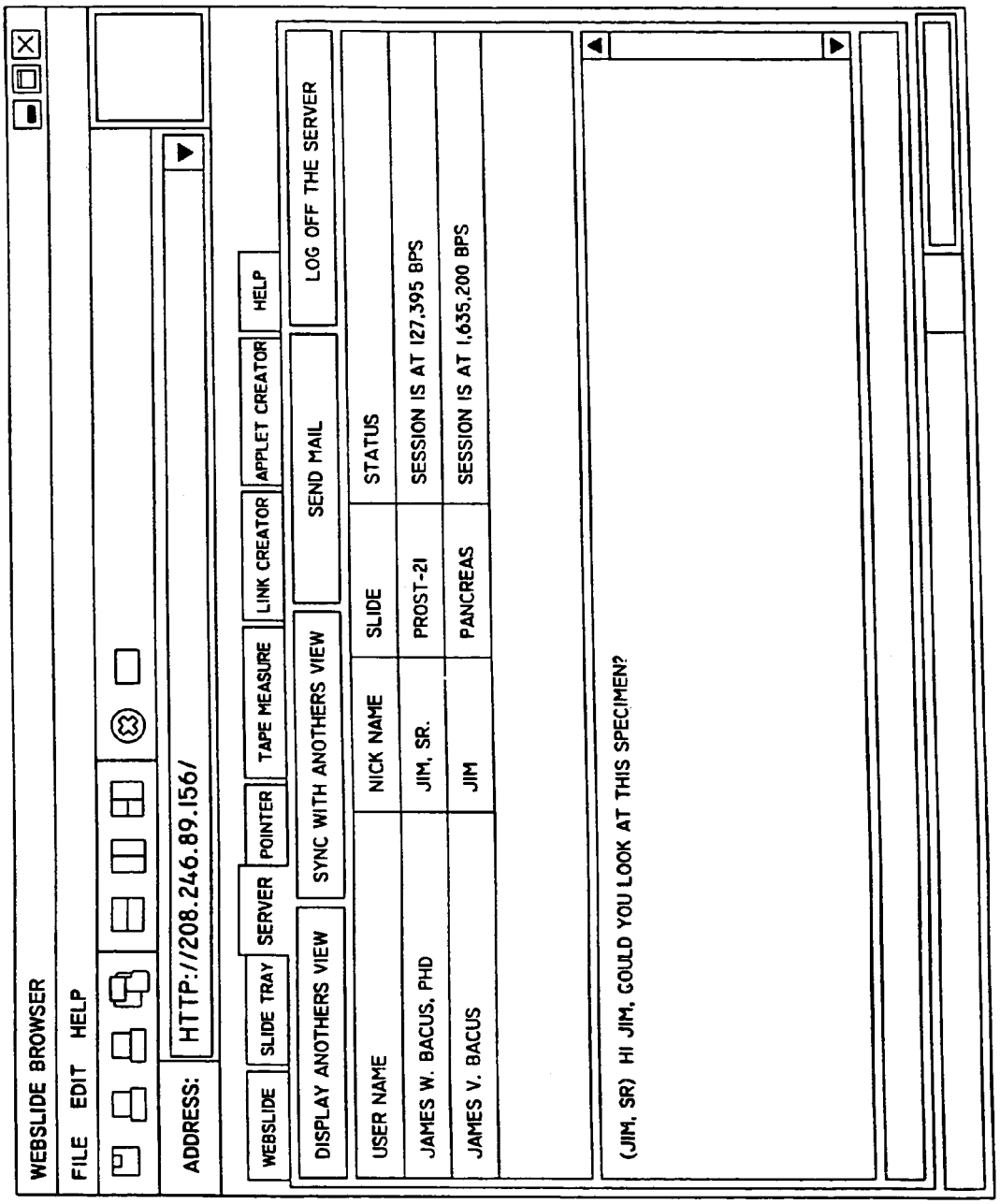
FIG. 31 shows a Server tab, showing options for multiple client interaction.
Figure 32:
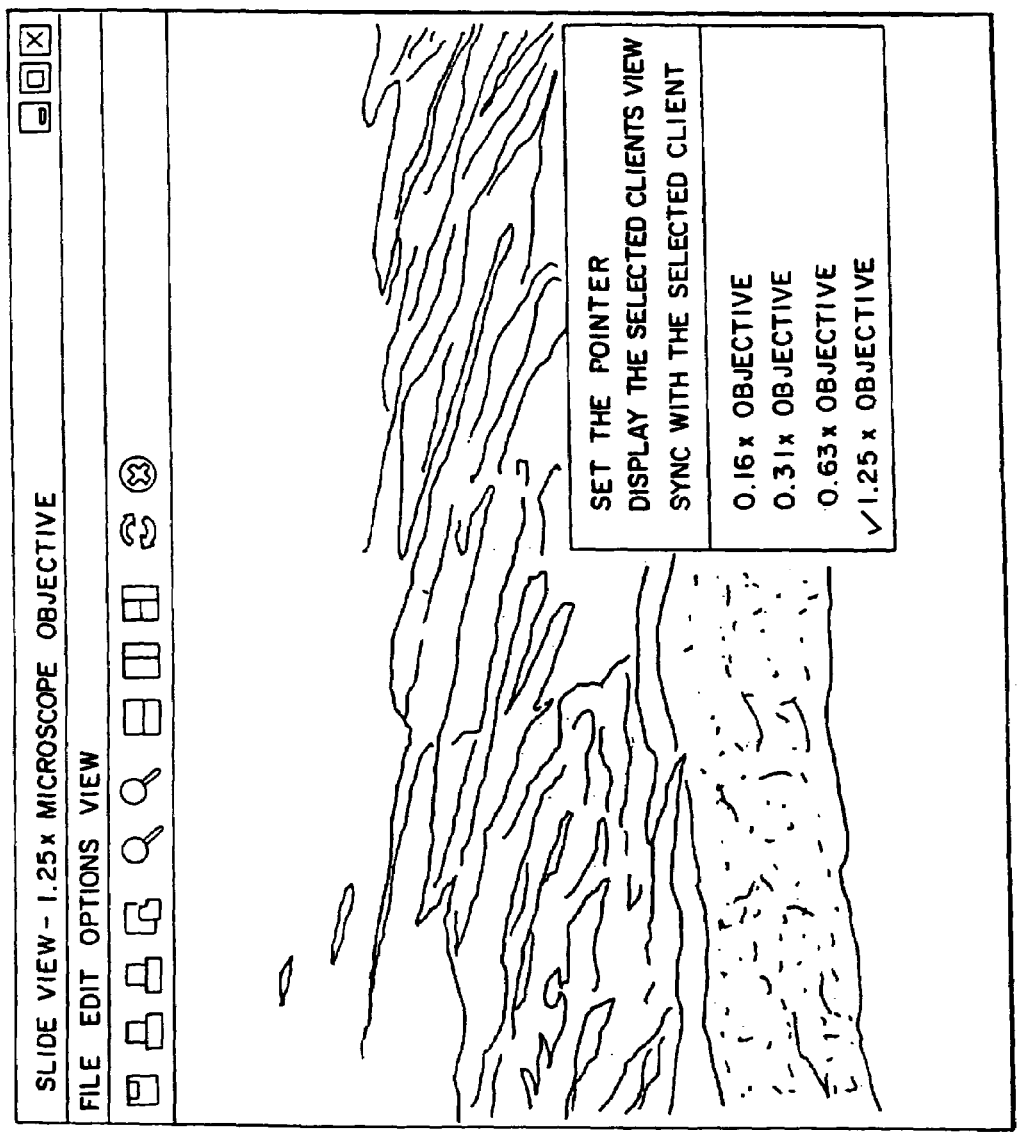
FIG. 32 shows a right mouse click activated pop-up menu when a pointer is positioned on an x, y location in the image area.

As shown in FIG. 28, a pointer may be drawn at any x, y location on an image screen view. A right click mouse event on an image where the pointer is desired activates program code which creates a pop-up menu, as shown in FIG. 31. When the "Set the Pointer" menu option is chosen, the position of the pointer is computed in x, y stage coordinate units and those position values are put in the main window Pointer tab and kept in memory to pass along to the server on the next update. Also, a pointer is placed on the image, as shown in FIG. 32, when another client, logged on at the same time, activates "Display another's view" (as shown in FIG. 30) for the client displaying the pointer, then that second client's browser would use the Update Request transferred x, y pointer position from the first client to put a pointer on the second client's image, after any Image Requests to the server were satisfied. In this way, two clients can pass arrows back and forth.

This is additionally facilitated by the right click mouse menu that each can use when she has the same image in front of her. Usually, this occurs when both parties are on the telephone, using the Internet and talking to each other while they move pointers back and forth, or synchronize on each other's views as desired.

They can also communicate through the Chat process using the Server tab, as shown in FIG. 28, or through e-mail through the Server tab. It should be appreciated that more than two clients may be logged on and participate in this process. This provides a multi-headed virtual microscope environment with pointers for multiple client users simultaneously.

One of the most important technological improvements in the "tiling" methodology is the improved resolution of image capture and display compared to previous methods of capturing images and transferring them over the Internet. The reason for this relates to microscopy optical resolution compared to digital camera sensor resolution, and the limited "field of view" imposed by the aperture sizes of the microscopy system. In order to match the optical resolution to the digital sensor resolution at high magnification with readily-available sensors, only a small part of the specimen can be captured at one time. Attempting to capture a larger view, e.g., with a lower magnification (and as a result lower optical resolution) objective microscope lens onto digital camera sensor, and then digitally magnifying the resulting captured image, results in "pixelated," "false" magnification. Tiled images can be captured at a matching pixel and optical resolution, and displayed seamlessly by the present invention, to achieve true virtual images. The same method automatically overcomes the limited "field of view" issue to preserve high resolution over large areas in the original high-magnification image plane of the microscope specimen.

Figure 33:
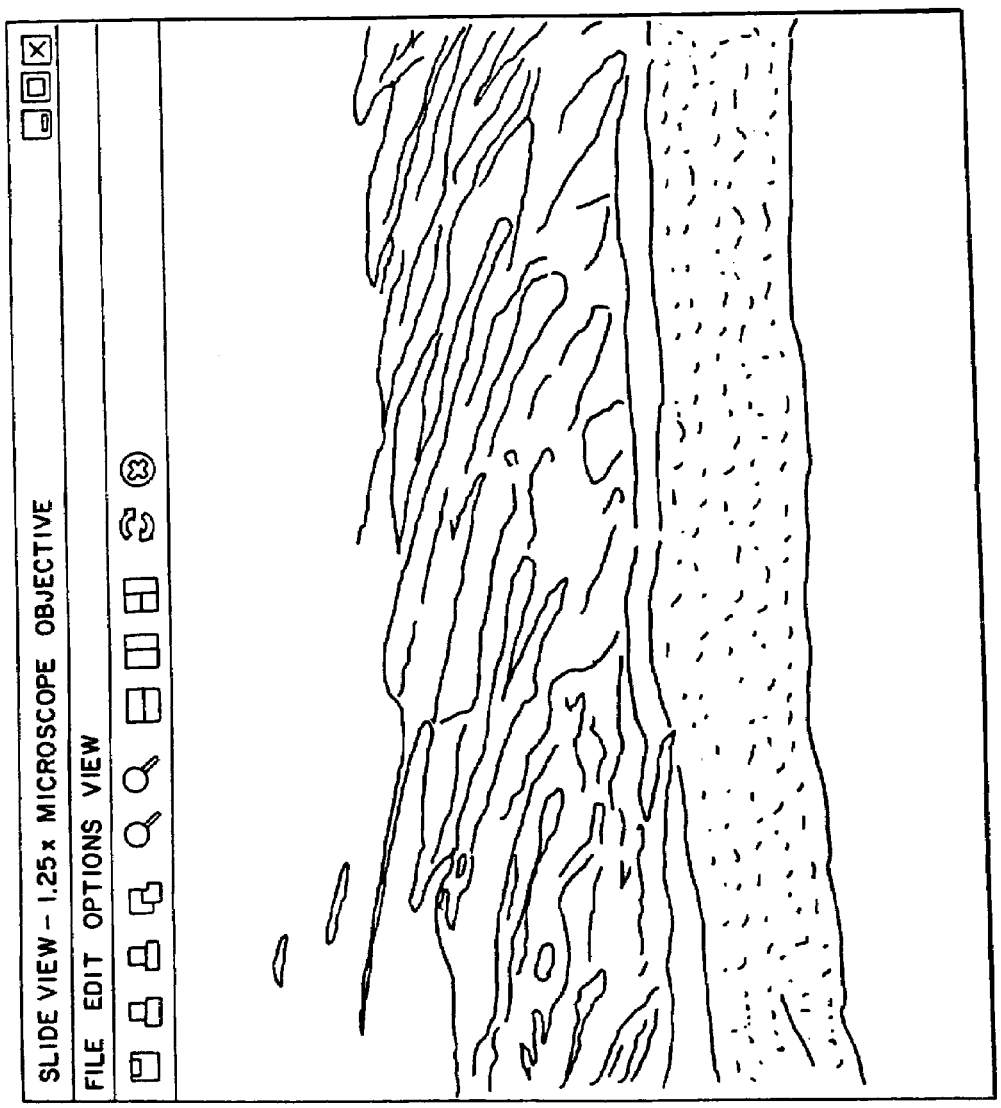
FIG. 33 shows a pointer position after choosing a "Set the Pointer" option in the menu of FIG. 32.

The method of retrieving and displaying these tiles as a coherent connected image is depicted in the flow diagram of FIG. 33. This flow diagram is relevant for choosing by a point and click, an image point in the Preview Slide image of the main browser window to open and display the Slide View window (or to choose another region to display in an already open Slide View window), or to open and display at a higher magnification the Field View window from a point in the Slide View window, or to display image areas not already pre-loaded in the Java applet portal window in an HTML browser page. An important factor in accomplishing seamless tiled image display according to the methods of this invention is to maintain an image x, y pixel reference to the original mechanical stage x, y coordinate reference. In the preferred embodiment, the x, y stage resolution is 0.1 micrometers per step. Each image tile is a known number of pixels, in this instance 752×480 pixels. Through calibration setup procedures during instrument construction, the number of stage coordinate steps per pixel is determined. This varies slightly from system to system and is different for each microscope objective. It is therefore recorded as part of each image data set. Table 8 shows some typical examples of one system.

TABLE 8

Example Stage x, y Coordinates per Image Tile Pixel

| Objectives | .1 Micrometer Stage Steps Per Pixel | Pixel Spatial Resolution In Micrometers |
|---|---|---|
| 1.25× | 69 | 6.9 |
| 10× | 9 | .9 |
| 20× | 5 | .5 |
| 40× | 2 | .2 |

Using the values from Table 8, if a Slide View image data set consisted of a full component of 8×10 image tiles, then there would be 7,520 pixels along the x direction and 3,840 pixels in the y direction. This would result in an x, y coordinate system for this slide of 518,880 x coordinate values and 264,960 y coordinate values. This, in effect, creates a virtual coordinate reference system for each tiled image data set. As each tile is collected, the initial upper left starting pixel location in stage coordinate values is stored in a separate subfile list as part of the image data structure file, along with, of course, that .jpg tile image. They are associated with each other by the name of the image tile being used as the name in the list associated with the x, y coordinates. In this way, each data structure has contained in it a list of x, y coordinate positions. The x, y coordinate position list is transferred to a specific client in response to the client issuing a Select Slide Request.

Referring again to FIG. 33, the initial step is to translate the starting display image size in pixels into the virtual stage coordinates. For example, if the image is the 452×240 Preview Slide image then each x pixel increments by 1,148× virtual stage coordinates and each y pixel increments by 1,104 virtual stage coordinates. A given mouse click resulting in an x, y pixel location can then be easily translated into a known virtual image x, y location. Next, the new display image window, in this case the Slide View image, is opened, and some of the possible 8×10 1.25× image tiles may be displayed. This window will either have a present initial size or will have been set by a previous call. In either case the size of the window in pixels can be determined from the associated windows properties parameters, accessible to the program. The size and placement of this window can then be calculated in the virtual coordinate space. The program assumes that the pixel point chosen in the previous window is associated with the center of the new window to do this.

Next, the image stage coordinate list is searched. The image stage coordinate list was previously transferred to find all candidate tilts which should be displayed according to size of the window.

As shown in FIG. 33, the tiles can be two types; they may already have been viewed and are there, and are therefore cached and available locally, or they exist on the server. If they are on the server, a Send Image Request is initiated and the server sends back the requested tile. Otherwise, they are read from the cache. It should be appreciated again in the case of the program's execution, shown in the flow chart of FIG. 33, that the program is event driven and multi-threaded. The final operation is to fill in the display window with the chosen tile. This same, or an analogous method of filling in tiles for display images is used in scrolling, zooming in and out, and in retrieving tiles for the Field View window (coming from the Slide View window), and in retrieving image tiles from the server for the fixed size Java applet viewer.

Even though in many instances these five images would be sufficient, the additional approach of this invention is to make available to the applet, the entire virtual slide. This is accomplished using the techniques already described for the browser. In this instance, the upper panel Preview Slide Image can be used by a mouse point and click, to locate an x, y position. This is translated into x, y virtual stage coordinates, and the needed tiles are requested through an Image Request to the server. If the magnification choices are used the operation of this application is handled by the same methods of zoom and calling for images as in the browser, all relating to the size of the window and which image tiles are needed from what virtual x, y location to fill in the window. In a similar way, the lower portion of the portal window is also enabled for scrolling. So the virtual slide advantage of scrolling and zooming in and out are available but in a limited size window. They are accessible, however, from an HTML document that has embedded content.

An additional feature of this approach, as shown by comparing FIGS. 21A, 21B and 22, is that the controlling HTML web-page code may be calling the content for the page from a computer other than the image computer. The advantage of this is that it decouples the text content from the image collections. In a teaching environment this enables many different users to create their own course content, using standard HTML methods, and simply provides a call to the server at appropriate places in the HTML code.

As indicated in FIGS. 18 and 19, and as discussed previously, the server also interacts with a second type of viewer, an HTML embedded applet, in this case written in the Java programming language, as set forth in Table 9 below.

TABLE 9

```
<APPLET CODEBASE="http://209.100.40.94/" CODE="WebSlide"
ALIGN="m
iddle" HEIGHT="590" NAME="Histology06a" WIDTH="464"
ALT="WebSlide">
    <PARAM NAME="lslidexrefpos" VALUE="82458">
    <PARAM NAME="webslideurl"
VALUE="http://209.100.40.94/WebSlides/
Histology06a/">
    <PARAM NAME="izoomlevel" VALUE="2">
    <PARAM NAME="lyrefpos" VALUE="23768">
    <PARAM NAME="lxssstepsize" VALUE="48062">
    <PARAM NAME="lxrefpos" VALUE="92237">
    <PARAM NAME="instance" VALUE="Histology06a">
    <PARAM NAME="lyssstepsize" VALUE="35892">
    <PARAM NAME="lslideyrefpos" VALUE="17177">
    This browser does not support Java v1.1 applets!
</APPLET>
```

The interaction of this viewer with the server is also shown in FIG. 22. This viewer is simpler, and used for different purposes than the browser, but uses many of the same techniques of transferring image tiles.

Figure 34:
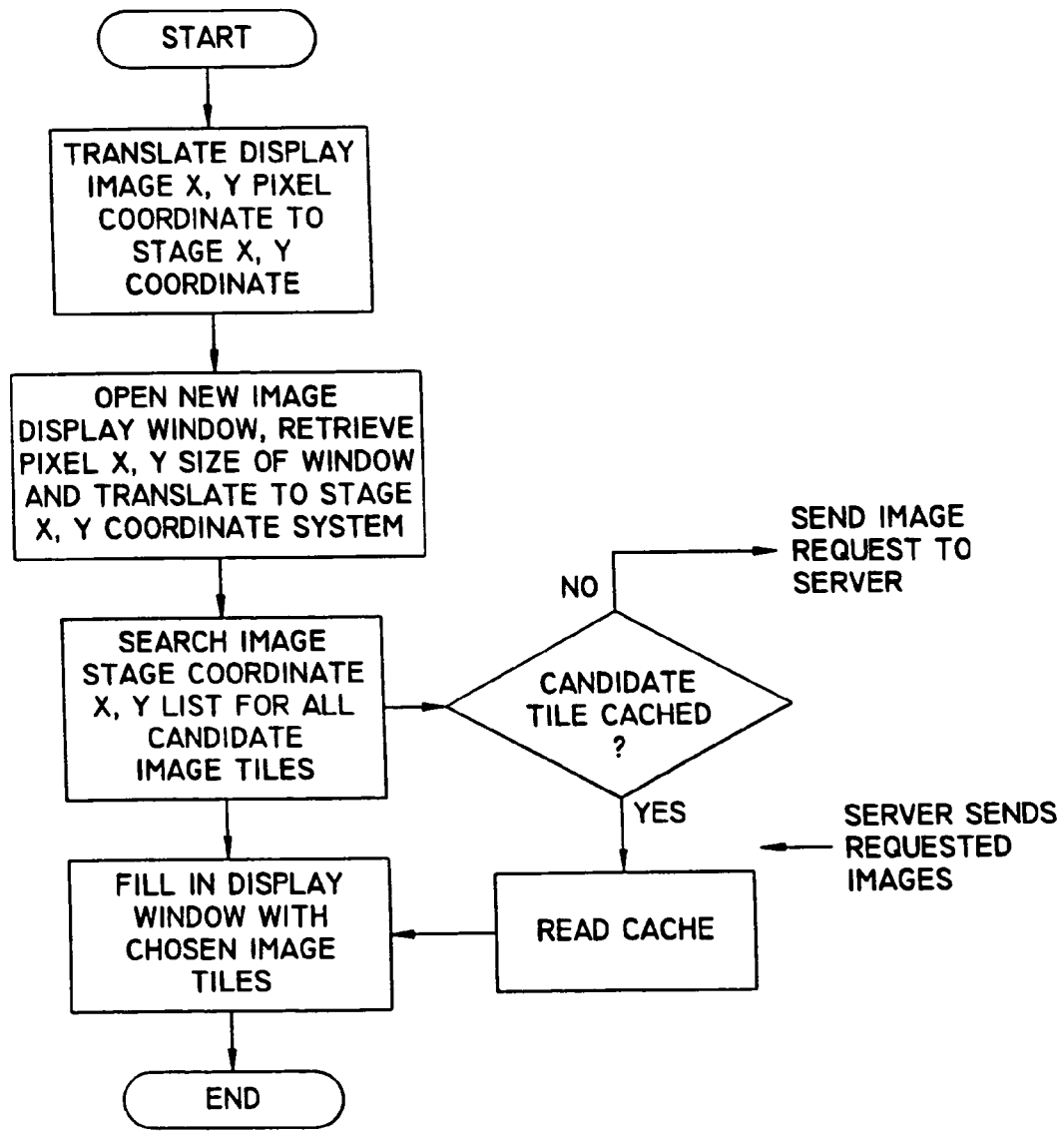
FIG. 34 shows a flow chart for major steps in process of filling in display windows with tiles.
Figure 35:
FIG. 35 shows an HTML-embedded Java applet viewer window.

FIG. 34 illustrates the layout and features of the HTML portal window created by this applet. This viewer consists of two views; a low-magnification view (which is the Preview Slide image discussed above) shown as an upper portion in FIG. 34, and a higher-magnification view shown in the lower portion. The two views are separated by a menu bar with four magnification choices. As described below, there is an HTML applet creation process which is another browser tab portion. This enables the creation of both the HTML code to generate a Java applet request and additional pre-configured images for the applet to use when it runs.

In an application of interest for this type of viewer, specific regions are identified in the image which are of primary interest, and the need is to see this region as quickly as possible and to change between magnifications rapidly. In order to enable this the applet creation process enables the location of a specific view on a given image, i.e., it specifies a center x, y position for the region and specifies a final view window size, of the same size as the lower portion of the portal window, and assembles from the tiled data structure four zoom level views corresponding to the menu bar magnification options. The zoom levels start with the highest Field View magnification level, usually 40× or 20×, and the viewer creates a lower-magnification image of each tile by using every other pixel at each lower zoom magnification. Additional tiles are brought in and assembled from the image data structure as needed to fill in the fixed field size of the lower HTML portal window. These four assembled images are referred to as Preview images, are given specific names in the creation process and are stored in a file accessible to the server program, on the same computer that the related image is located.

The first thing the Java applet does then after it is loaded is to send a Login and Virtual Slide Request as indicated in Table 1. If the slide name and server identity is correct, the server response is to send the Preview Slide image for the upper panel, the four Preview images that will be used for the lower panel, and the x, y list of all image tiles in the associated data structure. The HTML applet generation process specified which of the magnification choices would be loaded first. The other are available to the applet through the radio button event generated from the menu bar.

The advantage of this approach, of using the pre-stored Preview Slide and Preview images, is that they are small and can be transmitted relatively rapidly, essentially only five tiles, and are in essence pre-cached, in terms of the relationship to the browser description. One problem with applets is that they are interpreted rather than compiled; hence, they are slower than native machine code such as that used in the browser. Thus, this approach helps to overcome that. In addition, for many purposes, e.g., in an educational setting, these views are all that are needed to achieve the initial purpose. For the presentation of a microscope specimen, especially in anatomic pathology or histology, an overall view of the specimen, such as that shown in the upper portion, and localization of a specific region, with the ability to zoom in and out is sufficient.

The virtual slide link is set forth in Table 10 below.

TABLE 10

```
[WebSlide Link]
tWebSlideURL=http://209.100.40.94/
iMainTop=0
iMainLeft=0
tScanFilename=Prost-z2
iMainOverlays=1
bGraticles=1
bScanArea=1
bMultiMag=1
bTileLoction=0
bSlideView=1
bFieldView=1
iSlideViewTop=0
iSlideViewLeft=600
iSlideViewHeight=478
iSlideViewWidth=1000
iSlideViewWindowState=1
bDisplayTileLocationOverlay=1
iSlideViewZoomLevel=1
lSlideXRefPos=44397
lSlideYRefPos=55668
iFieldViewTop=478
iFieldViewLeft=0
iFieldViewHeight=402
iFieldViewWidth=472
iFieldViewWindowState=1
iFieldViewZoomLevel=1
lFieldViewXRefPos=58436
lFieldViewYRefPos=55520
tSlideScanMode=0
```

Figure 36A:
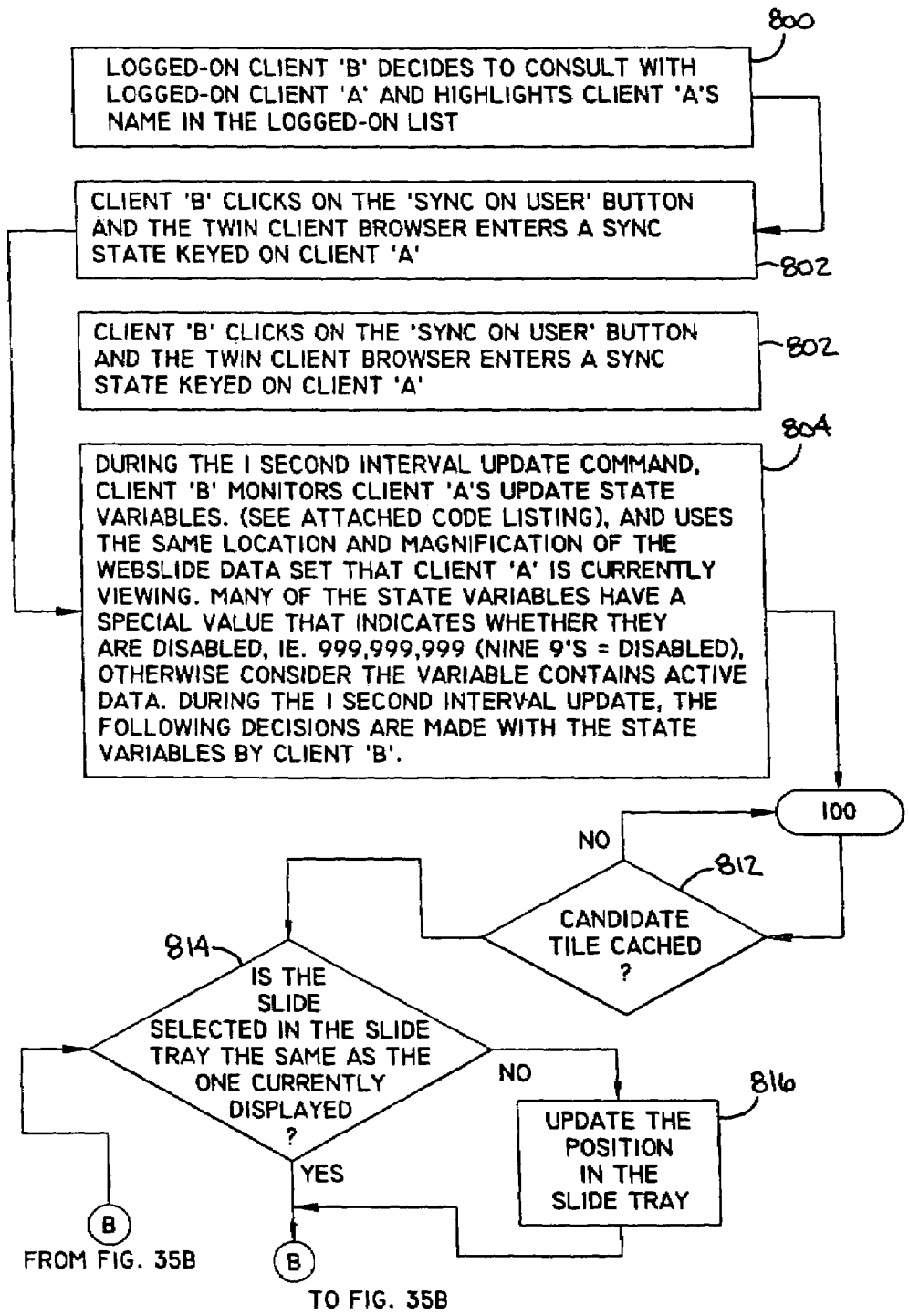

In order to perform the multiheaded microscope function of emulation, a plurality of clients are logged on, which might include a client A and a client B. After having logged on, client B elects to consult with logged on client A and highlights client A's name in logged on list in a step 800, as shown in FIG. 36(a). The client B then selects a synchronization and user function by clicking on the sync on user button and a thin client browser enters a synchronization state keyed on signals from client A in a step 802.

During the one-second interval update command for the browser, client B monitors client A's update state variables, as set forth in the listing in Table 6, and uses the variables necessary to display the same location and magnification of the slide data set that client A is currently viewing. A plurality of the state variables include state variable values that indicate whether those variables are disabled, for instance 999999999. Otherwise, the variable state is considered to contain active data and, during the one-second interval update, decisions are made by the state variables by client B, as set forth in step 804. Control is then transferred to a step 806 to determine whether the chat messenger index on the server is greater than the current state variable index. If it is, control is transferred to a step 808 to request each missing chat message from the server and displayed in the chat window at the client until the chat message index on the server is equal to the state variable index following which the routine returns in a step 810 to a test in a step 812 to determine whether the state variables have been placed in sync mode. If they have not, control is transferred back to the step 806, as shown in FIG. 36(*d*)

Figure 36C:
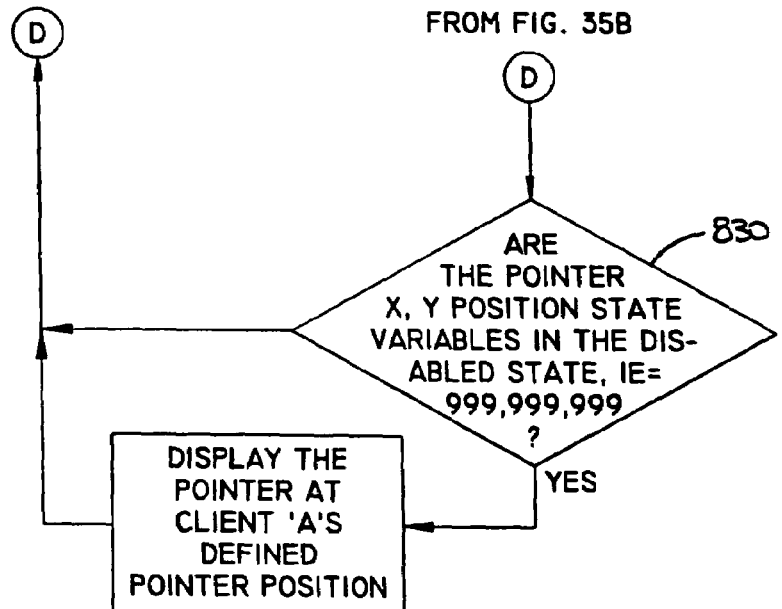
Figure 36D:
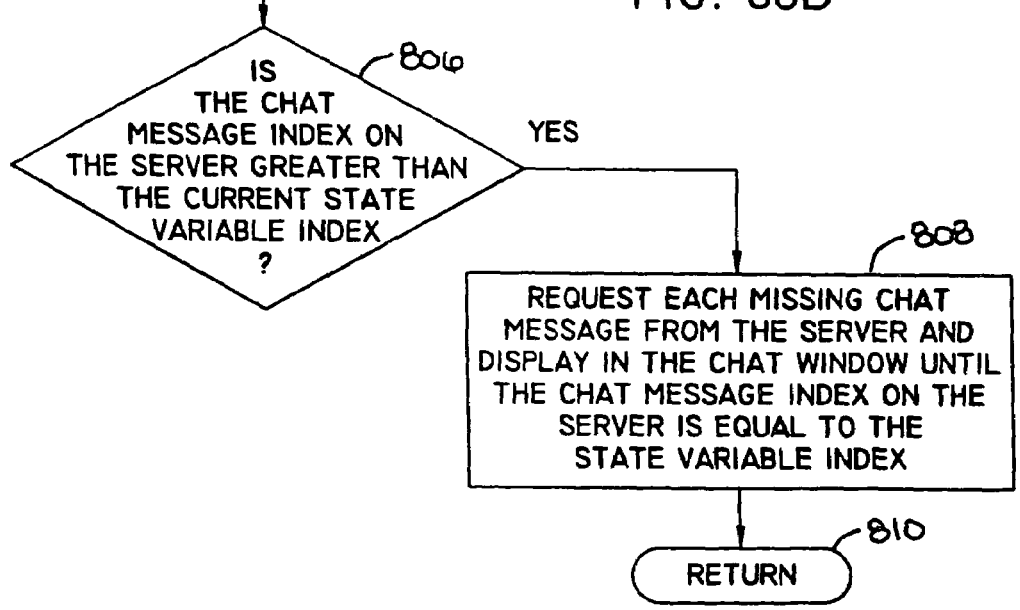

If the system is in sync mode, a test is made in a step 814, as shown in FIG. 36(*a*), to determine whether the virtual slide image selected from the slide tray data collection is the same as the one that is currently displayed. If it is not, the position in the slide tray is updated in a step 816. If it is, control is transferred either from step 814 or 816 to a step 818 where a test is made to determine whether the low-magnification x, y position location state variables are in the disabled state. If they are, control is transferred back to step 814. If they are not, the slide view window is displayed and updated for the low-magnification view to the lower-magnification position previously selected by client A using client A's current magnification state variable in step 820 in order to synchronize the views.

A test is then made in a step 822 similar to the step 818 to determine whether the high-magnification x, y location state variables are in the disabled state in a step 822 if they are disabled, control is transferred back to step 814. If they are not, control is transferred to a step 824 which displays the field view window on the client and/or updates the high-magnification view to synchronize with client A's x, y high-magnification selected position also using client A's current magnification state variables. The slide scan mode state variable indicates whether what is being displayed is the low-magnification or high-magnification data and each of the data's associated coordinate systems in field of view.

Control is then transferred to a step 830, as shown in FIG. 36(*c*), where a test is made to determine the mouse pointer or display pointer x, y position state variables in the disabled state or not. If they are not disabled, the pointer is displayed at the Location selected by client A and control is transferred to step 814. If the state variables are disabled, control is transferred directly to step 814.

It should be appreciated that the updating function from the client A variables may take place not just with one client, client B but over multiple clients in order to provide image coherency from the client, in this example client A, which in effect controls the command token for the virtual multi-headed microscope remote emulation.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. A method for viewing a specimen on a microscope slide of a specimen at a plurality of magnifications at a remote location from data transmitted over a common communication channel, the method comprising:

storing digitized data of a magnified image of the specimen with a server at a transmitting station;

sending a request from a remote location to the server for the digitized data for the specimen;

transmitting over a common communication channel the data structure having the digitized data to the remote location;

displaying from the received transmitted data on a viewer at the remote location a low magnification image of the specimen or a substantial portion thereof;

selecting a location on the displayed low magnification image for viewing at a higher magnification; and displaying the higher magnification image of the selected location to the viewer.

2. A method in accordance with claim 1 comprising:

using coordinate information for the selected location and the transmitted data to retrieve and to display the higher magnification image for the selected point on the viewer.

3. A method for viewing a virtual microscope slide in accordance with claim 1 comprising:

transmitting the data in packets over an Internet/Intranet common communication channel.

4. A method in accordance with claim 1 comprising:

displaying images of the selected location at each of multiple higher magnifications; and changing between the respective higher magnification images for the selected location.

5. A method in accordance with claim 4 comprising:

scrolling into view and displaying the location with adjacent images at a higher magnification.

6. A method in accordance with claim 1 comprising:

transmitting the data as a data structure to the remote location.

7. A method in accordance with claim 6 comprising:

using a browser at the remote location to assist in viewing and manipulating the images stored in the data structure and transmitted to the remote location.

8. A method in accordance with claim 7 comprising:

storing a plurality of virtual microscope slide on the server at the transmitting station.

9. A method in accordance with claim 8 wherein the transmitted data comprises:

sets of digital images with X, Y information organized to reconstruct and spatially align physically contiguous images at low magnification.

10. A method in accordance with claim 9 wherein the sets of digital images are tiles.

11. A method in accordance with claim 9 wherein the displayed higher magnification image of the selected location is a composite image of sets of digital images.

12. A method in accordance with claim 1 comprising:

placing a marker on the displayed low magnification image to indicate the selected location being viewed at the higher magnification.

13. A method in accordance with claim 1 comprising:

doing a quantitative analysis of the displayed higher magnification image of a histological specimen.

14. A method in accordance with claim 1 comprising:

reviewing a simultaneous display of both the low magnification and high magnification images to analyze cells forming part of an architectural feature for cancer or another disease.

15. A method in accordance with claim 1 providing programs for and doing a quantitative analysis of selected portions of the specimens being displayed.

16. A method in accordance with claim 1 wherein the location to be viewed at higher magnification comprises:

a segment selected on the low magnification image by the viewer for capture and storage as digitized data stored with the server.

17. A method in accordance with claim 16 comprising:
using a marker to draw an outline about the segment on the low magnification image to capture the segment at higher magnification.

18. A method in accordance with claim 1 comprising:
providing a plurality remote locations with viewers seeing the same image being displayed;
marking the same selected location on the low magnification view at each remote location; and
displaying the same selected high magnification image at each remote location thereby providing a multi-head microscope.

19. A method in accordance with claim 1 comprising:
navigating along an architectural feature being displayed on a low magnification image of the specimen and selecting successive locations during this navigation for display as higher magnification images.

20. A method in accordance with claim 1 using several different browsers, viewers and computers to access the digitized data at the transmitting station for transmission to the remote location.

21. A method in accordance with claim 1 comprising:
storing images in multiple storage for access with a computer running a server program; and
slide specimen images having been stored on different storage means including a portable disk storage medium.

22. A method of viewing magnified digitized images of microscope slide specimens stored in an organized collection of virtual microscope slides and transmitted over a common communication channel to a remote viewer, the method comprising:
providing a server at a transmitting station and storing a collection of organized virtual microscope slides having data for magnified, digitized images of their respective specimens;
accessing the transmitting station from a remote location and requesting transmission of image data for a specified virtual microscope slide;
transmitting image data for the specified virtual microscope slide over the common communication channel to the remote location;
displaying from the transmitted data a digitized image at low magnification of at least a portion of the specimens;
selecting a location on the digitized image of the specimen for viewing at a higher magnification; and
displaying a digitized image at the higher magnification image for the selected location at the remote location.

23. A method in accordance with claim 22 comprising:
using a browser software program with the data at the remote location to view the respective images.

24. A method in accordance with claim 22 providing a program that organizes virtual microscope slides for the data structures into a tree structured, folder presentation for selection of a specific virtual microscope slide for viewing.

25. A method in accordance with claim 22 providing multiple users on the common communication channel to see each others displayed magnified image of the selected microscope slide specimen.

26. A method in accordance with claim 25 comprising:
using an interactive painter on a magnified view to indicate the location of the higher magnification being seen at the respective remote locations.

27. A method in accordance with claim 25 comprising:
providing voice communication for discussion between the respective viewers of the magnified, digitized images of the specimen.

28. A method in accordance with claim 22 wherein the transmitting of the data structure comprises:
transmitting an active, dynamic control program allowing the viewer to interact and manipulate the viewed images at multiple magnifications at the remote location.

29. A method in accordance with claim 22 comprising:
providing a thin client browser at the remote location for interaction with the server.

30. A method in accordance with claim 22 comprising:
storing the viewed images locally in a cache; and
retrieving and displaying stored images locally at the remote location.

31. A method in accordance with claim 22 comprising:
sending an image request for an image at a specified magnification and at a specified location on the specimen; and
retrieving the specified images from the server and transmitting it to the remote location for viewing an image at the location and at the specified magnification.

32. A method in accordance with claim 22 comprising:
displaying to the viewer at the remote location an overall, low magnification image of the specimen or a substantial portion thereof, the overall, low magnification image being digitally reduced in size.

33. A method in accordance with claim 22 comprising:
providing a file structure for data structures at the transmitting station;
transmitting to the remote station and displaying thereat a list of image names and header text for file folders;
interactively selecting a file folder and displaying its contained images;
selecting a specific image file image and requesting from the server an image of the specimen; and
displaying the requested image at the remote location.

* * * * *